United States Patent [19]
Sauer et al.

[11] Patent Number: 5,955,440
[45] Date of Patent: Sep. 21, 1999

[54] MACROLIDE LHRH ANTAGONISTS

[75] Inventors: Daryl R. Sauer, Trevor, Wis.; Fortuna Haviv, Deerfield, Ill.; John Randolph, Mundelein, Ill.; Nicholas A. Mort, Waukegan, Ill.; Christopher R. Dalton, Mundelein, Ill.; Milan Bruncko, Lake Bluff, Ill.; Michele A. Kaminski, Beach Park, Ill.; Bradley W. Crawford, Gurnee, Ill.; Lisa Marie Frey, Mundelein, Ill.; Jonathan Greer, Chicago, Ill.

[73] Assignee: Abbott Laboratories, Abbott Park, Ill.

[21] Appl. No.: 09/049,963

[22] Filed: Mar. 27, 1998

[51] Int. Cl.$^6$ .............................. A61K 31/70; C07H 1/00; C07H 17/08
[52] U.S. Cl. ............................... 514/29; 536/7.2; 536/7.4; 536/18.5
[58] Field of Search ............................... 514/29; 536/7.2, 536/7.4, 18.5

[56] References Cited

U.S. PATENT DOCUMENTS 4,677,097  6/1987  Omura et al. ............................ 514/29

FOREIGN PATENT DOCUMENTS

| | | |
|---|---|---|
| 0215355 A2 | 3/1987 | European Pat. Off. . |
| 0248279 A2 | 12/1987 | European Pat. Off. . |
| 0349100 A2 | 1/1990 | European Pat. Off. . |
| 0559896 A1 | 9/1993 | European Pat. Off. . |

*Primary Examiner*—Elli Peselev
*Attorney, Agent, or Firm*—Mona Anand

[57] ABSTRACT

Disclosed are 3'-N-desmethyl-3'-N-substituted-6-O-methyl-11-deoxy-11,12-cyclic carbamate erythromycin A derivatives which are antagonists of lutenizing hormone-releasing hormone (LHRH). Also disclosed are pharmaceutical compositions comprising the compounds, to methods of using the compounds and to the process of making the same.

15 Claims, No Drawings

MACROLIDE LHRH ANTAGONISTS

TECHNICAL FIELD

The present invention relates to a class of macrolide compounds which are antagonists of lutenizing hormone-releasing hormone (LHRH), to pharmaceutical compositions comprising the compounds, to methods of using the compounds and to the process of making the same. More particularly, the present invention relates to 3'-N-desmethyl-3'-N-substituted-6-O-methyl-11-deoxy-11,12-cyclic carbamate erythromycin A derivatives which are antagonists of LHRH.

BACKGROUND OF THE INVENTION

The gonadotropins, follicle stimulating hormone (FSH), lutenizing hormone (LH), and chorionic gonadotropin (CG) are required for ovulation, spermatogenesis, and the biosynthesis of sex steroids. A single hypothalamic hormone, gonadotropin-releasing hormone (GnRH) also known as LHRH is responsible for regulating the secretion of both FSH and LH in mammals.

LHRH is a decapeptide having the structure:

pyro-Glu$^1$-His$^2$-Trp$^3$-Ser$^4$-Tyr$^5$-Gly$^6$-Leu$^7$-Arg$^8$-Pro$^9$-Gly$^{10}$-NH$_2$ where the superscripts designate the position of each aminoacyl residue in the decapeptide chain.

LHRH is released from the hypothalamus and binds to a receptor on the pituitary gland, causing the release of LH and FSH which subsequently act on the gonads to stimulate the synthesis of steroid sex hormones. The pulsatile release of LHRH, and thereby the release of LH and FSH, controls the reproductive cycle in animals and humans. Acute doses of LHRH agonists increase the levels of LH and steroidal sex hormones in both animals and humans. Paradoxically, chronic doses of LHRH agonists suppress the level of LH and steroidal sex hormones. Consequently, the effect of multiple doses of LHRH agonists is to suppress estrogen formation in females and testosterone production in males. The same effect is observed in both animals and humans after administration of either acute or chronic doses of LHRH antagonists.

In recent years considerable research effort has been expended on finding antagonists of LHRH. These efforts have produced a number of peptide LHRH antagonists, which suppress LH and reproductive hormones in mammals upon acute or chronic administrations. See for example, M. J. Karten in "Modes of Action of GnRH and GnRH analogs", edited by W. F. Crowley and P. M. Conn, p. 277 (1992). The literature has reported that LHRH antagonists are useful in the treatment of a variety of conditions in which the suppression of sex steroids plays a key role including contraception, delay of puberty, treatment of benign prostatic hyperplasia, palliative treatment or remission of hormonal-dependent tumors of the prostate, the treatment of cryptorchidism, hirsutism in women, gastric motility disorders, dysmenorrhea, and endometriosis.

Current LHRH antagonists are decapeptides which, because of their low oral bioavailability, are administered either intravenously or subcutaneously. Non-peptide heterocyclic antagonists have been reported in the literature, see for example, WO 95/29900, WO 97/22707, and WO 97/21704. Non-peptide LHRH antagonists have the possible advantage of improved oral bioavailability and are smaller molecules.

However, there are no known reports of macrolide compounds as LHRH antagonists in the literature. Macrolide antibiotics and macrolide prokinetic agents are known. For example, macrolide antibiotics derived from erythromycin which contain 11,12-cyclic carbamate moieties are disclosed in EP 248 279 A2. The 3'-N substituted erythromycin derivatives, which are effective antibacterial agents are described in EP 0 559 896 A1. Macrocyclic lactone (macrolide) prokinetic agents are known. See J. S. Gidda et al., in European Patent Application No. 0349100, published Jan. 3, 1990, which discloses 12-membered macrolides for use as gastrointestinal motility enhancers. S. Omura and Z. Itoh, in U.S. Pat. No. 4,677,097, issued Jun. 30, 1987; European Application No. 215,355, published Mar. 25, 1987; and European Application No. 213,617, published Mar. 11, 1987; disclose derivatives of erythromycins A, B, C and D which are useful as stimulants of digestive tract contractile motion. Additionally, T. Sunazuka, et al., Chem. Pharm. Bull. 37(10): 2701–2709 (1989) discloses quaternary derivatives of 8,9-anhydroerythromycin A 6,9-hemiacetal and 9,9-dihydro-erythromycin A 6,9-epoxide with gastrointestinal motor stimulating activity.

None of these references disclose novel 3'-N-desmethyl-3'-N-substituted-6-O-methyl-11-deoxy-11,12-cyclic carbamate erythromycin A derivatives of the present invention, which are effective as LHRH antagonists.

SUMMARY OF THE INVENTION

In one aspect, the present invention relates to a compound having the formula:

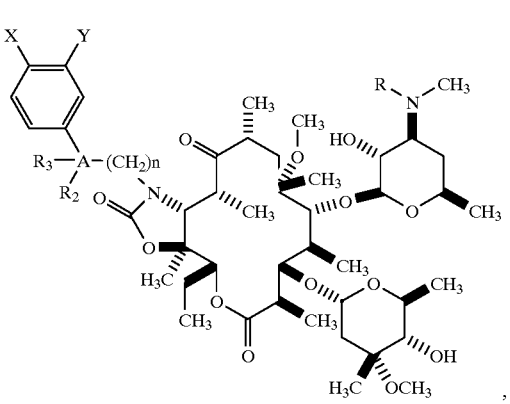

or a pharmaceutically acceptable salt or ester thereof, wherein
A is selected from the group consisting of:
  (a) —C,
  (b) —N, and
  (c) —O;
X and Y are independently at each occurrence selected from the group consisting of:
  (a) hydrogen,
  (b) halide,
  (c) trifluoromethyl,
  (d) alkoxy,
  (e) alkyl,
  (f) aryl, and
  (g) substituted aryl;
R is selected from the group consisting of:
  (a) alkyl,
  (b) cycloalkyl,
  (c) heterocylic, (d) substituted heterocyclic,
(e) alkylcycloalkyl,
(f) substituted alkylcycloalkyl,
(g) alkylaryl,
(h) alkylheterocyclic,
(i) alkenyl,
(j) alkynyl,
(k) —C(S)—NHR$_4$, C(NR$_4$)—NHR$_4$, wherein R$_4$ is hydrogen, alkyl, or aryl; and
(l) —(CH$_2$)$_n$—C(CH$_2$)$_m$—R$_5$, wherein m is 2, 3, 4, or 5, and R$_5$ is alkyl, alkoxy, aryl, or substituted aryl;

R$_2$ and R$_3$ are independently at each occurrence
(a) hydrogen,
(b) methyl, or R$_2$ and R$_3$ together form a cyclic moiety, when A is C; R$_3$ is absent when A is N; and
n=1, 2 or 3.

In another aspect, the present invention relates to a process for preparing the compound formula I. The process comprises the steps of:

(a) reacting a compound of formula:

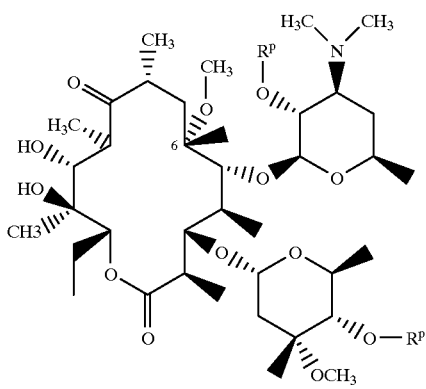

with sodium hexamethyldisilazide and carbonyldiimidazole to afford a compound of the formula:

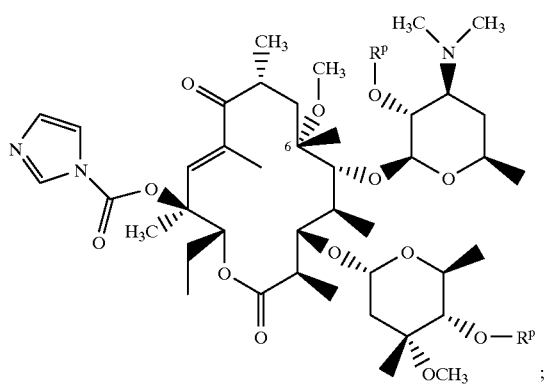

(b) reacting the compound obtained in step (a) with a compound an amino compound of the formula:

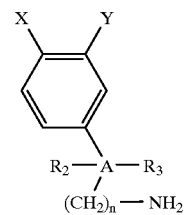

followed by deprotection of 2',4"-protected hydroxyl groups to afford a compound of the formula:

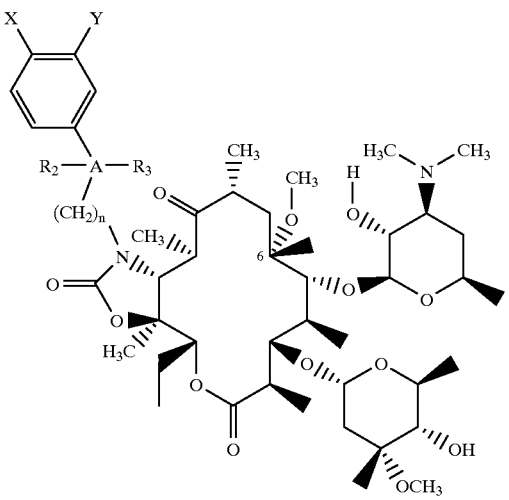

(c) desmethylating the 3'-amino by treating the compound obtained in step (b) with iodine in presence of a base to afford a compound of the formula:

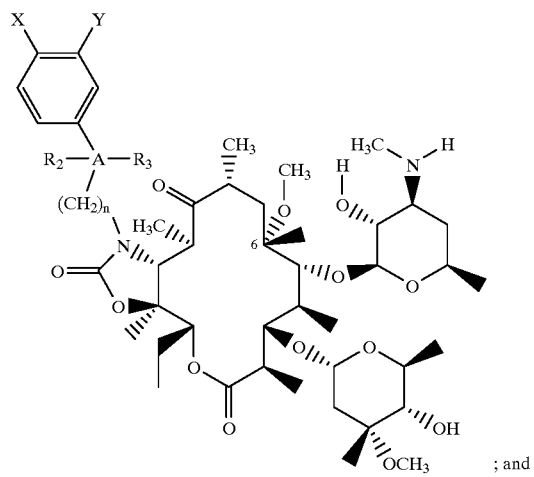

(d) alkylating the 3'-N-desmethylated compound obtained in step (c) with an alkylating agent.

The compounds of the invention exhibit little or no antibacterial activity, but they bind to the LHRH receptors and are effective LHRH antagonists. Thus, these compounds are effective in the treatment of prostate cancer, endometriosis, precocious puberty and other types of diseases which are related to sex hormones.

Accordingly, in another aspect of the invention, the present invention relates to pharmaceutical compositions which are useful as LHRH antagonists and suppress LH, testosterone, estradiol and estrogen in mammals.

In still another aspect, the present invention relates to a method of suppressing levels of sex hormones in male or female mammals comprising administering to a host in need of such treatment a therapeutically effective amount of an LHRH compounds in combination with a therapeutically effective amount of an antiandrogenic agent.

DETAILED DESCRIPTION OF THE INVENTION

The terms "loweralkyl" or "alkyl" as used herein refer to straight or branched chain alkyl radicals containing from 1 to 20 carbon atoms, sometimes represented as Cx-Cy-alkyl where x and y respectively represent the minimum and maximum number of carbon atoms in the alkyl radical. Examples of loweralkyl include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" or "lower alkoxy" as used herein refers to a loweralkyl group, as defined above, which is bonded to an oxygen atom in an ether linkage. Examples of alkoxy include, but are not limited to, methoxy, ethoxy, isopropoxy, n-pentyloxy, t-butoxy, n-octyloxy and the like. This alkoxy radical can also contain a ring which includes, but is not limited to, a five or six atom ring composed of carbons, which may contain one or two heteroatoms such as nitrogen, oxygen.

The term "alkenyl" as used herein refers to a branched or straight hydrocarbon chain comprising two to twenty carbon atoms, preferably four to twelve carbon atoms, especially about eight to ten carbon atoms, which also comprises one or more carbon-carbon double bonds, preferably about one to three double bonds. Compounds of the invention may either have a known configuration or may exist as a mixture of isomers.

The term "alkynyl" as used herein refers to a branched or straight hydrocarbon chain comprising two to twenty carbon atoms, preferably four to twelve carbon atoms, especially about eight to ten carbon atoms, which also comprises one or more carbon-carbon triple bonds, preferably about one triple bond. Compounds of the invention may either have a known configuration or may exist as a mixture of isomers.

The term "cycloalkyl" as used herein refers to a saturated monocyclic hydrocarbon group having from three to seven carbon atoms in the ring, including, but not limited to, cyclopropyl, cyclobutyl, cyclopentyl, cyclohexyl, cycloheptyl and the like. The cyclic group may be optionally substituted with, for example, lower alkyl, hydroxy, halogen or an amino group.

The term "alkylcycloalkyl" as used herein refers to a cycloalkyl group as defined above, appended to a loweralkyl radical. The alkylcycloalkyl group is attached to the parent moiety through the alkyl radical wherein the alkyl radical is of one to six carbon atoms. Examples include, but are not limited to, cyclopropylmethyl, cyclopropylethyl, cyclobutylmethyl and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-) amino, formyl, carboxy, alkoxycarbonyl, $C_1$-$C_3$-alkyl—CO—O—, $C_1$-$C_3$-alkyl—CO—NH—, or carboxamide; except that tetrafluorophenyl and pentafluorophenyl are also included within the definition of "substituted aryl".

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above. Examples include, but are not limited to, [3-(4-hydroxy)phenyl]propyl, [3-(1-methyl)(4-hydroxy)phenyl]propyl, (4-hydroxybenzyl)methyl, and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, and the like). Heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, piperazinyl, piperidinyl, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (R*N=wherein R* is a loweralkyl group), cycloalkyl, aryl, arylalkyl, and loweralkyl. In addition, nitrogen containing heterocycles can be N-protected.

The term "(heterocyclic)alkyl" as used herein refers to a heterocyclic group as defined above appended to a loweralkyl radical as defined above. The (heterocylic)alkyl group is attached to the parent moiety through an alkyl group wherein the alkyl group is of one to six carbon atoms. Examples include, but are not limited to, 2-pyridylmethyl, 4-pyridylmethyl, 2-pyridylethyl, 3-pyridylpropyl, 2-pyridylpropyl, 4-pyridylpropyl, 2-furylmethyl and the like.

The term "substituted (heterocyclic)alkyl" as used herein, refers to a heterocycloalkyl group, as defined above, wherein the heterocyclic group or the alkylgroup is substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, hydroxyalkyl, methoxymethoxy, amino, $C_1$-$C_3$-alkyl-amino, di($C_1$-$C_3$-alkyl)amino, carboxaldehydo, carboxy, alkoxycarbonyl, $C_1$-$C_3$-alkyl—CO—O—, $C_1$-$C_3$-alkyl—CO— NH—, or carboxamide. Example include, but are not limited to, 3-[(5-methyl)-2- pyridyl]propyl, 3-[(6-methyl)-2-pyridyl]propyl, 4-[(6-methyl)-2-pyridyl]butyl, (5-nitro)-2-thienylmethyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "substituted heteroaryl" as used herein refers to a heteroaryl group as defined herein substituted by independent replacement of one, two or three of the hydrogen atoms thereon with Cl, Br, F, I, OH, $C_1$–$C_3$-alkyl, $C_1$–$C_6$-alkoxy, methoxymethoxy, amino, or $C_1$–$C_3$-alkyl-amino, or may also refer to a mono-oxo substituted heteroaryl compound, such as 4-oxo-1H-quinoline, for example.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methyl-pyrrolidinone, ethers such as diethyl ether and bis-methoxymethyl ether, as well as various other compounds like dimethyl formamide, acetonitrile, acetone and ethyl acetate. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refer to esters which hydrolyze in vivo and include those that break down readily in the human body to leave the parent compound or a salt therof. Suitable ester groups include, for example, those derived from pharmaceutically acceptable aliphatic carboxylic acid, particularly alkonoic, alkenoic, cycoalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

PREFERRED EMBODIMENTS

The preferred compounds of the invention comprise those in which R is alkyl, alkenyl, cycloalkyl, heterocyclic, (heterocyclic)alkyl or alkylcycloalkyl; X and Y are independently chloro, fluoro, dioxalano, hydrogen, or alkoxy; A is —C, or N; $R_2$ and $R_3$ are hydrogen or cylopropyl and n is 1.

Representative compounds of the invention are selected from the group consisting of:

3'-N-desmethyl-3'-N-cyclopentyl-11-deoxy-11-[carboxy-(3,4-dichlorophenethylamino)]-6-O-methyl-erythromycin A 11,12-(cyclic carbamate);

3'-N-desmethyl-3'-N-cyclopropyl-11-deoxy-11-[carboxy-(3,4-dichlorophenethylamino)]-6-O-methyl-erythromycin A 11,12-(cyclic carbamate);

3'-N-desmethyl-3'-N-n-propyl-11-deoxy-11-[carboxy-(3,4-dichlorophenethylamino)]-6-O-methyl-erythromycin A 11,12-(cyclic carbamate);

3'-N-desmethyl-3'-N-cyclobutyl-11-deoxy-11-[carboxy-(3,4-dichlorophenethylamino)]-6-O-methyl-erythromycin A 11,12-(cyclic carbamate);

3'-N-desmethyl-3'-N-cyclohexyl-11-deoxy-11-[carboxy-(3,4-dichlorophenethylamino)]-6-O-methyl-erythromycin A 11,12-(cyclic carbamate);

3'-N-desmethyl-3'-N-isovaleryl-11-deoxy-11-[carboxy-(3,4-dichlorophenethylamino)]-6-O-methyl-erythromycin A 11,12-(cyclic carbamate);

3'-N-desmethyl-3'-N-(3-methylthiopropyl)-11-deoxy-11-[carboxy-(3,4-dichlorophenethylamino)]-6-O-methyl-erythromycin A 11,12-(cyclic carbamate);

3'-N-desmethyl-3'-N-(3-tetrahydrothienyl)-11-deoxy-11-[carboxy-(3,4-dichlorophenethylamino)]-6-O-methyl-erythromycin A 11,12-(cyclic carbamate);

3'-N-desmethyl-3'-N-(3,4-dimethylcyclopentyl)-11-deoxy-11-[carboxy-(3,4-dichlorophenethylamino)]-6-O-methyl-erythromycin A 11,12-(cyclic carbamate);

3'-N-desmethyl-3'-N-isopropyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclobutyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclopentyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclohexyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-n-propyl-11-deoxy-11-[carboxy-(3,4-dioxolanophenethylamino)]-6-O-methyl-erythromycin A 11,12-(cyclic carbamate);

3'-N-desmethyl-3'-N-cyclopentyl-11-deoxy-11-[carboxy-(3,4-dioxolanophenethylamino)]-6-O-methyl-erythromycin A 11,12-(cyclic carbamate);

3'-N-desmethyl-3'-N-n-propyl-11-deoxy-11-[carboxy-(4-chloro-3-fluorophenethylamino)]-6-O-methyl-erythromycin A 11,12-(cyclic carbamate);

3'-N-desmethyl-3'-N-isopropyl-11-deoxy-11-[carboxy-(4-chloro-3-fluorophenethylamino)]-6-O-methyl-erythromycin A 11,12-(cyclic carbamate);

3'-N-desmethyl-3'-N-cyclopentyl-11-deoxy-11[carboxy-(4-chloro-3-fluorophenethylamino)]-6-O-methyl-erythromycin A 11,12-(cyclic carbamate);

3'-N-desmethyl-3'-N-cyclobutylmethyl-11-deoxy-11-[carboxy-(4-chlorophenethylamino)]-6-O-methyl-erythromycin A 11,12-(cyclic carbamate);

3'-N-desmethyl-3'-N-cyclobutylmethyl-11-deoxy-11-[carboxy-(4-chlorophenethylamino)]-6-O-methyl-erythromycin A 11,12-(cyclic carbamate);

3'-N-desmethyl-3'-N-ethyl-11-deoxy-11-[carboxy-(4-chlorophenethylamino)]-6-O-methyl-erythromycin A 11,12-(cyclic carbamate);

3'-N-desmethyl-3'-N-isopropyl-11-deoxy-11-[carboxy-(4-chlorophenethylamino)]-6-O-methyl-erythromycin A 11,12-(cyclic carbamate);

3'-N-desmethyl-3'-N-cyclopentyl-11-deoxy-11-[carboxy-(4-chlorophenethylamino)]-6-O-methyl-erythromycin A 11,12-(cyclic carbamate);

3'-N-desmethyl-3'-N-cyclopentyl-11-deoxy-11-[carboxy-(3-chlorophenethylamino)]-6-O-methyl-erythromycin A 11,12-(cyclic carbamate);

3'-N-desmethyl-3'-N-n-propyl-11-deoxy-11-[carboxy-(3-chlorophenethylamino)]-6-O-methyl-erythromycin A 11,12-(cyclic carbamate);

3'-N-desmethyl-3'-N-cyclopentyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(3-chloro-4-fluorophenethylamino)]-6-O-methyl-erythromycin A 11,12-(cyclic carbamate);

3'-N-desmethyl-3'-N-isopropyl-11-deoxy-11-[carboxy-(3-chloro-4-fluorophenethylamino)]-6-O-methyl-erythromycin A 11,12-(cyclic carbamate);

3'-N-desmethyl-3'-N-cyclopropylmethyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(3,4-difluorophenethylamino)]-6-O-methyl-erythromycin A 11,12-(cyclic carbamate);

3'-N-desmethyl-3'-N-cyclopentyl-11-deoxy-11-[carboxy-(3,4-difluorophenethylamino)]-6-O-methyl-erythromycin A 11,12-(cyclic carbamate);

3'-N-desmethyl-3'-N-n-propyl-11-deoxy-11-[carboxy-(3,4-difluorophenethylamino)]-6-O-methyl-erythromycin A 11,12-(cyclic carbamate);

3'-N-desmethyl-3'-N-cyclopropylmethyl-11-deoxy-11-[carboxy-(3,4-difluorophenethylamino)]-6-O-methyl-erythromycin A 11,12-(cyclic carbamate);

3'-N-desmethyl-3'-N-(4-pyridylmethyl)-11-deoxy-11-[carboxy-(4-chlorophenethylamino)]-6-O-methyl-erythromycin A 11,12-(cyclic carbamate);

3'-N-desmethyl-3'-N-(2-butyl)-11-deoxy-11-[carboxy-(4-chlorophenethylamino)]-6-O-methyl-erythromycin A 11,12-(cyclic carbamate);

3'-N-desmethyl-3'-N-(3-pentyl)-11-deoxy-11-[carboxy-(4-chlorophenethylamino)]-6-O-methyl-erythromycin A 11,12-(cyclic carbamate);

3'-N-desmethyl-3'-N-(cyclopropylmethyl)-11-deoxy-11-[carboxy-(4-chlorophenethylamino)]-6-O-methyl-erythromycin A 11,12-(cyclic carbamate);

3'-N-desmethyl-3'-N-(2-cyclopropylethyl)-11-deoxy-11-[carboxy-(4-chlorophenethylamino)]-6-O-methyl-erythromycin A 11,12-(cyclic carbamate);

3'-N-desmethyl-3'-N-propyl-11-deoxy-11-[carboxy-(4-methoxyphenethylamino)]-6-O-methyl-erythromycin A 11,12-(cyclic carbamate);

3'-N-desmethyl-3'-N-cyclopentyl-11-deoxy-11-[carboxy-(4-methoxyphenethylamino)]-6-O-methyl-erythromycin A 11,12-(cyclic carbamate);

3'-N-desmethyl-3'-N-propyl-11-deoxy-11-[carboxy-(3,4-dimethylphenethylamino)]-6-O-methyl-erythromycin A 11,12-(cyclic carbamate);

3'-N-desmethyl-3'-N-cyclopentyl-11-deoxy-11-[carboxy-(3-bromo-4-methoxyphenethylamino)]-6-O-methyl-erythromycin A 11,12-(cyclic carbamate);

3'-N-desmethyl-3'-N-propyl-11-deoxy-11-[carboxy-(3-bromo-4-methoxyphenethylamino)]-6-O-methyl-erythromycin A 11,12-(cyclic carbamate);

3'-N-desmethyl-3'-N-propyl-11-deoxy-11-[carboxy-(3-chloro-4-fluorophenethylamino)]-6-O-methyl-erythromycin A 11,12-(cyclic carbamate);

3'-N-desmethyl-3'-N-(2-furyl)methyl-11-deoxy-11-[carboxy-(3-chloro-4-fluorophenethylamino)]-6-O-methyl-erythromycin A 11,12-(cyclic carbamate);

3'-N-desmethyl-3'-N-[2-(5-hydroxymethyl)furyl]methyl-11-deoxy-11-[carboxy-(3-chloro-4-fluorophenethylamino)]-6-O-methyl-erythromycin A 11,12-(cyclic carbamate);

3'-N-desmethyl-3'-N-(2-pyridyl)methyl-11-deoxy-11-[carboxy-(3-chloro-4-fluorophenethylamino)]-6-O-methyl-erythromycin A 11,12-(cyclic carbamate);

3'-N-desmethyl-3'-N-[2-(6-methyl)pyridyl]methyl-11-deoxy-11-[carboxy-(3-chloro-4-fluorophenethylamino)]-6-O-methyl-erythromycin A 11,12-(cyclic carbamate);

3'-N-desmethyl-3'-N-(4-hydroxyethoxybenzyl)-11-deoxy-11-[carboxy-(3-chloro-4-fluorophenethylamino)]-6-O-methyl-erythromycin A 11,12-(cyclic carbamate);

3'-N-desmethyl-3'-N-(3-methylthio)butyl-11-deoxy-11-[carboxy-(3-chloro-4-fluorophenethylamino)]-6-O-methyl-erythromycin A 11,12-(cyclic carbamate);

3'-N-desmethyl-3'-N-(4,4,4-trifluorobutyl)-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(4-chloro-3-fluorophenethylamino)]-6-O-methyl-erythromycin A 11,12-(cyclic carbamate);

3'-N-desmethyl-3'-N-isopropyl-11-deoxy-11-[carboxy-(3,4-difluorophenethylamino)]-6-O-methyl-erythromycin A 11,12-(cyclic carbamate);

3'-N-desmethyl-3'-N-propyl-11-deoxy-11-[carboxy-[3,4-(1,4-dioxano)phenethylamino)]}-6-O-methyl-erythromycin A 11,12-(cyclic carbamate);

3'-N-desmethyl-3'-N-cyclopropylmethyl-11-deoxy-11-[carboxy-(3,4-dichlorophenethylamino)]-6-O-methyl-erythromycin A 11,12-(cyclic carbamate);

3'-N-desmethyl-3'-N-[3-(methylsulfoxy)propyl]-11-deoxy-11-[carboxy-(3,4-dichlorophenethylamino)]-6-O-methyl-erythromycin A 11,12-(cyclic carbamate);

3'-N-desmethyl-3'-N-ethylthiourea-11-deoxy-11-[carboxy-(3,4-dichlorophenethylamino)]-6-O-methyl-erythromycin A 11,12-(cyclic carbamate);

3'-N-desmethyl-3'-N-[2-(5-hydroxymethyl)furyl]methyl-11-deoxy-11-[carboxy-(3,4-dichlorophenethylamino)]-6-O-methyl-erythromycin A 11,12-(cyclic carbamate);

3'-N-desmethyl-3'-N-cyclopropylmethyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-propyl-11-deoxy-11-[carboxy-(4-chloroanilinoethylamino)]-6-O-methyl-erythromycin A 11,12-(cyclic carbamate);

3'-N-desmethyl-3'-N-cyclopentyl-11-deoxy-11-[carboxy-(4-chloroanilinoethylamino)]-6-O-methyl-erythromycin A 11,12-(cyclic carbamate);

3'-N-desmethyl-3'-N-isopropyl-11-deoxy-11-[carboxy-(3,4-diflorophenethylamino)]-6-O-methyl-erythromycin A 11,12-(cyclic carbamate);

3'-N-desmethyl-3'-N-(2-imidazolo)methyl-11-deoxy-11-[carboxy-(3,4-dichlorophenethylamino)]-6-O-methyl-erythromycin A 11,12-(cyclic carbamate);

3'-N-desmethyl-3'-N-(3-pyridyl)methyl-11-deoxy-11-[carboxy-(3,4-dichlorophenethylamino)]-6-O-methyl-erythromycin A 11,12-(cyclic carbamate);

3'-N-desmethyl-3'-N-(2-pyridyl)methyl-11-deoxy-11-[carboxy-(3,4-dichlorophenethylamino)]-6-O-methyl-erythromycin A 11,12-(cyclic carbamate);

3'-N-desmethyl-3'-N-[(5-nitro)-2-thienyl]methyl-11-deoxy-11-[carboxy-(3,4-dichlorophenethylamino)]-6-O-methyl-erythromycin A 11,12-(cyclic carbamate);

3'-N-desmethyl-3'-N-[5-(4-chlorophenyl)-2-furyl]methyl-11-deoxy-11-[carboxy-(3,4-dichlorophenethylamino)]-6-O-methyl-erythromycin A 11,12-(cyclic carbamate);

3'-N-desmethyl-3'-N-[5-nitro-2-furyl]methyl-11-deoxy-11-[carboxy-(3,4-dichlorophenethylamino)]-6-O-methyl-erythromycin A 11,12-(cyclic carbamate);

3'-N-desmethyl-3'-N-[2,5-dimethoxy-3-tetrahydrofuryl]methyl-11-deoxy-11-[carboxy-(3,4-dichlorophenethylamino)]-6-O-methyl-erythromycin A 11,12-(cyclic carbamate);

3'-N-desmethyl-3'-N-[6-methyl-2-pyridyl]methyl-11-deoxy-11-[carboxy-(3,4-dichlorophenethylamino)]-6-O-methyl-erythromycin A 11,12-(cyclic carbamate);

3'-N-desmethyl-3'-N-(4,4,4-trifluorobutyl)-11-deoxy-11-[carboxy-(3,4-dichlorophenethylamino)]-6-O-methyl-erythromycin A 11,12-(cyclic carbamate);

3'-N-desmethyl-3'-N-(1-bromo-2-napthyl)methyl-11-deoxy-11-[carboxy-(3,4-dichlorophenethylamino)]-6-O-methyl-erythromycin A 11,12-(cyclic carbamate);

3'-N-desmethyl-3'-N-(4-methyl-1-napthyl)methyl-11-deoxy-11-[carboxy-(3,4-dichlorophenethylamino)]-6-O-methyl-erythromycin A 11,12-(cyclic carbamate);

3'-N-desmethyl-3'-N-(4-dimethylamino-1-napthyl)methyl-11-deoxy-11-[carboxy-(3,4-dichlorophenethylamino)]-6-O-methyl-erythromycin A 11,12-(cyclic carbamate);

3'-N-desmethyl-3'-N-(2-furyl)methyl-11-deoxy-11-[carboxy-(3,4-dichlorophenethylamino)]-6-O-methyl-erythromycin A 11,12-(cyclic carbamate);

3'-N-desmethyl-3'-N-[3-(4-pyridyl)propyl]-11-deoxy-11-[carboxy-(3,4-dichlorophenethylamino)]-6-O-methyl-erythromycin A 11,12-(cyclic carbamate);

3'-N-desmethyl-3'-N-[3-(2-pyridyl)propyl]-11-deoxy-11-[carboxy-(3,4-dichlorophenethylamino)]-6-O-methyl-erythromycin A 11,12-(cyclic carbamate);

3'-N-desmethyl-3'-N-3-[4-(4-pyridyl)butyl]-11-deoxy-11-[carboxy-(3,4-dichlorophenethylamino)]-6-O-methyl-erythromycin A 11,12-(cyclic carbamate);

3'-N-desmethyl-3'-N-[3-(3-pyridyl)propyl]-11-deoxy-11-[carboxy-(3,4-dichlorophenethylamino)]-6-O-methyl-erythromycin A 11,12-(cyclic carbamate);

3'-N-desmethyl-3'-N-[(3-(3-pyridyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-[3-(4-pyridyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-[3-(2-pyridyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-[4-(4-pyridyl)butyl]-11-deoxy-11-[carboxy-(3-chloro-4-fluorophenethylamino)]-6-O-methyl-erythromycin A 11,12-(cyclic carbamate);

3'-N-desmethyl-3'-N-[4-(6-methyl-2-pyridyl)]butyl-11-deoxy-11-[carboxy-(3-chloro-4-fluorophenethylamino)]-6-O-methyl-erythromycin A 11,12-(cyclic carbamate);

3'-N-desmethyl-3'-N-[1-methyl-3-(4-hydroxyphenyl)propyl]-11-deoxy-11-[carboxy-(3,4-dichlorophenethylamino)]-6-O-methyl-erythromycin A 11,12-(cyclic carbamate);

3'-N-desmethyl-3'-N-[(1methyl)-3-(4-hydroxyphenyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-[3-(6-methyl-2-pyridyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-[3-(5-methyl-2-pyridyl)propyl]-11-deoxy-11-[carboxy-(3-chloro-4-fluorophenethylamino)]-6-O-methyl-erythromycin A 11,12-(cyclic carbamate);

3'-N-desmethyl-3'-N-(2-pyridylethyl)-11-deoxy-11-[carboxy-(3,4-dichlorophenethylamino)]-6-O-methyl-erythromycin A 11,12-(cyclic carbamate);

3'-N-desmethyl-3'-N-(2-pyridylethyl)-11-deoxy-11-[carboxy-(3-chloro-4-fluorophenethylamino)]-6-O-methyl-erythromycin A 11,12-(cyclic carbamate);

3'-N-desmethyl-3'-N-(4-hydroxybenzyl)-11-deoxy-11-[carboxy-(3,4-dichlorophenethylamino)]-6-O-methyl-erythromycin A 11,12-(cyclic carbamate);

3'-N-desmethyl-3'-N-(4-pyridyl)methyl-11-deoxy-11-[carboxy-(3,4-dichlorophenethylamino)]-6-O-methyl-erythromycin A 11,12-(cyclic carbamate);

3'-N-desmethyl-3'-N-[(3-methylthio)butyl]-11-deoxy-11-[carboxy-(3,4-dichlorophenethylamino)]-6-O-methyl-erythromycin A 11,12-(cyclic carbamate);

3'-N-desmethyl-3'-N-(1-methylcyclopropyl)methyl-11-deoxy-11-[carboxy-(3,4-dichlorophenethylamino)]-6-O-methyl-erythromycin A 11,12-(cyclic carbamate);

3'-N-desmethyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3'-N-desmethyl-3'-N-oxiranylmethyl-11-deoxy-11-[carboxy-(3,4-dichlorophenethylamino)]-6-O-methyl-erythromycin A 11,12-(cyclic carbamate);

3'-N-desmethyl-3'-guanidino-11-deoxy-11-[carboxy-(3,4-dichlorophenethylamino)]-6-O-methyl-erythromycin A 11,12-(cyclic carbamate); and 3'-N-desmethyl-3'-N-2-(4,5-dihydroimidazole)-11-deoxy-11-[carboxy-(3,4-dichlorophenethylamino)]-6-O-methyl-erythromycin A 11,12-(cyclic carbamate).

The more preferred compounds are selected from the group consisting of:

3'-N-desmethyl-3'-N-cyclopentyl-11-deoxy-11-[carboxy-(3,4-dichlorophenethylamino)]-6-O-methyl-erythromycin A 11,12-(cyclic carbamate);

3'-N-desmethyl-3'-N-cyclopropyl-11-deoxy-11-[carboxy-(3,4-dichlorophenethylamino)]-6-O-methyl-erythromycin A 11,12-(cyclic carbamate);

3'-N-desmethyl-3'-N-n-propyl-11-deoxy-11-[carboxy-(3,4-dichlorophenethylamino)]-6-O-methyl-erythromycin A 11,12-(cyclic carbamate);

3'-N-desmethyl-3'-N-isopropyl-11-deoxy-11-[carboxy-(3-chloro-4-fluorophenethylamino)]-6-O-methyl-erythromycin A 11,12-(cyclic carbamate);

3'-N-desmethyl-3'-N-cyclopropylmethyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(3,4-difluorophenethylamino)]-6-O-methyl-erythromycin A 11,12-(cyclic carbamate);

3'-N-desmethyl-3'-N-cyclopentyl-11-deoxy-11-[carboxy-(3,4-difluorophenethylamino)]-6-O-methyl-erythromycin A 11,12-(cyclic carbamate);

3'-N-desmethyl-3'-N-n-propyl-11-deoxy-11-[carboxy-(3,4-difluorophenethylamino)]-6-O-methyl-erythromycin A 11,12-(cyclic carbamate); and 3'-N-desmethyl-3'-N-cyclopropylmethyl-11-deoxy-11-[carboxy-(3,4-difluorophenethylamino)]-6-O-methyl-erythromycin A 11,12-(cyclic carbamate).

Effect and Utilities of LHRH Agonists and Antagonists

The LHRH agonist and antagonist compounds of the invention are useful for treatment of precocious puberty, prostate cancer, benign prostatic hyperplasia (BPH), endometriosis, uterine fibroids, breast cancer, acne, premenstrual syndrome, polycystic ovary syndrome and diseases which result from excesses or deficiencies in gonadal hormone production in either sex of humans and animals. The LHRH antagonists of the invention are also useful for controlling reproduction in both female and males. Compounds of the invention are useful for suppressing levels of testosterone and dihydrotestosterone (DHT) in male and estrogen and estradiol in female.

In the practice of the method of this invention an effective amount of a compound of the invention or a pharmaceutical composition containing the same is administered to the human or animal in need of, or desiring, such treatment.

These compounds or compositions may be administered by any variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 1 and 200 mg/kg body weight per day, preferably between 1 and 30 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of afflication or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a poly valent metal cation such as zinc, calcium, bismuth, barium, magnesium, aluminum, copper, cobalt, nickel, cadmium and the like, or with an organic cation formed from e.g., N,N'-debenzylethylenediamine or ethylenediamine; or (c) combinations of (a) and (b) e.g., a zinc tannate salt. Additionally, the compounds of the present invention or preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

LHRH Antagonist Activity

Representative compounds of the present invention were evaluated in in vitro tests for LHRH rat pituitary receptor binding ($pK_I$) and for LH inhibition from rat pituitary cells for antagonist potency ($pA_2$). The tests employed the methods detailed in F. Haviv, et al. *J. Med. Chem.*, 32: 2340–2344 (1989). The receptor binding affinity ($pK_I$) is the negative logarithm of the equilibrium dissociation constants. The results of the $pK_I$ for representative compounds of this invention are presented in Table 1.

TABLE 1

| Example | $pK_I$ | Example | $pK_I$ | Example | $pK_I$ |
|---------|------|---------|------|---------|------|
| 1 | 9.09 | 33 | 9.17 | 65 | 8.13 |
| 2 | 9.24 | 34 | 8.00 | 66 | 8.86 |
| 3 | 9.13 | 35 | 8.12 | 67 | 8.11 |
| 4 | 8.49 | 36 | 8.04 | 68 | 8.29 |
| 5 | 8.44 | 37 | 8.04 | 69 | 8.21 |
| 6 | 8.09 | 38 | 8.17 | 70 | 8.23 |
| 7 | 8.33 | 39 | 8.29 | 71 | 8.21 |
| 8 | 8.13 | 40 | 8.24 | 72 | 9.17 |
| 9 | 8.36 | 41 | 8.07 | 73 | 9.67 |
| 10 | 8.76 | 42 | 8.14 | 74 | 8.50 |
| 11 | 8.51 | 43 | 8.45 | 75 | 8.90 |
| 12 | 8.68 | 44 | 8.84 | 76 | 8.04 |
| 13 | 8.10 | 45 | 8.45 | 77 | 8.21 |
| 14 | 8.75 | 46 | 8.94 | 78 | 8.10 |
| 15 | 8.20 | 47 | 8.60 | 79 | 8.11 |
| 16 | 8.40 | 48 | 8.72 | 80 | 8.40 |
| 17 | 8.37 | 49 | 8.50 | 81 | 8.36 |
| 18 | 8.23 | 50 | 9.01 | 82 | 8.64 |
| 19 | 8.80 | 51 | 8.20 | 83 | 8.46 |
| 20 | 8.49 | 52 | 8.10 | 84 | 8.15 |
| 21 | 8.21 | 53 | 8.52 | 85 | 8.23 |
| 22 | 8.35 | 54 | 8.39 | 86 | 8.75 |
| 23 | 8.17 | 55 | 8.14 | 87 | 8.65 |
| 24 | 8.56 | 56 | 8.75 | 88 | 8.68 |
| 25 | 8.38 | 57 | 8.04 | 89 | 8.38 |
| 26 | 8.83 | 58 | 8.81 | 90 | 8.39 |
| 27 | 8.81 | 59 | 8.43 | 91 | 8.02 |
| 28 | 9.49 | 60 | 8.57 | 92 | 8.20 |
| 29 | 9.27 | 61 | 8.57 | 93 | 8.30 |
| 30 | 9.29 | 62 | 8.52 | | |

TABLE 1-continued

| Example | $pK_I$ | Example | $pK_I$ | Example | $pK_I$ |
|---------|------|---------|------|---------|------|
| 31 | 9.57 | 63 | 8.13 | | |
| 32 | 10.08 | 64 | 8.16 | | |

The $pA_2$ value is the negative logarithm of the concentration of antagonist which shifts the response curve produced by the agonist leuprolide to two-fold higher concentration. Leuprolide is the LHRH agonist having the structure pyro-Glu$^1$-His$^2$-Trp$^3$-Ser$^4$-Tyr$^5$-D-Leu$^6$-Leu$^7$-Arg$^8$-Pro$^9$-NHEt and is disclosed and claimed in U.S. Pat. No. 4,005,063. Typically $pA_2$ values of 7.0 or greater are indicative of good LHRH antagonist potency. The $pA_2$ values for representative compounds are set forth in Table 2 below.

| Example | $pA_2$ | Example | $pA_2$ |
|---------|------|---------|------|
| 1 | 9.10 | 26 | 8.66 |
| 3 | 8.60 | 27 | 8.42 |
| 16 | 7.49 | 28 | 8.52 |
| 20 | 7.53 | 29 | 8.97 |
| 21 | 7.26 | 30 | 8.28 |
| 22 | 7.52 | 31 | 8.24 |
| 23 | 7.30 | 32 | 7.58 |
| 25 | 7.43 | 33 | 8.40 |

Synthetic Methods

The compounds and processes of the present invention will be better understood in connection with the following synthetic Schemes 1 and 2 which illustrate the methods by which the compounds of the invention may be prepared. The compounds are prepared by utilizing commercially available or synthesized reagents.

Abbreviations

Abbreviations which have been used in the descriptions of the scheme and the examples that follow are: Ac for acetyl; APCI for atmospheric pressure chemical ionization; CDI for carbonyldiimidazide; $CH_3CN$ for acetonitrile; CI or DCI for desorption chemical ionization; DMF for dimethyl formamide; ESI for electrospray ionization; EtOAc for ethyl acetate; FAB for fast atom bombardment; FTIR for Fourier transform infrared spectroscopy; HPLC for high performance liquid chromatography; IR for infrared spectroscopy; MeOH for methanol; MHz for megahertz; MIC for microscope; MS for mass spectra; NaHMDS for sodium hexamethyldisilazide; NMR for nuclear magnetic resonance; $R_f$ for retention factor; $R_t$ for retention time; TBAF for tetrabutylammonium fluoride; THF for tetrahydrofuran; TLC for thin layer chromatography; TMS for trimethylsilyl; TMS Cl for trimethylsilyl chloride; and DCM for dichloromethane.

The starting material 6-O-methyl-erythromycin A 1 (clarithromycin, commercially available as BIAXIN® from Abbott Laboratories) is protected at the 2' and 4" positions by reaction with a suitable hydroxy protecting reagent, such as described by T. W. Greene and P. G. M. Wuts in *Protective Groups in Organic Synthesis*, 2nd. ed., John Wiley & Son, Inc. 1991. Hydroxy protecting reagents include, for example, acetic anhydride, benzoic anhydride, benzylchloroformate, hexamethyldisilazane, or trialkylsilyl chloride in an aprotic solvent.

Scheme 1
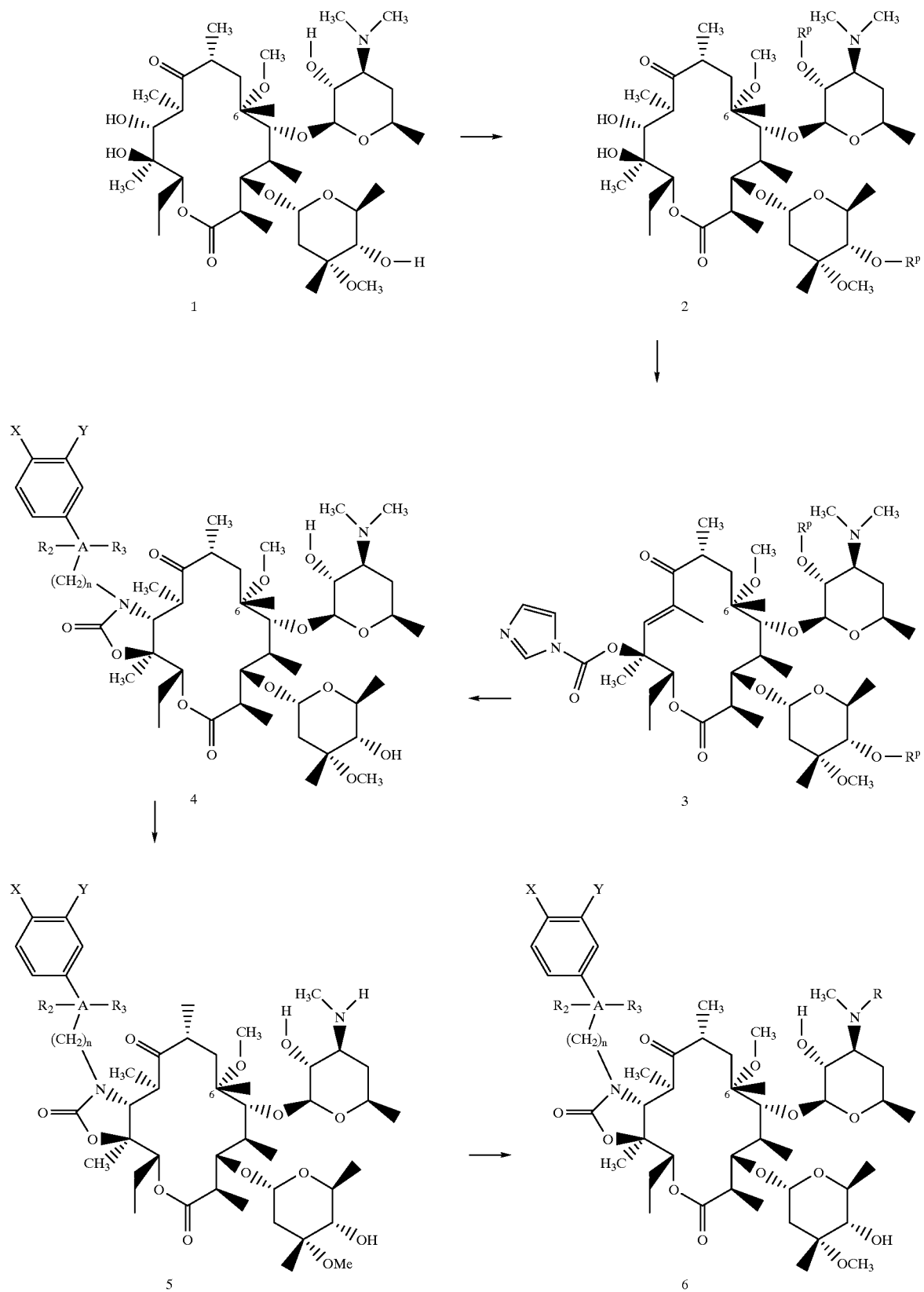

Protection of 2'- and 4"-hydroxy groups of 6-O-methyl-erythromycin A 1 as shown in Scheme 1 may be accomplished sequentially or simultaneously to provide compound 2 where RP is a hydroxy protecting group. A preferred protecting group RP is trimethylsilyl or acetyl.

Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof.

The protected compound 2 is treated with sodium hexamethyldisilazide or sodium hydride in an aprotic solvent at 0–25° C. and carbonyldiimidazole to yield compound 3. Treatment of compound 3 with an amino compound of the formula

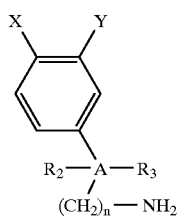

either without solvent or in acetonitrile at 25–80° C., followed by deprotection results in formation of N-substituted cyclic carbamate represented by compound 4. Deprotection of the 2'- and 4"-hydroxy protecting groups to obtain compound 4 is carried out by the methods described by T. W. Greene and P. G. M. Wuts in *Protective Groups in Organic Synthesis*, 2nd. ed., John Wiley & Son, Inc. 1991.

The desmethylation of the 3'-N-dimethyl group is accomplished by treating compound 4 with iodine in the presence of a suitable base, such as sodium acetate and a light or a heat source, followed by quench with sodium thiosulfate and work up to afford compound 5. N-dealkylation can also be accomplished utilizing chloroformate reagents such as benzyl chloroformate, allyl chloroformate, vinyl chloroformate and the like.

Alkylation of 3'-N-desmethyl compound 5 is achieved by reaction with an appropriate aldehyde or ketone in the presence of a hydride metal such as sodium cyanoborohydride or sodium triacetoxyborohydride or in the presence of Pd/C catalyst in a protic or non-protic solvent under hydrogen atmosphere. The aldehydes and ketones that may be used in preparing compound 5 include, for example, cyclopropyl carboxaldehyde, acetone, n-propanal, cyclohexanone, cyclopentanone, isovaleraldehyde, cyclobutanone, isopropylaldehyde, 2'-pyridine-carboxyaldehyde, 4-thiazole-carboxyaldehyde.

Alkylation of 3'-N-desmethyl compound 5 can also be achieved by the reaction with an appropriate alkylating agent in the presence of a base by the methods known in the art to afford compound 6. The alkylating agents which may be used in preparing compound 5 include loweralkyl halides such as ethyl bromide, halo-substituted loweralkyl halides, cyano-substituted loweralkyl halides, hydroxy-substituted loweralkyl halides, other loweralkenyl halides such as methylallyl chloride, loweralkynyl halides such as propargyl bromide, lower cycloalkyl halides, lower cycloalkylmethyl halides such as lower cyclopropylmethyl and benzyl halides.

Scheme 2 illustrates a specific embodiment of Example 1 which involves treatment of 2'-acetyl-6-O-methyl erythromycin A 7 with trimethylsilyl chloride to afford compound 8. Compound 8 is treated with sodium hexamethyldisilazide and carbonyldiimidazole to yield the 12-O-acylimidazole derivative, which is subsequently reacted with 3,4-dichlorophenethyl amine to form the 11,12-cyclic carbamate derivative. The 11,12 cyclic carbamate so obtained is treated with methanol to give compound 9. Deprotection of the 4"-protected hydroxy group is achieved by methods known in the art to yield compound 10. Treatment of compound 10 with iodine in the presence of sodium acetate followed by quenching the reaction mixture with sodium bisulfite affords compound 11. The alkylation of the 3'-nitrogen is achieved by reaction with cyclopentanone in the presence of sodium cyanoborohydride in methanol and a few drops of acetic acid to afford the final product, compound 12.

Scheme 2

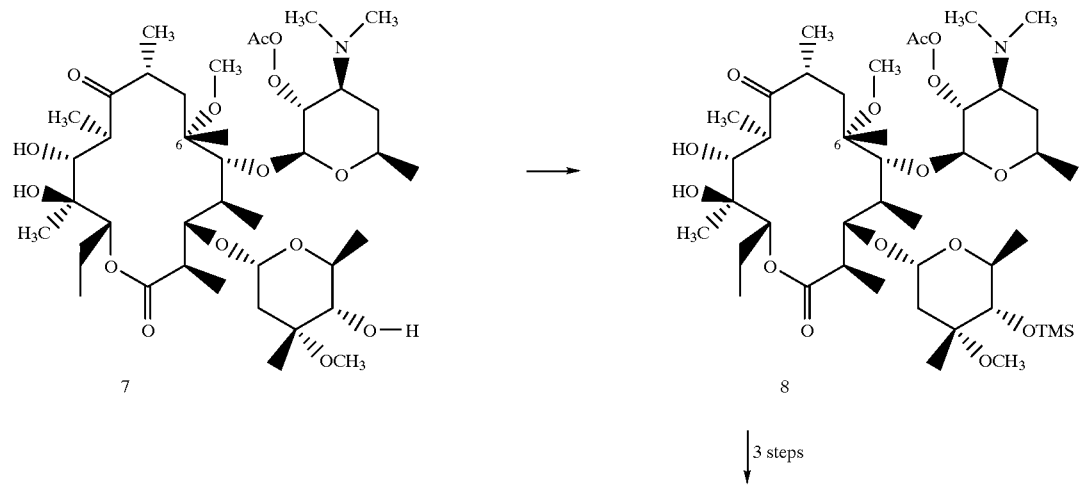

-continued

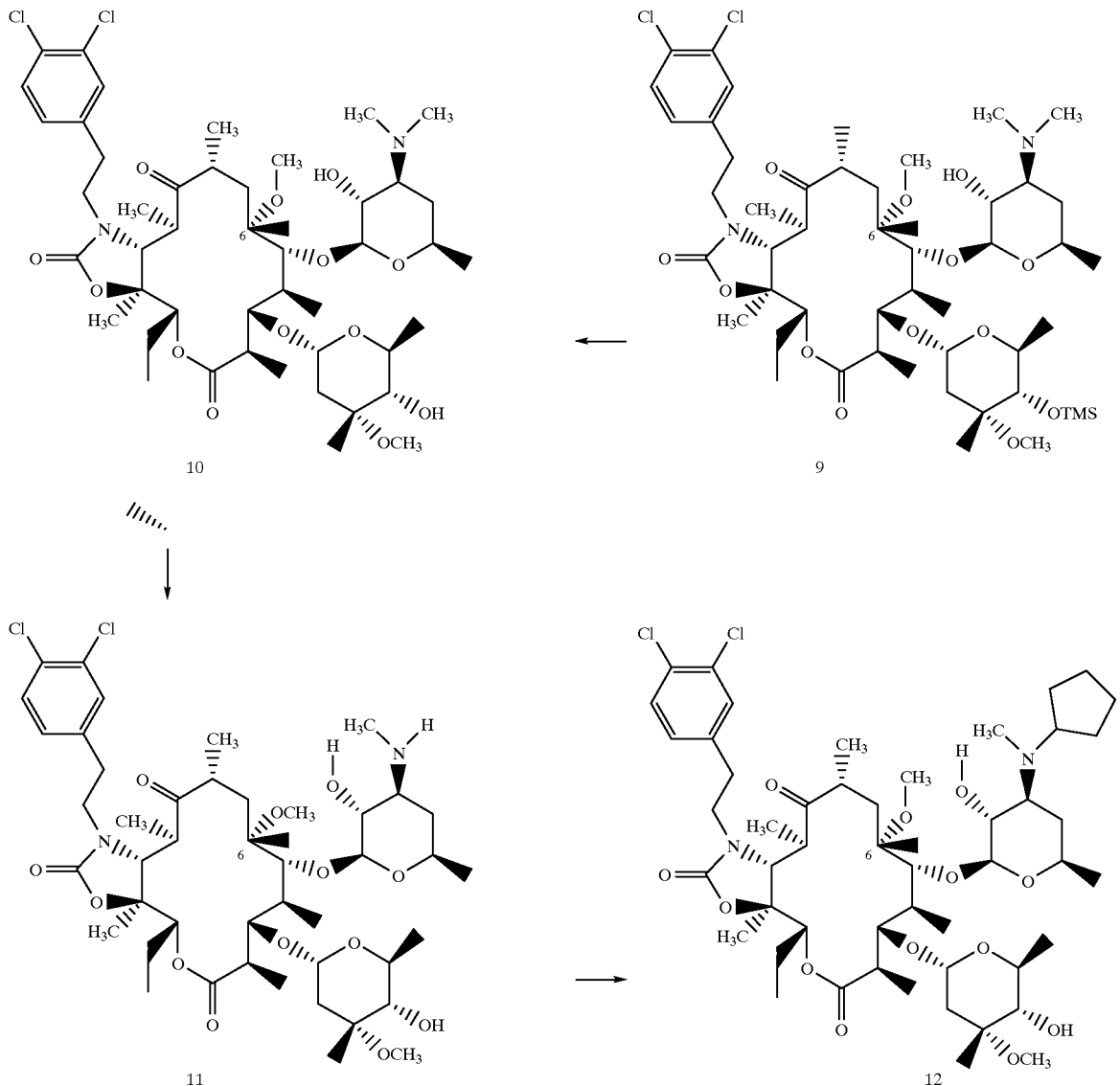

The foregoing may be better understood by reference to the following examples which are presented for illustration and not to limit the scope of the inventive concept.

EXAMPLES

EXAMPLE 1

3'-N-Desmethyl-3'-N-cyclopentyl-11-deoxy-11-[carboxy-(3,4-dichlorophenethylamino)]-6-O-methyl-erythromycin A 11,12-(cyclic carbamate) (Compound 12, Scheme 2)

6-O-methyl erythromycin (commercially available from Abbott Laboratories as BIAXIN® was protected at the 2'-position with acetyl protecting group by the methods described in the literature.

Step 1: 2'-O-Acetyl-4"-O-trimethylsilyl-6-O-methyl-erythromycin A (Compound 8, Scheme 2)

2'-O-Acetyl-6-O-methyl-erythromycin A (45 g, 57 mmol) was dissolved in 450 mL of $CH_2Cl_2$ and cooled to 0° C. in an ice/water bath. Pyridine (13.8 mL, 171 mmol) was added in one portion followed by the dropwise addition of TMS-Cl (14.5 mL, 114 mmol) over a 15 min period. The reaction was stirred for 1 h under the protection of a drying tube, afterwhich TLC ($CH_2Cl_2$:MeOH, 9:1) indicated complete conversion to a new, less polar material. The reaction was then quenched with 500 mL of 0.5 M $NaH_2PO_4$, the organic layer separated and washed with $H_2O$ (300 mL), $NaHCO_3$ (sat.) (300 mL), $H_2O$ (300 mL), and brine (100 mL), prior to drying ($Na_2SO_4$), filtering and concentrating. The residue was crystallized from $CH_3CN$ to yield 48 g of 8 (98%); mp 235–237° C. ($CH_3CN$); $R_f$=0.5 ($CH_2Cl_2$:MeOH, 9:1); MS ESI (M+H)$^+$ at m/z 862; $^{13}C$ NMR (75 MHz, $CDCl_3$) d 221.0, 175.6, 169.9, 100.0, 96.0, 80.5, 80.3, 78.3, 77.8, 76.4, 74.1, 73.2, 72.0, 69.0, 67.1, 65.2, 62.7, 50.3, 49.4, 45.1, 44.9, 40.5, 38.7, 38.6, 37.1, 35.6, 30.9, 22.1, 21.5, 21.4, 20.9, 19.7, 19.2, 17.8, 15.9, 15.8, 12.1, 10.4, 8.9, 0.8.

Step 2: 4"-O-Trimethylsilyl-11-deoxy-11-[carboxy-(3,4-dichlorophenethylamino)]-6-O-methyl-erythromycin A 11,12-(cyclic carbamate) (Compound 9, Scheme 2)

Compound 8 from Step 1 (20.4 g, 24.2 mmol) was dissolved in 20 mL of anhydrous THF then diluted with 200 mL of DMF. The resulting solution was cooled in an ice/water bath and treated with 1,1'-carbonyldiimidazole (19.6 g, 120.9 mmol) in one portion followed by the portionwise addition of 1.45 g (36 mmol) NaH (60% oil suspension). The reaction was allowed to warm to ambient temperature and was stirred under $N_2$ for 1 h after which TLC [EtOAc:MeOH, 95:5, Ce (IV) visualization] indicated complete conversion to a more polar material. The reaction was carefully quenched with water and then partitioned between EtOAc (400 mL) and water (300 mL). The organic phase was collected and washed with 1 N NaOH (300 mL), water (2×300 mL), and brine (200 mL) prior to drying ($Na_2SO_4$) and concentration. A sample of the resulting colorless foam was submitted for MS analysis which showed $(M+H)^+$ @m/z 938 for the desired acyl imidosole intermediate. The material was dissolved in $CH_3CN$ (25 mL), treated with 7.0 g (36 mmol) of 3,4-dichlorophenethylamine and stirred under $N_2$ at 55° C. After 48 h TLC [EtOAc:MeOH, 95:5, Ce (IV) visualization] indicated complete conversion of the starting compound to a less polar material which precipitated upon cooling to ambient temperature. The resulting precipitate was recrystallized from $CH_3CN$ to yield 16.1 g of 2',4"-protected cyclic carbamate as colorless needles. This protected cyclic carbamate (16.1 g, 15.2 mmol) was suspended in 250 mL of methanol and the suspension heated to 55° C. under the protection of a drying tube. After 24 h TLC [$CH_2Cl_2$:MeOH, 9:1, Ce (IV) visualization] indicated complete conversion of the starting acyl imidosole intermediate to a new more polar material which precipitated upon cooling to ambient temperature. The resulting solid was crystallized from MeOH/water to yield 13 g of compound 9. mp 112–114° C.; $R_f$=0.65 ($CH_2Cl_2$:MeOH, 9:1); MS (ESI) $(M+H)^+$ at m/z 1017; HRMS m/z $(M+H)^+$ calcd 999.5116, obsd 999.5110; $^1$H NMR (300 MHz, $CDCl_3$) δ 7.46 (d, J=2 Hz, Ar H), 7.35 (d, J=8 Hz, Ar H), 7.19 (dd, J=8, 2 Hz, Ar H), 4.91 (d, J=4.4 Hz, 1 H), 4.56 (d, J=7 Hz, 1 H, C-1' CH), 3.75 (d, J=10 Hz, 1 H, C-3 CH), 3.70 (s, 1 H, C-11 CH), 3.67 (d, J=8 Hz, 1 H, C-5 CH), 3.31 (s, 3 H, C-6 $OCH_3$), 3.07 (s, 3 H, C-6 $OCH_3$), 2.38 (d, J=15 Hz, 1 H, C-2" CH), 2.28 (s, 6 H, C-2' $N(CH_3)_2$), 1.43 (s, 3 H, C-6 $CH_3$), 1.40 (s, 3 H, C-12 $CH_3$), 1.07 (d, J=23 Hz, 3 H, C-10 $CH_3$), 0.82 (t, J=7 Hz, 3 H, C-15$CH_3$), 0.16 (s, 9 H, C-4" $OSi(CH_3)_3$); $^{13}$C NMR (75 MHz, $CDCl_3$) δ 216.1, 176.5, 157.2, 139.3, 132.1, 131.0, 130.2, 130.0, 128.4, 102.4, 96.6, 82.8, 80.6, 79.9, 79.0, 78.0, 76.1, 73.1, 71.1, 68.0, 65.2, 64.7, 60.3, 50.6, 49.6, 45.5, 45.3, 44.8, 40.0 (2C), 39.1, 38.9, 35.6, 32.6, 28.6, 22.1, 21.8, 21.7, 20.1, 19.2, 18.8, 16.0, 14.1, 14.0, 10.2, 9.0, 0.8.

Step 3: 11-Deoxy-11-[carboxy-(3,4-dichlorophenethylamino)]-6-O-methyl-erythromycin A 11,12-(cyclic carbamate) (Compound 10, Scheme 2)

The compound 2 from the above step (2.51 g, 2.46 mmol) was dissolved in 20 mL of THF, treated with 2.6 mL of TBAF (1 M/THF, 2.6 mmol), and stirred at ambient temperature. After 9 h TLC [$CHCl_3$:MeOH:$NH_4OH$, 90:8:1, Ce (IV) visualization] indicated complete conversion of the starting material to a new more polar material. The reaction mixture was partitioned between EtOAc (300 mL) and water (300 mL). The organic phase was washed with $NaHCO_3$ (sat., 200 mL), water (200 mL), and brine (200 mL) prior to drying ($Na_2SO_4$) and concentrating. The resulting residue crystallized from $CH_3CN$ to yield 1.5 g of product (64%): mp 240–243° C.; $R_f$=0.45 ($CHCl_3$:MeOH:$NH_4OH$, 90:8:1); MS (FAB) $(M+H)^+$ at m/z 945; $^1$H NMR (300 MHz, $CDCl_3$) δ 7.45 (d, J=2 Hz, 1 H, Ar H), 7.35 (d, J=8 Hz, 1 H, Ar H), 7.19 (dd, J=8, 2 Hz, 1 H, Ar H), 4.44 (d, J=7 Hz, 1 H, C-1' CH), 3.75 (d, J=10 Hz, 1 H, C-3 CH), 3.69 (s, 1 H, C-11 CH), 3.33 (s, 3 H, C-3" $OCH_3$), 3.07 (s, 3 H, C-6 $OCH_3$), 2.29 (s, 6 H, C-3' $N(CH_3)_2$), 2.19 (d, J=10 Hz, 1 H, C-4" OH), 1.44 (s, 3 H, C-6 $CH_3$), 1.40 (s, 3 H, C-12 $CH_3$), 1.31 (d, J=6 Hz, 3 H, C-6" $CH_3$), 1.26 (s, 3 H, C-3" $CH_3$), 1.15 (d, J=7 Hz, 3 H, C-8 $CH_3$), 1.12 (d, J=8 Hz, 3 H, C-4 $CH_3$), 1.02 (d, J=7 Hz, 3 H, C-10 $CH_3$), 0.83 (t, J=8 Hz, 3 H, C-15 $CH_3$); $^{13}$C NMR (75 MHz, $CDCl_3$) δ 216.2, 176.4, 157.2, 139.3, 132.1, 131.0, 130.2, 130.1, 128.4, 102.9, 96.2, 82.8, 80.1, 78.9, 77.9, 77.8, 76.2, 72.6, 70.9, 68.9, 65.8, 65.6, 60.3, 50.6, 49.5, 45.5, 45.3, 44.8, 40.2 (2C), 39.0, 38.9, 34.8, 32.6, 28.5, 21.9, 21.5 (2C), 20.2, 18.9, 18.7, 16.0, 14.2, 14.1, 10.2, 9.0; IR (KBr) ν 3430, 2970, 2940, 1760, 1735, 1710, 1460, 1420, 1380, 1235, 1170, 1070, 1055, 1010, 1000 $cm^{-1}$; Anal. Calcd for $C_{47}H_{74}Cl_2N_2O_{13}$·0.5 $H_2O$: C, 59.11; H, 7.91; N, 2.93. Found: C, 59.13; H, 8.12; N, 2.89.

Step 4: 3'-N-Desmethyl-11-deoxy-11-[carboxy-(3,4-dichlorophenethylamino)]-6-O-methyl-erythromycin A 11,12-(cyclic carbamate) (Compound 11, Scheme 2)

2.5 g of the compound from Step 3 (2.65 mmol) was dissolved in 50 mL of methanol and treated with 1.80 g of NaOAc·3 $H_2O$ (13.25 mmol) and 0.71 g of $I_2$ (2.78 mmol). The solution was irradiated with a 500W halogen work lamp and stirred at ambient temperature. After 2 h TLC indicated complete conversion of the starting compound to a new, more polar material. The excess $I_2$ was quenched by the dropwise addition of 1 M $Na_2S_2O_3$. The reaction mixture was concentrated and the resulting residue purified on a silica gel column (elution with $CHCl_3$:MeOH:$NH_4OH$, 90:8:1) to yield 1.75 g of compound 11. (71%) as an amorphous solid: mp 136–142° C. (acetonitrile/water); $R_f$=0.33 ($CHCl_3$:MeOH:$NH_4OH$, 90:8:1); MS (FAB) $(M+H)^+$ at m/z 931; $^1$H NMR (300 MHz, $CDCl_3$) δ 7.45 (d, J=2 Hz, 1 H, Ar H), 7.35 (d, J=8 Hz, 1 H, Ar H), 7.19 (dd, J=8, 2 Hz, 1 H, Ar H), 4.42 (d, J=7 Hz, 1 H, C-1' CH), 3.74 (d, J=9 Hz, 1 H, C-3 CH), 3.69 (s, 1 H, C-11 CH), 3.32 (s, 3 H, C-3" $OCH_3$), 3.07 (s, 3 H, C-6 $OCH_3$), 2.42 (s, 3 H, C-3'$NCH_3$), 1.44 (s, 3 H, C-6 $CH_3$), 1.41 (s, 3 H, C-12 $CH_3$), 1.31 (d, J=6 Hz, 3 H, C-6" $CH_3$), 1.26 (s, 3 H, C-3" $CH_3$), 1.16 (d, J=7 Hz, 3 H, C-8 $CH_3$), 1.07 (d, J=8 Hz, 3 H, C-4 $CH_3$), 1.03 (d, J=7 Hz, 3 H, C-10 CH3), 0.82 (t, J=7 Hz, 3 H, C-15 $CH_3$); $^{13}$C NMR (75 MHz, $CDCl_3$) δ 216.2, 176.2, 157.1, 139.2, 132.2, 131.0, 130.3, 130.2, 128.4, 102.4, 96.2, 82.7, 80.5, 78.8, 77.8, 77.7, 76.3, 75.0, 72.7, 68.6, 65.7, 60.3, 50.7, 50.6, 49.5, 45.4, 45.3, 44.8, 39.0, 38.9, 38.8, 37.3, 34.8, 33.3, 32.6, 21.9, 21.5, 21.3, 20.1, 18.9, 18.7, 16.0, 14.2, 14.1, 10.2, 9.6; IR (KBr) ν 3420, 2970, 2940, 1760, 1735, 1710, 1460, 1420, 1380, 1235, 1170, 1065, 1050, 1010, 1000 $cm^{-1}$; Anal. Calcd for $C_{46}H_{72}Cl_2N_2O_{13}$·0.75 $H_2O$: C, 56.39; H, 7.44; N, 2.81. Found: C, 56.63; H, 7.36; N, 2.78.

Step 5: 3'-N-Desmethyl-3'-N-cyclopentyl-11-deoxy-11-[carboxy-(3,4-dichlorophenethylamino)]-6-O-methyl-erythromycin A 11,12-(cyclic carbamate) (Compound 12, Scheme 2)

0.2 g (0.21 mmol) of the compound obtained in Step 4 was dissolved in 3 mL of methanol and treated with cyclopentanone (88 mg, 1.05 mmol), sodium cyanoborohydride (20 mg, 0.32 mmol) and acetic acid (1 drop) and the mixture stirred at ambient temperature. After 48 h TLC [$CH_2Cl_2$:MeOH, 9:1, Ce (IV) visualization] indicated complete conversion to a new, less polar material. The reaction was partitioned between ethyl acetate (300 mL) and 50% saturated sodium bicarbonate solution (300 mL). The organic layer was washed with water (2×200 mL), and brine (200 mL) prior to drying ($Na_2SO_4$), filtering and concentrating. The resulting residue was filtered through a silica gel plug ($CH_2Cl_2$:MeOH, 9:1) and the resulting product crystallized from acetonitrile/water to yield 153 mg (73%) of compound 12 as colorless needles: $R_f$=0.50 (CH$_2$Cl$_2$:MeOH, 9:1); mp 145–147° C. (CH$_3$CN/H$_2$O); MS (FAB) (M+H)$^+$ at m/z 999; HRMS m/z (M+H)$^+$ calcd 999.5116, obsd 999.5110; $^1$ H NMR (300 MHz, CDCl$_3$) δ 7.44 (d, J=2 Hz, 1 H), 7.33 (d, J=8 Hz, 1 H), 7.18 (dd, J=8, 2 Hz, 1 H), 4.91 (d, J=4 Hz, 1 H), 4.88 (dd, J=11, 2 Hz, 1 H), 4.44 (d, J=7 Hz, 1 H), 4.03-3.98 (m, 1 H), 3.88-3.76 (m, 2 H), 3.73 (d, J=10 Hz, 1 H), 3.68 (s, 1 H), 3.65 (d, J=7 Hz, 1 H), 3.49-3.46 (m, 1 H), 3.32 (s, 3 H), 3.17 (dd, J=10, 7 Hz, 1 H), 3.11 (q, J=7 Hz, 1 H), 3.05 (s, 3 H), 3.02-2.95 (m, 2 H), 2.93-2.83 (m, 3 H), 2.64-2.60 (m, 2 H), 2.36 (d, J=15 Hz, 1 H), 2.16 (s, 3 H), 2.14 (d, J=10 Hz, 1 H), 1.93-1.75 (series of m, 7 H), 1.70-1.41 (series of m, 7 H), 1.41 (s, 3 H), 1.38 (s, 3 H), 1.33-1.32 (m, 2 H), 1.28 (d, J=6 Hz, 3 H), 1.28-1.24 (m, 1 H), 1.24 (s, 3 H), 1.20 (d, J=6 Hz, 3 H), 1.20 (d, J=6 Hz, 3 H), 1.13 (d, J=7 Hz, 3 H), 1.11 (d, J=8 Hz, 3 H), 1.00 (d, J=7 Hz, 3 H), 0.81 (t, J=7 Hz, 3 H); $^{13}$C NMR (75 MHz, CDCl$_3$) δ 216.2, 176.3, 157.1, 139.3, 132.1, 131.0, 130.2, 130.0, 128.3, 102.9, 96.0, 82.8, 80.1, 78.8, 77.9, 77.7, 76.1, 72.6, 70.2, 68.9, 65.7, 63.5, 63.0, 60.3, 50.6, 49.4, 45.5, 45.2, 44.7, 39.0, 38.9 (2C), 34.8, 33.1, 32.5, 31.5, 30.9, 30.1, 23.7, 23.6, 21.8, 21.4 (2C), 20.1, 18.8, 18.6, 15.9, 14.1, 14.0, 10.2, 8.9; IR (KBr) ν 3440, 2970, 1760, 1740, 1715, 1460, 1380, 1235, 1170, 1070, 1055, 1015, 1000 cm$^{-1}$; Anal. Calcd for C$_{51}$H$_{80}$ Cl$_2$ N$_2$O$_{13}$: C, 61.24; H, 8.06; N, 2.80. Found: C, 61.07; H, 8.18; N, 2.54.

EXAMPLE 2

3'-N-Desmethyl-3'-N-cyclopropyl-11-deoxy-11-[carboxy-(3,4-dichlorophenethylamino)]-6-O-methyl-erythromycin A 11,12-(cyclic carbamate)

The title compound was prepared according to the process described in Example 1 by substituting [(1-ethoxycyclopropyl)oxy]trimethylsilane for cyclopentanone: $R_f$=0.35 (CH$_2$Cl$_2$:MeOH, 95:5); mp 258–260° C. (CH$_3$CN); IR (KBr) ν 3450, 2970, 2940 1750, 1740, 1730, 1470, 1460, 1380, 1240, 1170, 1070, 1010, 1000 cm$^{-1}$; $^1$ H NMR (300 MHz, CDCl$_3$) δ 7.46 (d, J=2 Hz, 1 H), 7.36 (d, J=8 Hz, 1 H), 7.20 (dd, J=8, 2 Hz, 1 H), 4.93 (d, J=4 Hz, 1 H), 4.91 (dd, J=9, 2 Hz, 1 H), 4.45 (d, J=7 Hz, 1 H), 4.08-3.98 (m, 1 H), 3.95-3.76 (m, 2 H), 3.75 (d, J=9 Hz, 1 H), 3.70 (s, 1 H), 3.67 (d, J=7 Hz, 1 H), 3.58-3.48 (m, 1 H), 3.34 (s, 3 H), 3.20-3.11 (series of m, 2 H), 3.08 (s, 3 H), 3.04-2.82 (series of m, 4 H), 2.65-2.55 (m, 2 H), 2.39 (d, J=15 Hz, 1 H), 2.31 (s, 3 H), 2.21 (d, J=10 Hz, 1 H), 1.99-1.81 (series of m, 3 H), 1.78-1.75 (series of m, 3 H), 1.65-1.50 (series of m, 3 H), 1.44 (s, 3 H), 1.42-1.38 (m, 1 H), 1.40 (s, 3 H), 1.32 (d, J=6 Hz, 3 H), 1.27 (s, 3 H), 1.25 (d, J=6 Hz, 3 H), 1.23 (d, J=6 Hz, 3 H), 1.16 (d, J=7 Hz, 3 H), 1.11 (d, J=7 Hz, 3 H), 1.03 (d, J=7 Hz, 3 H), 0.83 (t, J=7 Hz, 3 H), 0.62-0.45 (series of m, 3 H), 0.36-0.28 (m, 1 H); $^{13}$C NMR (75 MHz, CDCl$_3$) δ 216.3, 176.4, 157.2, 139.4, 132.2, 131.1, 130.3, 130.2, 128.4, 103.1, 96.2, 82.8, 80.4, 79.0, 78.0, 77.6, 76.3, 72.7, 70.5, 69.0, 65.8, 64.8, 60.5, 50.7, 49.5, 45.6, 45.3, 44.8, 39.2, 39.1, 39.0, 37.0, 36.6, 35.2, 32.7, 30.1, 22.0, 21.6, 21.5, 20.2, 18.9, 18.7, 16.1, 14.3, 14.2, 10.3, 9.1, 7.9, 6.8; MS (APCI) (M+H)$^+$ at m/z 971; HRMS m/z (M+H)$^+$ calcd 971.4803, obsd 971.4837; Anal. Calcd for C$_{49}$H$_{76}$Cl$_2$N$_2$O$_{13}$: C, 60.55; H, 7.88; N, 2.88. Found: C, 60.62; H, 7.82; N, 2.88.

EXAMPLE 3

3'-N-Desmethyl-3'-N-n-propyl-11-deoxy-11-[carboxy-(3,4-dichlorophenethylamino)]-6-O-methyl-erythromycin A 11,12-(cyclic carbamate)

The title compound was prepared according to the process described in Example 1 except that propanal was substituted for cyclopentanone: $R_f$=0.45 (CHCl$_3$:MeOH:NH$_4$OH, 90:8:1); IR (KBr) ν 3440, 2970, 2930, 1760, 1735, 1710, 1460, 1380, 1235, 1170, 1065, 1055, 1010, 1000 cm$^{-1}$; $^1$ H NMR (300 MHz, CDCl$_3$) δ 7.46 (d, J=2 Hz, 1 H), 7.36 (d, J=8 Hz, 1 H), 7.20 (dd, J=8, 2 Hz, 1 H), 4.93-4.88 (m, 2 H), 4.45 (d, J=7 Hz, 1 H), 4.04-3.99 (m, 1 H), 3.88-3.81 (m, 2 H), 3.75 (d, J=9 Hz, 1 H), 3.70 (s, 1 H), 3.68 (d, J=8 Hz, 1 H), 3.49-3.48 (m, 1 H), 3.34 (s, 3 H), 3.22 (dd, J=10, 7 Hz, 1 H), 3.13 (q, J=7 Hz, 1 H), 3.058 (s, 3 H), 3.07-2.82 (series of m, 5 H), 2.65-2.29 (series of m, 5 H), 2.27 (s, 3 H), 2.19 (d, J=10 Hz, 1 H), 1.94-1.48 (series of m, 9 H), 1.44 (s, 3 H), 1.40 (s, 3 H), 1.31 (d, J=7 Hz, 3 H), 1.27 (s, 3 H), 1.25-1.13 (m, 2 H), 1.23 (d, J=6 Hz, 3 H), 1.22 (d, J=7 Hz, 3 H), 1.16 (d, J=7 Hz, 3 H), 1.12 (d, J=7 Hz, 3 H), 1.03 (d, J=7 Hz, 3 H), 0.91 (t, J=7 Hz, 2 H), 0.8 (t, J=7 Hz, 3 H); $^{13}$C NMR (75 MHz, CDCl$_3$) δ 216.3, 176.4, 157.2, 139.3, 132.2, 131.0, 130.3, 130.2, 128.4, 102.9, 96.2, 82.8, 80.1, 78.9, 77.9, 77.8, 76.2, 72.6, 70.6, 68.9, 65.8, 65.6, 60.3, 55.0, 50.7, 49.5, 45.5, 45.3, 44.8, 39.1, 39.0, 38.9, 36.9, 34.8, 32.6, 29.5, 21.9, 21.5, 21.4, 21.3, 20.2, 18.9, 18.7, 16.0, 14.2, 14.1, 11.6, 10.2, 9.0; MS (APCI) (M+H)$^+$ m/z 972; Anal. Calcd for C$_{51}$H$_{80}$ Cl$_2$ N$_2$O$_{13}$·0.5 H$_2$O: C, 59.86; H, 8.10; N, 2.84. Found: C, 59.93; H, 8.24; N, 2.88.

EXAMPLE 4

3'-N-Desmethyl-3'-N-cyclobutyl-11-deoxy-11-[carboxy-(3,4-dichlorophenethylamino)]-6-O-methyl-erythromycin A 11,12-(cyclic carbamate) hydrochloride Step 1: The free base of the title compound was prepared according to the process described in Example 1 except that cyclobutanone was substituted for cyclopentanone: $R_f$=0.55 (CH$_2$Cl$_2$:MeOH, 9:1); IR (KBr) ν 3460, 2930, 1760, 1740, 1710, 1460, 1380, 1235, 1170, 1100, 1060, 1005, 995 cm$^{-1}$; $^1$H NMR (300 MHz, CDCl$_3$) δ 7.46 (d, J=2 Hz, 1 H), 7.35 (d, J=8 Hz, 1 H), 7.20 (dd, J=8, 2 Hz, 1 H), 4.94-4.88 (m, 2 H), 4.45 (d, J=7 Hz, 1 H), 4.04-3.78 (m, 3 H), 3.75 (d, J=10 Hz, 1 H), 3.70 (s, 1 H), 3.67-3.64 (m, 1 H), 3.66 (d, J=8 Hz, 1 H), 3.64-3.45 (m, 1 H), 3.33 (s, 3 H), 3.28-3.12 (m, 3 H), 3.05 (s, 3 H), 3.06-2.82 (m, 4 H), 2.65-2.60 (m, 1 H), 2.49-2.29 (m, 2 H), 2.13 (d, J=10 Hz, 1 H), 2.06 (s, 3 H), 2.01-1.48 (series of m, 14 H), 1.43 (s, 3 H), 1.40 (s, 3 H), 1.31 (d, J=6 Hz, 3 H), 1.25 (s, 3 H), 1.24 (d, J=5.9 Hz, 3 H), 1.22 (d, J=5.9 Hz, 3 H), 1.16 (d, J=8 Hz, 3 H), 1.13 (d, J=8 Hz, 3 H), 1.03 (d, J=7 Hz, 3 H), 0.83 (t, J=7 Hz, 3 H); $^{13}$C NMR (75 MHz, CDCl$_3$) δ 216.2, 176.3, 157.1, 139.3, 132.2, 131.0, 130.2, 130.0, 128.4, 103.1, 96.1, 82.8, 80.4, 78.9, 77.9, 77.8, 76.3, 72.7, 70.1, 68.9, 65.8, 60.4, 60.1, 56.8, 50.6, 49.4, 45.6, 45.3, 44.8, 39.1, 39.0, 34.9, 32.7, 31.0, 29.7, 28.6, 28.2, 21.9, 21.5, 21.4, 20.2, 18.9, 18.7, 16.0, 14.2, 14.1, 14.0, 10.2, 9.0; MS (FAB) (M+H)$^+$ at m/z 985; HRMS m/z (M+H)$^+$ calcd 985.4959, obsd 985.4949; Anal. Calcd for C$_{51}$H$_{78}$Cl$_2$ N$_2$O$_{13}$·0.75 H$_2$O: C, 60.55; H, 7.92; N, 2.76. Found: C, 60.56; H, 7.97; N, 3.02.

Step 2: Preparation of HCl salt of 3'-N-Desmethyl-3'-N-cyclobutyl-11-deoxy-11-[carboxy-(3,4-dichlorophenethylamino)]-6-O-methyl-erythromycin A 11,12-(cyclic carbamate)

160 mg (0.16 mmol) of 3'-N-desmethyl-3'-N-cyclobutyl-11-deoxy-11-[carboxy-(3,4-dichlorophenethylamino)]-6-O-methyl-erythromycin A 11,12-(cyclic carbamate) was dissolved in 5 mL of EtOAc and treated with 0.16 mL of 1 M HCl/ether. The mixture was stirred for 0.5 h at ambient temperature during which a white precipitate formed. The precipitate was filtered to yield 125 mg of 3'-N-desmethyl-3'-N-cyclobutyl-11-deoxy-11-[carboxy-(3,4- dichlorophenethylamino)]-6-O-methyl-erythromycin A 11,12 (cyclic carbamate) hydrochloride: MS(CI)(M)$^+$ at m/z 985; Anal. Calcd for $C_{50}H_{79}Cl_3N_2O_{13} \cdot 0.5\ H_2O$: C, 58.21; H, 7.81; N, 2.71; Cl, 10.31. Found: C, 58.24; H, 7.90; N, 2.66; Cl, 10.06; RP-HPLC $R_f$=22.0 min (45–90% $CH_3CN$, 1% min gradient).

EXAMPLE 5

3'-N-Desmethyl-3'-N-cyclohexyl-11-deoxy-11-[carboxy-(3,4-dichlorophenethylamino)]-6-O-methyl-erythromycin A 11,12-(cyclic carbamate)

The title compound was prepared according to the process described in Example 1 except that cyclohexanone was substituted for cyclopentanone. The crude product was purified on a silica gel column ($CH_2Cl_2$:MeOH, 9:1) to yield an amorphous solid: $R_f$=0.5 ($CH_2Cl_2$:MeOH, 9:1); IR (KBr) ν 3440, 2970, 2930, 1760, 1730, 1705, 1455, 1380, 1235, 1100, 1070, 1010, 1000 cm$^{-1}$; $^1$H NMR (300 MHz, $CDCl_3$) δ 7.46 (d, J=2 Hz, 1 H), 7.35 (d, J=8 Hz, 1 H), 7.20 (dd, J=8, 2 Hz, 1 H), 4.93 (d, J=5 Hz, 1 H), 4.91 (dd, J=11, 2 Hz, 1 H), 4.46 (d, J=6 Hz, 1 H), 4.08-3.98 (m, 1 H), 3.88-3.80 (m, 2 H), 3.76 (d, J=10 Hz, 1 H), 3.70 (s, 1 H), 3.68 (d, J=8 Hz, 1 H), 3.50-3.46 (m, 1 H), 3.34 (s, 3 H), 3.17-3.11 (series of m, 2 H), 3.08 (s, 3 H), 3.04-2.82 (m, 5 H), 2.61-2.32 (m, 2 H), 2.39 (d, J=15 Hz, 1 H), 2.25 (s, 3 H), 2.19 (d, J=10 Hz, 1 H), 1.94-1.48 (series of m, 17 H), 1.44 (s, 3 H), 1.40 (s, 3 H), 1.36-1.34 (m, 2 H), 1.31 (d, J=7 Hz, 3 H), 1.27 (s, 3 H), 1.23 (d, J=6 Hz, 3 H), 1.22 (d, J=6 Hz, 3 H), 1.16 (d, J=7 Hz, 3 H), 1.13 (d, J=8 Hz, 3 H), 1.03 (d, J=7 Hz, 3 H), 0.83 (t, J=7 Hz, 3 H); $^{13}$C NMR (75 MHz, $CDCl_3$) δ 216.2, 176.3, 157.1, 139.3, 132.1, 131.0, 130.2, 130.1, 128.4, 103.0, 96.2, 82.8, 80.1, 78.9, 77.9 (2C), 76.2, 72.6, 70.4, 68.9, 65.8, 63.0, 61.2, 60.3, 50.7, 49.5, 45.5, 45.3, 44.8, 39.1, 39.0, 38.9, 34.8, 33.5, 32.6, 31.8, 31.7, 30.9, 26.0, 25.9, 21.9, 21.5, 20.1, 18.9, 18.7, 16.0, 14.2, 14.1, 10.2, 8.9; MS (FAB) (M+H)$^+$ at m/z 1013; HRMS m/z (M+H)$^+$ calcd 1013.5272, obsd 1013.5242; Anal. Calcd for $C_{52}H_{82}Cl_2N_2O_{13}$: C, 61.58; H, 8.15; N, 2.76. Found: C, 61.31; H, 8.16; N, 2.76.

EXAMPLE 6

3'-N-Desmethyl-3'-N-isovaleryl-11-deoxy-11-[carboxy-(3,4-dichlorophenethylamino)]-6-O-methyl-erythromycin A 11,12-(cyclic carbamate)

The title compound was prepared according to the method described in Example 1 but substituting isovaleraldehyde for cyclopentanone. The crude product was purified on a silica gel column ($CHCl_3$:MeOH:$NH_4OH$, 90:8:1) to yield an amorphous solid: $R_f$=0.33 ($CHCl_3$:MeOH, 94:6); IR (KBr) ν 3435, 2960, 2940, 1750, 1735, 1460, 1165, 1105, 1065, 1055, 1030, 1010 cm$^{-1}$; $^1$H NMR (300 MHz, $CDCl_3$) δ 7.46 (d, J=2 Hz, 1 H), 7.34 (d, J=8 Hz, 1 H), 7.19 (dd, J=8, 2 Hz, 1 H), 4.92-4.88 (series of m, 2 H), 4.44 (d, J=7 Hz, 1 H), 4.03-4.00 (m, 1 H), 3.87-3.81 (m, 2 H), 3.75 (d, J=10 Hz, 1 H), 3.69 (s, 1 H), 3.67 (d, J=8 Hz, 1 H), 3.64 (broad singlet, 1 H), 3.50-3.47 (m, 1 H), 3.33 (s, 3 H), 3.21-3.17 (m, 1 H), 3.14-3.11 (m, 1 H), 3.07 (s, 3 H), 3.05-2.97 (series of m, 2 H), 2.94-2.86 (series of m, 2 H), 2.64-2.62 (m, 1 H), 2.57-2.52 (m, 1 H), 2.38 (d, J=14 Hz, 1 H), 2.33-2.30 (m, 1 H), 2.23 (s, 3 H), 2.18 (d, J=10, 1 H), 1.93-1.86 (series of m, 2 H), 1.77-1.51 (series of m, 7 H), 1.43 (s, 3 H), 1.39 (s, 3 H), 1.38-1.21 (series of m, 14 H), 1.15 (d, J=7 Hz, 3 H), 1.12 (d, J=8 Hz, 3 H), 1.02 (d, J=7 Hz, 3 H), 0.90 (d, 6 H), 0.82 (t, J=7 Hz, 3 H); $^{13}$C NMR (75 MHz, $CDCl_3$) δ 216.1, 176.4, 157.2, 139.3, 132.1, 131.0, 130.1, 128.4, 103.0, 96.1, 82.8, 80.2, 78.9, 77.9, 77.9, 76.22, 72.63, 70.6, 69.0, 65.8, 65.5, 60.3, 51.6, 50.6, 49.5, 45.3, 44.8, 39.1, 39.0, 39.0, 37.5, 36.8, 34.8, 32.6, 29.4, 26.1, 22.7, 22.7, 21.9, 21.4, 20.1, 18.9, 18.7, 16.0, 14.2, 14.1, 10.2, 9.0; MS (FAB) (M+H)$^+$ at m/z 1001; Anal. Calcd for $C_{51}H_{82}Cl_2N_2O_{13}$ 0.5 $H_2O$: C, 60.58; H, 8.27; N, 2.77. Found: C, 60.46; H, 8.11; N, 2.78.

EXAMPLE 7

3'-N-Desmethyl-3'-N-(3-methylthiopropyl)-11-deoxy-11-[carboxy-(3,4-dichlorophenethylamino)]-6-O-methyl-erythromycin A 11,12-(cyclic carbamate)

The compound was prepared in accordance with the method described in Example 1 but substituting 3-methylthiopropionaldehyde for cyclopentanone. The crude product was purified on a silica gel column ($CHCl_3$:MeOH:$NH_4OH$, 90:8:1) to yield an amorphous solid: IR (KBr) ν 3460, 2970, 2930, 1750, 1460, 1235, 1165, 1125, 1100, 1065, 1050, 1010, 995 cm$^{-1}$; $^1$H NMR (300 MHz, $CDCl_3$) δ 7.44 (d, 1 H), 7.34 (d, 1 H), 7.19 (dd, 1 H), 4.91 -4.87 (series of m, 2 H), 4.43 (d, 1 H), 4.02-3.99 (m, 1 H), 3.86-3.81 (m, 2 H), 3.74 (d, 1 H), 3.69 (s, 1 H), 3.66 (d, 1 H), 3.50-3.47 (m, 2 H), 3.32 (s, 3 H), 3.22-3.19 (m, 1 H), 3.13-3.10 (m, 1 H), 3.06 (s, 3 H), 3.04-2.99 (series of m, 2 H), 2.91-2.87 (series of m, 2 H), 2.64-2.62 (series of m, 2 H), 2.54-2.43 (series of m, 4 H), 2.37 (d, 1 H), 2.24 (s, 3 H), 2.20 (d, 1 H), 2.09 (s, 2 H), 1.99 (d, 1 H), 1.90-1.86 (series of m, 2 H), 1.78-1.73 (series of m, 4 H), 1.65 (d, 1 H), 1.60-1.50 (series of m, 2 H), 1.42 (s, 3 H), 1.39 (s, 3 H), 1.29 (d, 3 H), 1.25-1.20 (series of m, 10 H), 1.14 (d, 3 H), 1.11 (d, 3 H), 1.02 (d, 3 H), 0.82 (t, 3 H); $^{13}$C NMR (75 MHz, $CDCl_3$) δ 216.3, 176.4, 157.1, 139.3, 132.1, 131.0, 130.2, 130.1, 128.4, 102.9, 96.1, 82.8, 80.1, 78.9, 77.8, 76.2, 72.6, 70.7, 68.8, 65.7, 65.7, 60.3, 52.2, 50.6, 49.5, 45.5, 45.3, 44.8, 39.1, 38.9, 36.7, 34.8, 32.6, 32.0, 29.5, 27.5, 21.9, 21.4, 21.4, 20.1, 18.8, 18.6, 16.0, 15.6, 14.2, 14.1, 10.2, 8.9; MS (FAB) (M+H)$^+$ at m/z 1019; Anal. Calcd for $C_{50}H_{80}Cl_2N_2O_{13}S$: C, 58.87; H, 7.90; N, 2.75. Found: C, 58.81; H, 7.76; N, 2.96.

EXAMPLE 8

3'-N-Desmethyl-3'-N-(3-tetrahydrothienyl)-11-deoxy-11-[carboxy-(3,4-dichlorophenethylamino)]-6-O-methyl-erythromycin A 11,12-(cyclic carbamate)

The title compound was prepared according to the method described in Example 1 but substituting 1,2,3,4-tetrahydrothiophen-3-one for cyclopentanone. The crude product was purified on a silica gel column ($CHCl_3$:MeOH:$NH_4OH$, 90:8:1) to yield an amorphous solid: $R_f$=0.45 ($CHCl_3$:MeOH, 94:6); (KBr) ν 3440, 2965, 2930, 1760, 1735, 1460, 1165, 1130, 1100, 1065, 1050, 1030, 1010, 1000 cm$^{-1}$; $^1$H NMR (300 MHz, $CDCl_3$) δ 7.45 (d, J=2 Hz, 1 H), 7.34 (d, J=8 Hz, 1 H), 7.19 (dd, J=8, 2 Hz, 1 H), 4.92-4.88 (series of m, 2 H), 4.46 (d, J=7 Hz, 1 H), 4.02-3.99 (m, 1 H), 3.89-3.77 (m, 2 H), 3.74 (d, J=10 Hz, 1 H), 3.69 (s, 1 H), 3.52-3.49 (m, 1 H), 3.32 (d, J=3 Hz, 3 H), 3.30-3.26 (m, 1 H), 3.21 (dd, J=10, 7 Hz, 1 H), 3.12 (q, J=7 Hz, 1 H), 3.06 (s, 3 H), 3.05-2.82 (series of m, 7 H), 2.78-2.61 (series of m, 3 H), 2.36 (d, J=15 Hz, 1 H), 2.28 (s, 3 H), 2.19-2.14 (series of m, 3 H), 1.93-1.49 (series of m, 9 H), 1.42 (s, 3 H), 1.39 (s, 3 H), 1.38-1.21 (series of m, 13 H), 1.15 (d, J=7 Hz, 3 H), 1.10 (d, J=8 Hz, 3 H), 1.02 (d, J=7 Hz, 3 H), 0.82 (t, J=7 Hz, 3 H); $^{13}$C NMR (75 MHz, $CDCl_3$) δ 216.2, 176.3, 157.1, 139.2, 132.1, 131.0, 130.2, 130.1, 128.4, 102.8, 96.1, 96.1, 82.8, 80.3, 80.2, 78.9, 77.9, 77.8, 76.2, 72.7, 70.6, 70.5, 68.7, 68.7, 66.7, 65.8, 65.8, 65.8, 63.9, 63.5, 60.3, 50.6, 49.5, 49.5, 45.5, 45.2, 45.2, 44.8, 39.0, 39.0, 38.9, 34.8, 34.2, 33.4, 33.2, 33.0, 32.6, 32.4, 31.8, 31.3, 27.9, 27.9, 21.9, 21.4, 21.4, 20.1, 18.8, 18.6, 16.0, 14.2, 14.1, 10.2, 9.0, 9.0 (more signals than actual carbons due to a mixture of diastereomers); MS (FAB) (M+H)$^+$ at m/z 1017; Anal. Calcd for $C_{50}H_{78}Cl_2$ $N_2O_{13}S$: C, 58.99; H, 7.72; N, 2.75. Found: C, 58.85; H, 7.93; N, 2.67.

EXAMPLE 9

3'-N-Desmethyl-3'-N-(3,4-dimethylcyclopentyl)-11-deoxy-11-[carboxy-(3,4-dichlorophenethylamino)]-6-O-methyl-erythromycin A 11,12-(cyclic carbamate)

The title compound was prepared in accordance with the method described in Example 1 but substituting 3,4-dimethylcyclopentan-1-one for cyclopentanone. The crude product was purified on a silica gel column (CHCl$_3$:MeOH:NH$_4$OH, 90:8:1) to yield an amorphous solid. IR (KBr) v 3450, 2970, 2950, 1750, 1735, 1460, 1170, 1110, 1070, 1045, 1015, 1000 cm$^{-1}$; $^1$H NMR (300 MHz, CDCl$_3$) δ 7.45 (d, J=2 Hz, 1 H), 7.34 (d, J=8 Hz, 1 H), 7.18 (dd, J=8, 2 Hz, 1 H), 4.93-4.92 (m, 1 H), 4.89 (dd, J=2, 10, 1 H), 4.45 (t, J=7 Hz, 1 H), 4.03-4.00 (m, 1 H), 3.88-3.77 (m, 2 H), 3.74 (d, J=10 Hz, 1 H), 3.69 (s, 1 H), 3.66 (d, J=7 Hz, 1 H), 3.50-3.47 (m, 1 H), 3.33 (s, 3 H), 3.19-3.10 (series of m, 2 H), 3.06 (s, 3 H), 3.04-2.94 (series of m, 3 H), 2.92-2.84 (series of m, 2 H), 2.65-2.55 (series of m, 2 H), 2.36 (d, J=15 Hz, 1 H), 2.17-2.14 (series of m, 4 H) 1.94-1.74 (series of m, 6 H), 1.63-1.44 (series of m, 4 H), 1.42 (s, 3 H), 1.39 (s, 3 H), 1.30 (d, J=6 Hz, 3 H), 1.27-1.17 (series of m, 10 H), 1.14 (d, J=7 Hz, 3 H), 1.12 (d, J=8 Hz, 3 H), 1.02 (d, J=7 Hz, 3 H), 0.98 (d, J=6 Hz, 3 H), 0.96-0.94 (m, 3 H), 0.82 (t, J=7 Hz, 3 H); MS (APCI) (M+H)$^+$ at m/z 1027; Anal. Calcd for $C_{51}H_{82}Cl_2$ $N_2O_{13}$: C, 61.91; H, 8.23; N, 2.72. Found: C, 61.63; H, 8.22; N, 2.69.

EXAMPLE 10

3'-N-Desmethyl-3'-N-isopropyl-11-deoxy-11-[carboxy-(α,α-cyclopropyl-3,4-dichlorophenethylamino)]-6-O-methyl-erythromycin A 11,12-(cyclic carbamate)

Step 1: Preparation of (α,α-cyclopropyl-3,4-dichlorophenethylamine 3,4-dichlorophenylacetonitrile (25 g, 134 mmol) in 50 mL of anhydrous ether was added dropwise to a suspension of NaNH$_2$ (10.5 g, 268 mmol) in 200 mL of ether. Upon completion of the addition the reaction mixture was heated to reflux temperature for 4 h then cooled to 0° C. A solution of 1-bromo-2-chloroethane (11 mL, 134 mmol) in 25 mL of ether was added dropwise at 0° C. to the reaction mixture afterwhich the reaction was heated to reflux temperature for an additional 18 h. The reaction mixture was then cooled and carefully quenched with H$_2$O prior to partitioning between EtOAc (200 mL) and H$_2$O (200 mL). The organic layer was washed with brine (100 mL) prior to drying (Na2SO$_4$), filtering and concentrating. The desired product was obtained by kugelrohr distillation (165° C., 10 torr) as a colorless oil which solidified upon standing. The solid was crystallized from MeOH/H$_2$O to yield 11.75 g (44%) of α,α-cyclopropyl-3,4-dichlorophenylacetonitrile; MS (CI) (M)$^+$ at m/z 211; Anal. Calcd for $C_{10}H_7Cl_2N$: C, 56.63; H, 3.21; N, 6.60. Found: C, 56.48; H, 3.27; N, 6.55.

α,α-Cyclopropyl-3,4-dichlorophenylacetonitrile (12.3 g, 57.8 mmol) was added dropwise to a suspension of lithium aluminum hydride (2.2 g, 58.0 mmol) in 50 mL of THF at such a rate so as to maintain a gentle reflux. Upon completion of the addition the reaction was stirred at ambient temperature for 4 h under N$_2$. After this period of time the reaction was carefully quenched by the sequential dropwise addition of H$_2$O (2 mL), 15 % (aq.) NaOH (2 mL), and H$_2$O (6 mL). The reaction mixture was filtered and the insoluble solid washed with additional ether. The combined filtrates were dried (Na$_2$SO$_4$), filtered and concentrated to yield α,α-cyclopropyl-3,4-dichlorophenethylamine as a colorless oil. MS Cl (M+H)$^+$ at m/z 216; RP-HPLC R$_f$=4.8 min (40–70% CH$_3$CN, 1% min gradient); $^1$H NMR (300 MHz, CDCl$_3$) δ 7.42 (d, J=2 Hz, 1 H), 7.37 (d, J=8 Hz, 1 H), 7.17 (dd, J=8, 2 Hz, 1 H), 2.78 (s, 2 H), 1.17 (s, 2 H), 0.81-0.77 (m, 4 H).

Step2: 3'-N-Desmethyl-3'-N-isopropyl-11-deoxy-11-[carboxy-(α,α-cyclopropyl-3,4-dichlorophenethylamino)]-6-O-methyl-erythromycin A 11,12-(cyclic carbamate)

The compound was prepared in accordance with the method described in Example 1 but substituting α,α-cyclopropyl-3,4-dichlorophenethylamine from Step 1 above, for 3,4-dichlorophenethylamine and acetone for cyclopentanone. The crude product was crystallized from acetonitrile/water: mp 210–212° C. (CH$_3$CN/H$_2$O); R$_f$=0.95 (CHCl$_3$:MeOH:NH$_4$OH, 90:8:1); HPLC R$_t$=19.7 min, (C-18) column, 50–80% CH$_3$CN, 1%/min gradient; IR (KBr) v 3440, 2960, 2930, 2880, 1760, 1730, 1710, 1460, 1440, 1380, 1230, 1165, 1100, 1060, 1010, 1000 cm$^{-1}$; $^1$H NMR (300 MHz, CDCl$_3$) δ 7.64 (d, J=2 Hz, 1 H), 7.44 (dd, J=8, 2 Hz, 1 H), 7.33 (d, J=8 Hz, 1 H), 4.98 (d, J=4 Hz, 1 H), 4.68 (dd, J=11, 3 Hz, 1 H), 4.47 (d, J=7 Hz, 1 H), 4.35 (d, J=15 Hz, 1 H), 4.07-4.01 (m, 1 H), 3.77-3.67 (m, 2 H), 3.77 (s, 1 H), 3.73 (d, J=7 Hz, 1 H), 3.68 (d, J=7 Hz, 1 H), 3.53-3.48 (m, 1 H), 3.34 (s, 3 H), 3.32-3.13 (m, 2 H), 3.19 (s, 3 H), 3.06 (q, J=8 Hz, 1 H), 2.95-2.87 (m, 2 H), 2.60-256 (m, 2 H), 2.40 (d, J=15 Hz, 1 H), 2.20 (s, 3 H), 2.18 (d, J=10 Hz, 1 H), 1.90 (t, J=7 Hz, 1 H), 1.77-1.56 (series of m, 7 H), 1.42-1.21 (m, 2 H), 1.42 (s, 3 H), 1.33 (d, J=6 Hz, 3 H), 1.32 (s, 3 H), 1.27 (s, 3 H), 1.24 (d, J=6 Hz, 3 H), 1.22 (d, J=6 Hz, 3 H), 1.14-1.04 (series of d, 12 H), 0.99-0.94 (m, 1 H), 0.91 (d, J=7 Hz, 3 H), 0.69 (t, J=7 Hz, 3 H), 0.63-0.58 (m, 1 H); $^{13}$C NMR (75 MHz, CDCl$_3$) δ 216.8, 175.3, 157.5, 139.3, 132.1, 131.5, 130.2, 130.0, 129.5, 102.9, 96.2, 82.4, 80.2, 78.8, 78.1, 78.0, 76.6, 72.7, 70.5, 68.9, 65.8, 62.9, 61.9, 52.6, 51.3, 50.3, 49.5, 45.6, 45.0, 39.4, 39.3, 38.7, 34.9, 33.1, 30.8, 24.1, 21.9, 21.5, 21.1, 20.5, 20.2, 19.5, 18.7, 16.1, 15.2, 14.5, 12.0, 10.9, 9.7, 9.1; MS (FAB) (M+H)$^+$ at m/z 999. Anal. Calcd for $C_{51}H_{80}$ Cl$_2$ $N_2O_{13}$: C, 61.24; H, 8.06; N, 2.80. Found: C, 61.12; H, 8.28; N, 2.74.

EXAMPLE 11

3'-N-Desmethyl-3'-N-cyclobutyl-11-deoxy-11-[carboxy-(α,α-cyclopropyl-3,4-dichlorophenethylamino)]-6-O-methyl-erythromycin A 11,12-(cyclic carbamate)

The title compound was prepared according to the method described in Example 10 but substituting cyclobutanone for acetone. The crude product was crystallized from acetonitrile/water: mp 148–150° C. (CH$_3$CN/H$_2$O); R$_f$=0.6 (CHCl$_3$:MeOH:NH$_4$OH, 90:8:1); HPLC R$_t$=(C-18) 19.7 min, 50–80% CH$_3$CN, 1%/min gradient; IR (KBr), v 3440, 2970, 2930, 1760, 1735, 1710, 1460, 1380, 1230, 1170, 1100, 1060, 1010, 1000 cm$^{-1}$; $^1$H NMR (300 MHz, CDCl$_3$) δ 7.64 (d, J=2 Hz, 1 H), 7.44 (dd, J=8, 2 Hz, 1 H), 7.33 (d, J=8, Hz, 1 H), 4.99 (d, J=5 Hz, 1 H), 4.69 (dd, J=11, 3 Hz, 1 H), 4.47 (d, J=8 Hz, 1 H), 4.35 (d, J=15 Hz, 1 H), 4.06-4.01

(m, 1 H), 3.77 (s, 1 H), 3.74-3.72 (m, 2 H), 3.69 (d, J=4 Hz, 1 H), 3.63-3.60 (br s, 1 H), 3.52-3.46 (m, 1 H), 3.34 (s, 3 H), 3.22-3.12 (m, 3 H), 3.19 (s, 3 H), 3.04 (t, J=10 Hz, 1 H), 2.96-2.90 (m, 1 H), 2.65-2.55 (m, 1 H), 2.50-2.40 (m, 1 H), 2.40 (d, J=15 Hz, 1 H), 2.13 (d, J=10 Hz, 1 H), 2.06 (s, 3 H), 1.95-1.53 (series of m, 12 H), 1.45-1.32 (m, 1 H), 1.43 (s, 3 H), 1.33 (s, 3 H), 1.33 (d, J=6 Hz, 3 H), 1.27 (s, 3 H), 1.22 (d, J=6 Hz, 6 H), 1.14 (d, J=7 Hz, 3 H), 1.12 (d, J=7 Hz, 3 H), 1.07 (d, J=8 Hz, 3 H), 1.00-0.96 (m, 1 H), 0.91 (d, J=7 Hz, 3 H), 0.69 (t, J=7 Hz, 3 H), 0.64-0.58 (m, 1 H); $^{13}$C NMR (75 MHz, CDCl$_3$) δ 216.8, 175.3, 157.4, 143.5, 131.7, 131.5, 130.2, 129.9, 129.4, 102.9, 96.1, 82.4, 80.3, 78.6, 77.9, 76.7, 72.7, 70.1, 68.9, 65.7, 61.8, 60.1, 56.8, 51.3, 50.3, 49.5, 45.6, 45.0, 39.3, 39.2, 38.6, 34.9, 31.0, 29.9, 28.5, 28.1, 24.0, 21.5, 21.5, 20.2, 19.5, 18.7, 16.0, 15.2, 14.5, 14.1, 12.0, 10.9, 9.7, 9.1; MS (APCI) (M+H)$^+$ at m/z 1011 with 2-Cl; Anal. Calcd for C$_{52}$H$_{80}$Cl$_2$ N$_2$O$_{13}$: C, 61.70; H, 7.96; N, 2.76. Found: C, 61.67; H, 7.89; N, 2.46.

EXAMPLE 12

3'-N-Desmethyl-3'-N-cyclopentyl-11-deoxy-11-[carboxy-(α,α-cyclopropyl-3,4-dichlorophenethylamino)]-6-O-methyl-erythromycin A 11,12-(cyclic carbamate)

The compound was prepared in accordance with the method described in Example 10 but substituting cyclopentanone for acetone. The crude product was crystallized from acetonitrile/water: mp 175–178° C. (CH$_3$CN/H$_2$O); R$_f$=0.65 (CHCl$_3$:MeOH:NH$_4$OH, 90:8:1); IR (MIC) ν 3480, 2960, 2880, 1755, 1740, 1715, 1460, 1380, 1230, 1170, 1070, 1060, 1015, 1000 cm$^{-1}$; $^1$H NMR (300 MHz, CDCl$_3$) δ 7.64 (d, J=2 Hz, 1 H), 7.45 (dd, J=9, 2 Hz, 1 H), 7.33 (d, J=9 Hz, 1 H), 4.99 (d, J=5 Hz, 1 H), 4.69 (dd, J=11, 3 Hz, 1 H), 4.48 (d, J=7 Hz, 1 H), 4.35 (d, J=15 Hz, 1 H), 4.07-4.02 (m, 1 H), 3.78 (s, 1 H), 3.75-3.68 (m, 4 H), 3.55-3.45 (m, 1 H), 3.35 (s, 3 H), 3.22-3.10 (m, 2 H), 3.19 (s, 3 H), 3.05 (t, J=10 Hz, 1 H), 2.96-2.88 (m, 2 H), 2.70-2.58 (m, 2 H), 2.40 (d, J=15 Hz, 1 H), 2.18 (s, 3 H), 2.15 (d, J=10 Hz, 1 H), 1.94-1.58 (series of m, 14 H), 1.43 (s, 3 H), 1.34 (d, J=5 Hz, 3 H), 1.33 (s, 3 H), 1.28 (s, 3 H), 1.25 (d, J=5 Hz, 3 H), 1.23 (d, J=4 Hz, 3 H), 1.15 (d, J=3 Hz, 3 H), 1.12 (d, J=4 Hz, 3 H), 1.08-1.06 (m, 3 H), 1.00-0.96 (m, 2 H), 0.91 (d, J=7 Hz, 3 H), 0.70 (t, J=7 Hz, 3 H), 0.64-0.59 (m, 2 H); $^{13}$C NMR (75 MHz CDCl$_3$) δ 216.8, 175.3, 157.1, 143.5, 131.7, 131.5, 130.1, 129.9, 129.4, 102.9, 96.1, 82.4, 80.2, 78.7, 77.9, 76.7, 72.6, 70.3, 68.9, 65.7, 63.5, 63.0, 61.8, 51.4, 50.3, 49.5, 45.7, 45.0, 39.3, 39.2, 38.6, 34.9, 33.2, 31.7, 31.0, 24.5, 23.8, 23.7, 21.9, 21.5, 20.2, 19.5, 18.7, 16.0, 15.1, 14.5, 12.0, 10.9, 9.7, 9.0; MS (FAB) (M+H)$^+$ at m/z 1025; Anal. Calcd for C$_{53}$H$_{82}$Cl$_2$ N$_2$O$_{13}$: C, 62.03; H, 8.05; N, 2.72. Found: C, 61.86; H, 7.86; N, 2.52.

EXAMPLE 13

3'-N-Desmethyl-3'-N-cyclohexyl-11-deoxy-11-[carboxy-(α,α-cyclopropyl-3,4-dichlorophenethylamino)]-6-O-methyl-erythromycin A 11,12-(cyclic carbamate)

The compound was prepared in accordance with the method described in Example 10 but substituting cyclohexanone for acetone. The crude product was crystallized from hexane: mp 210–212° C.; R$_f$=0.80 (CHCl$_3$:MeOH:NH$_4$OH, 90:8:1); IR (KBr) ν 3440, 2965, 1770, 1760, 1735, 1710, 1460, 1380, 1230, 1165, 1100, 1055, 1010, 1000 cm$^{-1}$; $^1$H NMR (300 MHz, CDCl$_3$) δ 7.63 (d, J=2 Hz, 1 H), 7.45 (dd, J=9, 2 Hz, 1 H), 7.33 (d, J=9 Hz, 1 H), 4.98 (d, J=5 Hz, 1 H), 4.68 (dd, J=11, 3 Hz, 1 H), 4.47 (d, J=7 Hz, 1 H), 4.35 (d, J=5 Hz, 1 H), 4.07-4.02 (m, 1 H), 3.77-3.67 (m, 2 H), 3.77 (s, 1 H), 3.73 (d, J=7 Hz, 1 H), 3.69 (d, J=7 Hz, 1 H), 3.53-3.48 (m, 1 H), 3.35 (s, 3 H), 3.32-3.11 (m, 2 H), 3.19 (s, 3 H), 3.05 (t, J=10 Hz, 1 H), 2.95-2.90 (m, 2 H), 2.60-2.52 (m, 2 H), 2.43-2.38 (m, 2 H), 2.36 (d, J=15 Hz, 1 H), 2.25 (s, 3 H), 2.20 (d, J=10 Hz, 1 H), 1.93-1.56 (series of m, 12 H), 1.43-1.28 (series of m, 4 H), 1.43 (s, 3 H), 1.34 (d, J=5 Hz, 3 H), 1.32 (s, 3 H), 1.28 (s, 3 H), 1.24 (d, J=5 Hz, 3 H), 1.22 (d, J=4 Hz, 3 H), 1.15-1.05 (series of m, 3 H), 1.14 (d, J=3 Hz, 3 H), 1.11 (d, J=4 Hz, 3 H), 1.08-0.96 (m, 1 H), 0.91 (d, J=7 Hz, 3 H), 0.69 (t, J=7 Hz, 3 H), 0.64-0.57 (m, 1 H); $^{13}$C NMR (75 MHz, CDCl$_3$) δ 216.8, 175.3, 157.1, 143.6, 131.7, 131.5, 130.1, 129.4, 102.9, 96.3, 82.4, 80.2, 78.8, 78.1, 78.0, 77.2, 76.8, 72.6, 70.5, 68.9, 65.8, 63.0, 61.9, 61.2, 51.3, 50.3, 49.5, 45.6, 45.1, 39.4, 38.7, 34.9, 33.6, 31.9, 31.8, 30.9, 25.9, 24.0, 21.9, 21.5, 21.4, 20.3, 19.5, 18.7, 16.1, 15.2, 14.5, 12.0, 10.9, 9.7, 9.1; MS (ESI) (M+H)$^+$ at m/z 1039; Anal. Calcd for C$_{54}$H$_{84}$Cl$_2$ N$_2$O$_{13}$: C, 62.35; H, 8.14; N, 2.69. Found: C, 62.45; H, 8.16; N, 2.67.

EXAMPLE 14

3'-N-Desmethyl-3'-N-n-propyl-11-deoxy-11-[carboxy-(3,4-dioxolanophenethylamino)]-6-O-methyl-erythromycin A 11,12-(cyclic carbamate)

The title compound was prepared in accordance with the method described in Example 3 but substituting 3,4-dioxolanophenethylamine for 3,4-dichlorophenethylamine. The desired product was crystallized from CH$_3$CN/H$_2$O: R$_f$=0.31 (8% MeOH/DCM+0.1% NH$_4$OH); IR (KBr) ν 3440, 2960, 2940, 2870, 1745, 1725, 1710, 1500, 1485, 1455, 1440, 1420, 1375, 1320, 1280, 1230, 1165, 1120, 1100, 1070, 1050, 1010, 995 cm$^{-1}$; $^1$H NMR (300 MHz, CDCl$_3$) δ 6.86-6.71 (series of m, 3 H), 5.91 (s, 2 H), 4.97 (dd, J=10.8, 2.0 Hz, 1 H), 4.91 (d, J=4.8 Hz, 1 H), 4.06-3.96 (m, 1 H), 3.86-3.73 (series of m, 3 H), 3.70 (s, 1 H), 3.66 (d, J=7.5 Hz, 1 H), 3.53-3.43 (m, 1 H), 3.33 (s, 3 H), 3.24-3.10 (m, 2 H), 3.08 (s, 3 H), 3.08-2.74 (series of m, 5 H), 2.69-2.58 (m, 1 H), 2.55-2.40 (m, 2 H), 2.38 (d, J=15.3 Hz, 1 H), 2.34-2.25 (m, 1 H), 2.23 (s, 3 H), 2.19 (d, J=10.5 Hz, 1 H), 2.00-1.85 (m, 2 H), 1.80-1.74 (m, 2 H), 1.71-1.44 (series of m, 7 H), 1.43 (s, 3 H), 1.40 (s, 3 H), 1.30 (d, J=6.4 Hz, 3 H), 1.26 (s, 3 H), 1.24-1.20 (m, 6 H), 1.15 (d, J=7.1 Hz, 3 H), 1.12 (d, J=7.5 Hz, 3 H), 1.02 (d, J=7.1 Hz, 3 H), 0.90 (t, J=7.5 Hz, 3 H), 0.84 (t, J=7.1 Hz, 3 H); $^{13}$C NMR (75 MHz, CDCl$_3$) δ 216.1, 176.3, 157.2, 147.5, 145.9, 132.8, 121.9, 109.5, 108.2, 103.0, 100.6, 96.2, 82.7, 80.2, 78.9, 78.0, 77.9, 76.3, 72.7, 70.7, 69.0, 65.8, 65.6, 60.5, 55.1, 50.7, 49.5, 45.5 (2C), 45.3, 39.2 (2C), 39.1, 36.9, 34.9, 33.2, 29.5, 22.0, 21.5, 21.4, 20.2, 18.9, 18.7, 16.0, 14.3, 14.1, 11.6, 10.3, 9.0; MS (FAB) (M+H)$^+$ at m/z 949; Anal. Calcd for C$_{50}$H$_{80}$N$_2$O$_{15}$: C, 63.27; H, 8.49; N, 2.95. Found: C, 63.07; H, 8.65; N, 2.84.

EXAMPLE 15

3'-N-Desmethyl-3'-N-cyclopentyl-11-deoxy-11-[carboxy-(3,4-dioxolanophenethylamino)]-6-O-methyl-erythromycin A 11,12-(cyclic carbamate)

The title compound was prepared in accordance with the method described in Example 1 but substituting 3,4-dioxolanophenethylamine for 3,4-dichlorophenethylamine: MS(FAB) (M+H)$^+$ at m/z 975.

EXAMPLE 16

3'-N-Desmethyl-3'-N-n-propyl-11-deoxy-11-[carboxy-(4-chloro-3-fluorophenethylamino)]-6-O-methyl-erythromycin A 11,12-(cyclic carbamate)

The title compound was prepared in accordance with the method described in Example 3 but substituting 4-chloro- 3-fluorophenethylamine for 3,4-dichlorophenethylamine. The desired product was crystallized from $CH_3CN/H_2O$: mp 217–19° C. ($CH_3CN/H_2O$); IR (KBr) ν 3440, 2965, 2940, 2880, 2830, 1755, 1730, 1710, 1580, 1490, 1460, 1425, 1380, 1360, 1325, 1285, 1235, 1170, 1130, 1110, 1070, 1055, 1015, 1000 cm$^{-1}$; $^1$H NMR (300 MHz, CDCl$_3$) δ 7.32-7.26 (m, 1 H), 7.16 (dd, J=10.2, 2.1 Hz, 1 H), 7.07 (dd, J=8.1, 1.3 Hz, 1 H), 4.93-4.88 (m, 2 H), 4.45 (d, J=7.2 Hz, 1 H), 4.06-3.96 (m, 1 H), 3.92-3.77 (m, 2 H), 3.74 (d, J=9.2 Hz, 1 H), 3.69 (s, 1 H), 3.67 (d, J=7.4 Hz, 1 H), 3.54-3.44 (m, 1 H), 3.33 (s, 3 H), 3.27-3.08 (series of m, 2 H), 3.07 (s, 3 H), 3.06-2.82 (series of m, 5 H), 2.68-2.41 (series of m, 3 H), 2.37 (d, J=15.3 Hz, 1 H), 2.37-2.27 (m, 1 H), 2.27 (s, 3 H), 2.18 (d, J=9.8 Hz, 1 H), 1.98-1.83 (m, 2 H), 1.80-1.46 (series of m, 8 H), 1.43 (s, 3 H), 1.40 (s, 3 H), 1.30 (d, J=6.1 Hz, 3 H), 1.26 (s, 3 H), 1.23 (d, J=7.1 Hz, 3 H), 1.21 (d, J=7.4 Hz, 3 H), 1.15 (d, J=7.1 Hz, 3 H), 1.12 (d, J=7.4 Hz, 3 H), 1.02 (d, J=7.2 Hz, 3 H), 0.91 (t, J=7.3 Hz, 3 H), 0.82 (t, J=7.3 Hz, 3 H); $^{13}$C NMR (75 MHz, CDCl$_3$) δ 216.3, 176.4, 158.8, 157.2, 140.0, 139.9, 130.3, 125.4 (2C), 118.8, 117.3, 117.0, 102.9, 96.2, 82.8, 80.1, 78.9, 77.9 (2C), 76.2, 72.6, 70.6, 68.8, 65.8, 65.6, 60.3, 55.0, 50.7, 49.5, 45.5, 45.3, 44.8, 39.1 (2C), 39.0, 36.9, 34.8, 32.8, 29.5, 21.9, 21.5, 21.4, 20.2, 18.9, 18.7, 16.0, 14.2, 14.1, 11.6, 10.2, 9.9; MS (FAB) (M+H)$^+$ at m/z 957; Anal. Calcd for $C_{49}H_{78}$ Cl F $N_2O_{13}$: C, 61.46; H, 8.21; N, 2.93. Found: C, 61.45; H, 8.17; N, 3.10.

EXAMPLE 17

3'-N-Desmethyl-3'-N-isopropyl-11-deoxy-11-[carboxy-(4-chloro-3-fluorophenethylamino)]-6-O-methyl-erythromycin A 11,12-(cyclic carbamate)

The title compound was prepared in accordance with the method described in Example 10 but substituting 4-chloro-3-fluorophenethylamine for α,α-cyclopropyl-3,4-dichlorophenethylamine: MS(FAB) (M+H)$^+$ at m/z 957.

EXAMPLE 18

3'-N-Desmethyl-3'-N-cyclopentyl-11-deoxy-11-[carboxy-(4-chloro-3-fluorophenethylamino)]-6-O-methyl-erythromycin A 11,12-(cyclic carbamate)

The compound was prepared in accordance with the method described in Example 1 but substituting 4-chloro-3-fluorophenethylamine for 3,4-dichlorophenethylamine: MS(FAB) (M+H)$^+$ at m/z 983.

EXAMPLE 19

3'-N-Desmethyl-3'-N-cyclobutylmethyl-11-deoxy-11-[carboxy-(4-chlorophenethylamino)]-6-O-methyl-erythromycin A 11,12-(cyclic carbamate)

The title compound was prepared in accordance with the method of Example 1 but substituting 4-chlorophenethylamine for 3,4-dichlorophenethylamine and cyclobutylcarboxaldehyde for cyclopentanone: MS(FAB) (M+H)$^+$ at m/z 965.

EXAMPLE 20

3'-N-Desmethyl-3'-N-cyclobutylmethyl-11-deoxy-11-[carboxy-(4-chlorophenethylamino)]-6-O-methyl-erythromycin A 11,12-(cyclic carbamate)

The title compound was prepared in accordance with the method described in Example 1 but substituting 4-chlorophenethylamine for 3,4-dichlorophenethylamine and cyclobutylcarboxaldehyde for cyclopentanone. The desired product was crystallized from $CH_3CN/H_2O$: $R_f$=0.46 (8.5% MeOH/DCM+0.1% NH$_4$OH); IR (KBr) ν 3440, 2970, 1760, 1740, 1715, 1490, 1455, 1420, 1375, 1345, 1320, 1280, 1165, 1100, 1090, 1060, 1005, 990 cm$^{-1}$; $^1$H NMR (300 MHz, CDCl$_3$) δ 7.26-7.25 (series of m, 4 H), 4.96-4.92 (series of m, 2 H), 4.45 (d, J=67.5 Hz, 1 H), 4.04-3.98 (m, 1 H), 3.87-3.54 (series of m, 6 H), 3.50-3.43 (m, 1 H), 3.33 (s, 3 H), 3.19-3.11 (m, 2 H), 3.07 (s, 3 H), 3.05-2.84 (series of m, 5 H), 2.64-2.61 (m, 1 H), 2.50-2.42 (m, 1 H), 2.37 (d, J=15.3 Hz, 1 H), 2.12 (d, J=10.5 Hz, 1 H), 2.06 (s, 3 H), 2.00 (s, 1 H), 1.98-1.48 (series of m, 12 H), 1.42 (s, 3 H), 1.40 (s, 3 H), 1.29 (d, J=6.4 Hz, 3 H), 1.25 (s, 3 H), 1.25-1.24 (m, 1 H), 1.23-1.20 (m, 6 H), 1.15 (d, J=7.5 Hz, 3 H), 1.12 (d, J=57.4 Hz, 3 H), 1.02 (d, J=6.8 Hz, 3 H), 0.83 (t, J=7.5 Hz, 3 H); $^{13}$C NMR (75 MHz, CDCl$_3$) δ 216.2, 176.3, 157.2, 137.4, 131.8, 130.3, 128.4, 103.0, 96.0, 82.7, 80.3, 78.8, 77.9, 77.7, 76.2, 72.6, 70.0, 68.9, 65.7, 60.3, 60.1, 56.8, 50.6, 49.4, 45.5, 45.2, 45.0, 39.0, 34.8, 32.8, 31.0 , 29.6, 28.5, 28.1, 21.9, 21.4, 20.1, 18.8, 18.6, 15.9, 14.2, 14.1, 14.0, 10.2, 9.0; MS (FAB) (M+H)$^+$ at m/z 951; Anal. Calcd for $C_{50}H_{79}$ Cl $N_2O_{13}$·0.6 $H_2O$: C, 62.40; H, 8.40; N, 2.91. Found: C, 62.22; H, 8.33; N, 3.28.

EXAMPLE 21

3'-N-Desmethyl-3'-N-ethyl-11-deoxy-11-[carboxy-(4-chlorophenethylamino)]-6-O-methyl-erythromycin A 11,12-(cyclic carbamate)

The title compound was prepared in accordance with the method described in Example 20 but substituting acetaldehyde for cyclobutylcarboxaldehyde: MS(FAB) (M+H)$^+$ at m/z 925.

EXAMPLE 22

3'-N-Desmethyl-3'-N-isopropyl-11-deoxy-11-[carboxy-(4-chlorophenethylamino)]-6-O-methyl-erythromycin A 11,12-(cyclic carbamate)

The title compound was prepared in accordance with the method described in Example 20 but substituting acetone for cyclobutylcarboxaldehyde: MS(FAB) (M+H)$^+$ at m/z 939.

EXAMPLE 23

3'-N-Desmethyl-3'-N-cyclopentyl-11-deoxy-11-[carboxy-(4-chlorophenethylamino)]-6-O-methyl-erythromycin A 11,12-(cyclic carbamate)

The title compound was prepared in accordance with the method described in Example 20 but substituting cyclopentanone for cyclobutylcarboxaldehyde: MS(FAB) (M+H)$^+$ at m/z 965.

EXAMPLE 24

3'-N-Desmethyl-3'-N-cyclopentyl-11-deoxy-11-[carboxy-(3-chlorophenethylamino)]-6-O-methyl-erythromycin A 11,12-(cyclic carbamate)

The title compound was prepared in accordance with the method described in Example 1 but substituting 3-chlorophenethylamine for 3,4-dichlorophenethylamine. The desired product was crystallized from $CH_3CN/H_2O$: $R_f$=0.55 (8% MeOH/DCM+0.1% NH$_4$OH); IR (KBr) ν 3440, 2965, 2940, 2870, 1750, 1730, 1710, 1595, 1570, 1455, 1420, 1375, 1360, 1310, 1280, 1235, 1165, 1125, 1100, 1075, 1050, 1010, 995 cm$^{-1}$; $^1$H NMR (300 MHz, CDCl$_3$) δ 7.34 (s, 1 H), 7.23-7.15 (series of m, 3 H), 4.97-4.90 (series of m, 2 H), 4.46 (d, J=7.1 Hz, 1 H), 4.08-3.96 (m, 1 H), 3.92-3.78 (m, 2 H), 3.77-3.70 (m, 2 H), 3.66 (d, J=7.5 Hz, 1 H), 3.54-3.42 (m, 1 H), 3.33 (s, 3 H), 3.17-3.11 (m, 2 H), 3.09 (s, 3 H), 3.07-2.82 (series of m, 5 H), 2.70-2.56 (m, 2 H), 2.38 (d, J=15.6 Hz, 1 H), 2.18 (s, 3 H), 2.14 (d, J=10.5 Hz, 1 H), 2.02-1.48 (series of m, 14 H), 1.47-1.22 (series of m, 3 H), 1.43 (s, 3 H), 1.40 (s, 3 H), 1.30 (d, J=6.1 Hz, 3 H), 1.26 (s, 3 H), 1.22 (d, J=6.1 Hz, 3 H), 1.22 (d, J=6.1 Hz, 3 H), 1.15 (d, J=7.4 Hz, 3 H), 1.12 (d, J=7.8 Hz, 3 H), 1.02 (d, J=6.8 Hz, 3 H), 0.84 (t, J=7.1 Hz, 3 H); $^{13}$C NMR (75 MHz, CDCl$_3$) δ 216.2, 176.3, 157.2, 141.1, 134.1, 129.6, 129.2, 127.1, 126.4, 103.1, 96.1, 82.8, 80.3, 78.9, 78.0, 76.3, 72.7, 70.4, 69.0, 65.8, 63.6, 63.1, 60.4, 50.7, 49.5, 45.5, 45.3, 45.0, 39.1, 39.0, 34.9, 33.2, 33.1, 31.6, 31.0, 30.2, 23.8, 22.0, 21.5, 20.2, 18.9, 18.7, 16.0, 14.2, 14.1, 10.3, 9.0; MS (FAB) (M+H)$^+$ at m/z 965; Anal. Calcd for C$_{51}$H$_{81}$ Cl N$_2$O$_{13}$·0.4 H$_2$O: C, 62.96; H, 8.47; N, 2.88. Found: C, 62.97; H, 8.57; N, 2.68.

EXAMPLE 25

3'-N-Desmethyl-3'-N-n-propyl-11-deoxy-11-[carboxy-(3-chlorophenethylamino)]-6-O-methyl-erythromycin A 11,12-(cyclic carbamate)

The title compound was prepared in accordance with the method described in Example 3 but substituting 3-chlorophenethylamine for 3,4-dichlorophenethylamine: MS(FAB) (M+H)$^+$ at m/z 939.

EXAMPLE 26

3'-N-Desmethyl-3'-N-cyclopentyl-11-deoxy-11-[carboxy-(3-chloro-4-fluorophenethylamino)]-6-O-methyl-erythromycin A 11,12-(cyclic carbamate)

The title compound was prepared in accordance with the method described in Example 1 but substituting 3-chloro-4-fluorophenethylamine for 3,4-dichlorophenethylamine. The crude product was purified on a silica gel column (MeOH:CHCl$_3$, 5:95) and crystallized from acetonitrile/water: R$_f$=0.32 (MeOH:CHCl$_3$, 5:95); $^1$H NMR (300 MHz, CDCl$_3$) δ 7.39 (dd, J=2, 7 Hz, 1 H), 7.22-7.19 (m, 1 H), 7.04 (dd, J=9 Hz, 1 H), 4.93-4.89 (series of m, 2 H), 4.45 (d, J=7 Hz, 1 H), 4.04-4.00 (m, 1 H), 3.86-3.80 (series of m, 2 H), 3.74 (d, J=10 Hz, 1 H), 3.70 (s, 1 H), 3.67 (d, J=7 Hz, 1 H), 3.49-3.47 (m, 1 H), 3.33 (s, 3 H), 3.19 (dd, J=3, 7 Hz 1 H), 3.13 (m, 1 H) 3.07 (s, 3 H), 3.04-2.86 (series of m, 5 H), 2.66-2.61 (m, 2 H), 2.37 (d, J=15 Hz, 1 H), 2.18 (s, 3 H), 2.15 (d, J=10 Hz, 1 H), 1.93-1.51 (series of m, 13 H), 1.43 (s, 3 H), 1.40 (s, 3 H), 1.38-1.35 (m, 2 H), 1.30 (d, J=6, 3 H), 1.25 (s, 3 H), 1.22 (s, 3 H), 1.21 (s, 3 H), 1.15 (d, J=7 Hz, 3 H), 1.12 (d, J=7 Hz, 3 H), 1.02 (d, J=7 Hz, 3 H), 0.83 (t, J=7 Hz, 3 H); $^{13}$C NMR (75 MHz, CDCl$_3$) δ 216.3, 176.4, 157.7, 157.2, 155.8, 136.0, 136.0, 131.0, 128.6, 128.5, 116.4, 116.2, 103.0, 96.1, 82.8, 80.2, 78.9, 77.9, 77.8, 76.2, 72.6, 70.3, 69.0, 65.7, 63.5, 63.0, 60.3, 50.6, 49.4, 45.5, 45.2, 45.0, 39.1, 39.0, 34.8, 33.1, 32.5, 31.6, 31.0, 30.1, 23.7, 23.7, 21.9, 21.5, 20.1, 18.8, 18.6, 16.0, 14.2, 14.1, 10.2, 8.9; MS (APCI) (M+H)$^+$ at m/z 983; Anal. Calcd for C$_{51}$H$_{80}$ClFN$_2$O$_{13}$: C, 62.27; H, 8.20; N, 2.85. Found: C, 62.03; H, 8.34; N, 2.76.

EXAMPLE 27

3'-N-Desmethyl-3'-N-cyclobutyl-11-deoxy-11-[carboxy-(3-chloro-4-fluorophenethylamino)]-6-O-methyl-erythromycin A 11,12-(cyclic carbamate)

The title compound was prepared in accordance with the method described in Example 4 but substituting 3-chloro-4-fluorophenethylamine for 3,4-dichlorophenethylamine. The crude product was purified on a silica gel column (MeOH:CHCl$_3$, 5:95) and crystallized from acetonitrile/water: R$_f$=0.30 (CHCl$_3$:MeOH, 92:8); HPLC R$_t$=(C-18) 19.6 min, 45–55% CH$_3$CN, 1%/min gradient; MS (APCI) (M+H)$^+$ at m/z 969.

EXAMPLE 28

3'-N-Desmethyl-3'-N-isopropyl-11-deoxy-11-[carboxy-(3-chloro-4-fluorophenethylamino)]-6-O-methyl-erythromycin A 11,12-(cyclic carbamate)

The title compound was prepared in accordance with the method described in Example 1 but substituting 3-chloro-4-fluorophenethylamine for 3,4-dichlorophenethylamine (and) acetone for cyclopentanone. The crude product was purified on a silica gel column (MeOH:CHCl$_3$, 5:95) and crystallized from acetonitrile/water: $^1$H NMR (300 MHz, CDCl$_3$) δ 7.40 (dd, J=2, 7 Hz, 1 H), 7.22-7.19 (m, 1 H), 7.05 (dd, J=9 Hz, 1 H), 4.93-4.90 (series of m, 2 H), 4.46 (d, J=7 Hz, 1 H), 4.04-4.01 (m, 1 H), 3.87-3.79 (series of m, 2 H), 3.75 (d, J=10 Hz, 1 H), 3.70 (s, 1 H), 3.67 (d, J=7 Hz, 1 H), 3.52-3.49 (m, 1 H), 3.34 (s, 3 H), 3.16-3.11 (series of m, 2 H), 3.08 (s, 3 H), 3.05-2.86 (series of m, 5 H), 2.65-2.63 (m, 1 H), 2.58-2.56 (m, 1 H), 2.37 (d, J=15 Hz, 1 H), 2.21 (s, 3 H), 2.17 (d, J=10 Hz, 1 H), 1.94-1.86 (series of m, 2 H), 1.78-1.75 (series of m, 2 H), 1.66-1.52 (series of m, 3 H), 1.44 (s, 3 H), 1.40 (s, 3 H), 1.31 (d, J=6 Hz, 3 H), 1.26 (s, 3 H), 1.24-1.21 (series of m, 6 H), 1.15 (d, J=7 Hz, 3 H), 1.13 (d, J=7 Hz, 3 H), 1.09 (d, J=6 Hz, 3 H), 1.06 (d, J=6 Hz, 3 H), 1.03 (d, J=7 Hz, 3 H), 0.83 (t, J=7 Hz, 3 H); $^{13}$C NMR (75 MHz, CDCl$_3$) δ 216.3, 176.4, 157.7, 157.2, 155.8, 136.0, 136.0, 131.0, 128.6, 128.5, 116.4, 116.2, 102.9, 96.1, 82.8, 80.1, 78.9, 77.9, 76.2, 72.6, 70.4, 68.9, 65.7, 62.8, 60.3, 52.5, 50.6, 49.5, 45.5, 45.3, 45.0, 39.1, 39.0, 39.0, 34.8, 32.5, 30.8, 21.9, 21.5, 20.1, 18.8, 18.6, 16.0, 14.2, 14.1, 10.2, 8.9; MS (ESI) (M+H)$^+$ at m/z 957; Anal. Calcd for C$_{49}$H$_{78}$ClFN$_2$O$_{13}$: C, 61.46; H, 8.21; N, 2.93. Found: C, 61.69; H, 8.36; N, 3.07.

EXAMPLE 29

3'-N-Desmethyl-3'-N-cyclopropylmethyl-11-deoxy-11-(3-chloro-4-fluorophenethylamino)-6-O-methyl-erythromycin A 11,12-(cyclic carbamate)

The title compound was prepared in accordance with the method described in Example 1 but substituting 3-chloro-4-fluorophenethylamine for 3,4-dichlorophenethylamine and cyclopropanecarboxaldehyde for cyclopentanone. The crude product was purified on a silica gel column (MeOH:CHCl$_3$, 5:95) and crystallized from acetonitrile/water: $^1$H NMR (300 MHz, CDCl$_3$) δ 7.40 (dd, J=2, 7 Hz, 1 H), 7.23-7.20 (m, 1 H), 7.05 (dd, J=9 Hz, 1 H), 4.93-4.91 (series of m, 2 H), 4.47 (d, J=7 Hz, 1 H), 4.04-4.02 (m, 1 H), 3.87-3.81 (series of m, 2 H), 3.75 (d, J=10 Hz, 1 H), 3.71 (s, 1 H), 3.67 (d, J=7 Hz, 1 H), 3.51-3.49 (m, 1 H), 3.34 (s, 3 H), 3.22-3.19 (m, 1 H), 3.13 (q, J=7 Hz, 1 H), 3.08 (s, 3 H), 3.04-2.84 (series of m, 5 H), 2.64-2.61 (series of m, 2 H), 2.44-2.42 (m, 1 H), 2.39 (d, J=15 Hz, 1 H), 2.31 (s, 3 H), 2.26-2.24 (m, 1 H), 2.17 (d, J=10 Hz, 1 H), 1.94-1.85 (series of m, 2 H), 1.78-1.76 (series of m, 2 H), 1.64-1.57 (series of m, 5 H), 1.44 (s, 3 H), 1.41 (s, 3 H), 1.31 (d, J=6, 3 H), 1.26 (s, 3 H), 1.23 (s, 3 H), 1.22 (s, 3 H), 1.16 (d, J=7 Hz, 3 H), 1.13 (d, J=7 Hz, 3 H), 1.03 (d, J=7 Hz, 3 H), 0.84 (t, J=7 Hz, 3 H), 0.55-0.51 (m, 2 H), 0.11 (d, J=4 Hz, 2 H); $^{13}$C NMR (75 MHz, CDCl$_3$) δ 216.3, 176.4, 157.8, 157.2, 155.8, 136.0, 136.0, 131.0, 128.6, 128.5, 116.4, 116.2, 103.0, 96.1, 82.8, 80.2, 78.9, 77.9, 76.3, 72.6, 70.6, 68.9, 65.8, 60.4, 58.6, 50.7, 49.5, 45.5, 45.3, 45.0, 39.1, 39.1, 39.0, 36.9, 34.9, 32.5, 29.5, 21.9, 21.5, 20.2, 18.9, 18.7, 16.0, 14.2, 14.1, 10.2, 10.0, 9.0, 4.4, 3.4; MS (ESI) (M+H)$^+$ at m/z 969; Anal. Calcd for $C_{50}H_{78}ClFN_2O_{13}\cdot0.25(CH_3CN)$: C, 61.90; H, 8.10; N, 3.21. Found: C, 61.96; H, 8.27; N, 3.44.

EXAMPLE 30

3'-N-Desmethyl-3'-N-cyclobutyl-11-deoxy-11-[carboxy-(3,4-difluorophenethylamino)]-6-O-methyl-erythromycin A 11,12-(cyclic carbamate)

The title compound was prepared in accordance with the method described in Example 4 but substituting 3,4-difluorophenethylamine for 3,4-dichlorophenethylamine. The desired product was crystallized from $CH_3CN/H_2O$: mp=222–224° C. ($CH_3CN/H_2O$); IR (FTIR/MIC) ν 3494, 2969, 2943, 2879, 2832, 1746, 1735, 1712, 1608, 1519, 1457, 1449, 1429, 1378, 1327, 1279, 1234, 1167, 1111, 1104, 1071, 1059, 1012, 1002 cm$^{-1}$; $^1$H NMR (300 MHz, CDCl$_3$) δ 7.23-7.03 (series of m, 3 H), 4.95-4.90 (series of m, 2 H), 4.45 (d, J=7.1 Hz, 1 H), 4.06-3.96 (m, 1 H), 3.92-3.76 (m, 2 H), 3.74 (d, J=8.8 Hz, 1 H), 3.70 (s, 1 H), 3.67-3.62 (m, 1 H), 3.66 (d, J=7.4 Hz, 1 H), 3.53-3.42 (m, 1 H), 3.33 (s, 3 H), 3.19-3.07 (m, 2 H), 3.07 (s, 3 H), 3.06-2.80 (series of m, 5 H), 2.68-2.57 (m, 2 H), 2.50-2.42 (m, 1 H), 2.37 (d, J=14.9 Hz, 1 H), 2.13 (d, J=10.2 Hz, 1 H), 2.05 (s, 3 H), 2.05-1.47 (series of m, 14 H), 1.43 (s, 3 H), 1.40 (s, 3 H), 1.30 (d, J=6.1 Hz, 3 H), 1.25 (s, 3 H), 1.22 (d, J=8.5 Hz, 3 H), 1.21 (d, J=6.1 Hz, 3 H), 1.15 (d, J=7.4 Hz, 3 H), 1.12 (d, J=7.5 Hz, 3 H), 1.02 (d, J=6.8 Hz, 3 H), 0.83 (t, J=7.5 Hz, 3 H); $^{13}$C NMR (75 MHz, CDCl$_3$) δ 216.28, 176.39, 157.19, 152.5-146.5 (m, 2C), 136.5-135.5 (m, 1C), 125.0-124.7 (m, 1 C), 117.9-116.8 (m, 2C), 103.08, 96.07, 82.78, 80.34, 78.93, 77.96, 77.86, 76.29, 72.68, 70.14, 68.99, 65.76, 60.42, 60.20, 56.84, 50.66, 49.46, 45.58, 45.30, 45.01, 39.10, 39.02 (2C), 34.88, 32.71, 31.04, 29.74, 28.56, 28.16, 21.97, 21.50, 21.47, 20.14, 18.88, 18.65, 16.00, 14.23, 14.12 (2C), 10.23, 9.00; MS (FAB) (M+H)$^+$ at m/z 953; Anal. Calcd for $C_{50}H_{78}F_2N_2O_{13}\cdot0.2\,H_2O$: C, 62.77; H, 8.26; N, 2.93. Found: C, 62.75; H, 8.36; N, 2.91.

EXAMPLE 31

3'-N-Desmethyl-3'-N-cyclopentyl-11-deoxy-11-[carboxy-(3,4-difluorophenethylamino)]-6-O-methyl-erythromycin A 11,12-(cyclic carbamate)

The title compound was prepared in accordance with the method described in Example 1 but substituting 3,4-difluorophenethylamine for 3,4-dichlorophenethylamine. The desired product was crystallized from $CH_3CN/H_2O$: mp 166–168° C. ($CH_3CN/H_2O$); IR (FTIR/MIC) ν 3451, 2968, 2943, 2880, 2831, 1763, 1747, 1709, 1520, 1453, 1432, 1378, 1327, 1283, 1234, 1168, 1128, 1106, 1069, 1055, 1012, 1000 cm$^{-1}$; $^1$H NMR (300 MHz, CDCl$_3$) δ 7.22-7.03 (series of m, 3 H), 4.95-4.89 (series of m, 2 H), 4.46 (d, J=7.1 Hz, 1 H), 4.07-3.97 (m, 1 H), 3.91-3.75 (m, 2 H), 3.74 (d, J=9.5 Hz, 1 H), 3.70 (s, 1 H), 3.66 (d, J=7.5 Hz, 1 H), 3.55-3.43 (m, 1 H), 3.33 (s, 3 H), 3.24-3.11 (m, 2 H), 3.11-2.80 (series of m, 5 H), 3.07 (s, 3 H), 2.69-2.58 (m, 2 H), 2.37 (d, J=15.2 Hz, 1 H), 2.18 (s, 3 H), 2.14 (d, J=10.2 Hz, 1 H), 1.98-1.48 (series of m, 14 H), 1.43 (s, 3 H), 1.40 (s, 3 H), 1.35-1.31 (m, 2 H), 1.30 (d, J=6.1 Hz, 3 H), 1.18-1.21 (m, 1 H), 1.26 (s, 3 H), 1.22 (d, J=6.1 Hz, 3 H), 1.22 (d, J=6.1 Hz, 3 H), 1.15 (d, J=7.1 Hz, 3 H), 1.12 (d, J=7.8 Hz, 3 H), 1.02 (d, J=6.8 Hz, 3 H), 0.83 (t, J=7.3 Hz, 3 H); $^{13}$C NMR (75 MHz, CDCl$_3$) δ 216.35, 176.42, 157.20, 152.5-146.5 (m, 2C), 136.5-135.5 (m, 1 C), 125.0-124.7 (m, IC), 117.9-116.8 (m, 2C), 103.04, 96.07, 82.77, 80.23, 78.91, 77.94, 77.81, 76.24, 72.65, 70.29, 69.01, 65.74, 63.53, 63.06, 60.34, 50.67, 49.49, 45.58, 45.27, 44.99, 39.07, 38.99 (2C), 34.85, 33.15, 32.69, 31.67, 31.00, 30.10, 23.74, 23.71, 21.95, 21.51, 20.17, 18.87, 18.66, 16.03, 14.23, 14.15, 10.25, 8.99; MS (FAB) (M+H)$^+$ at m/z 967; Anal. Calcd for $C_{51}H_{80}F_2N_2O_{13}\cdot0.4\,CH_3CN\cdot0.4\,H_2O$: C, 62.79; H, 8.34; N, 3.39. Found: C, 62.78; H, 8.45; N, 3.46.

EXAMPLE 32

3'-N-Desmethyl-3'-N-n-propyl-11-deoxy-11-[carboxy-(3,4-difluorophenethylamino)]-6-O-methyl-erythromycin A 11,12-(cyclic carbamate)

The title compound was prepared in accordance with the method described in Example 3 but substituting 3,4-difluorophenethylamine for 3,4-dichlorophenethylamine. The desired product was crystallized from $CH_3CN/H_2O$: mp 228–229° C. ($CH_3CN/H_2O$); IR (FTIR/MIC) ν 3484, 2970, 2941, 2883, 1754, 1734, 1711, 1519, 1459, 1436, 1423, 1379, 1351, 1326, 1282, 1236, 1167, 1127, 1110, 1075, 1055, 1044, 1014, 997 cm$^{-1}$; $^1$H NMR (CDCl$_3$) δ 7.22-7.03 (series of m, 3 H), 4.95-4.89 (series of m, 2 H), 4.44 (d, J=7.2 Hz, 1 H), 4.06-3.96 (m, 1 H), 3.92-3.75 (m, 2 H), 3.75 (d, J=9.2 Hz, 1 H), 3.69 (s, 1 H), 3.67 (d, J=7.8 Hz, 1 H), 3.54-3.43 (m, 1 H), 3.33 (s, 3 H), 3.23-3.11 (m, 2 H), 3.10-2.80 (series of m, 5 H), 3.07 (s, 3 H), 2.69-2.58 (m, 1 H), 2.54-2.40 (m, 2 H), 2.37 (d, J=14.9 Hz, 1 H), 2.33-2.24 (m, 1 H), 2.23 (s, 3 H), 2.17 (d, J=10.2 Hz, 1 H), 1.98-1.82 (m, 2 H), 1.79-1.75 (m, 2 H), 1.71-1.44 (series of m, 6 H), 1.43 (s, 3 H), 1.40 (s, 3 H), 1.30 (d, J=6.4 Hz, 3 H), 1.26 (s, 3 H), 1.22 (d, J=6.1 Hz, 3 H), 1.21 (d, J=7.8 Hz, 3 H), 1.15 (d, J=7.1 Hz, 3 H), 1.12 (d, J=7.4 Hz, 3 H), 1.02 (d, J=6.8 Hz, 3 H), 0.90 (t, J=7.5 Hz, 3 H), 0.83 (t, J=7.3 Hz, 3 H); $^{13}$C NMR (CDCl$_3$) δ 216.36, 176.45, 157.19, 152.5-146.5 (m, 2C), 136.5-135.5 (m, 1C), 125.0-124.7 (m, 1C), 117.9-116.8 (m, 2C), 102.94, 96.17, 82.76, 80.09, 78.94, 77.91 (2C), 76.24, 72.62, 70.64, 68.99, 65.76, 65.60, 60.31, 54.96, 50.67, 49.47, 45.56, 45.28, 44.96, 39.09 (2C), 38.98, 36.87, 34.84, 32.67, 29.39, 21.91, 21.48, 21.40, 20.17, 18.87, 18.68, 16.03, 14.22, 14.13, 11.58, 10.24, 8.96; MS (FAB) (M+H)$^+$ at m/z 941; Anal. Calcd for $C_{49}H_{78}F_2N_2O_{13}$: C, 62.53; H, 8.35; N, 2.98. Found: C, 62.69; H, 8.34; N, 3.12.

EXAMPLE 33

3'-N-Desmethyl-3'-N-cyclopropylmethyl-11-deoxy-11-[carboxy-(3,4-difluorophenethylamino)]-6-O-methyl-erythromycin A 11,12-(cyclic carbamate)

The compound was prepared in accordance with the method of Example 1 by substituting 3,4-difluorophenethylamine for 3,4-dichlorophenethylamine and cyclopropanecarboxaldehyde for cyclopentanone. The desired product was crystallized from $CH_3CN/H_2O$: mp 220–222° C. ($CH_3CN/H_2O$); IR (KBr) ν 3446, 2977, 2938, 2883, 1745, 1734, 1713, 1607, 1518, 1459, 1425, 1378, 1327, 1284, 1236, 1168, 1103, 1094, 1070, 1055, 1013, 1001 cm$^{-1}$; $^1$H NMR (300 MHz, CDCl$_3$) δ 7.23-7.03 (series of m, 3 H), 4.94-4.89 (series of m, 2 H), 4.46 (d, J=7.4 Hz, 1 H), 4.07-3.97 (m, 1 H), 3.92-3.78 (series of m, 2 H), 3.75 (d, J=9.1 Hz, 1 H), 3.70 (s, 1 H), 3.67 (d, J=7.8 Hz, 1 H), 3.54-3.44 (m, 1 H), 3.33 (s, 3 H), 3.24-3.11 (m, 2 H), 3.10-2.80 (series of m, 5 H), 3.07 (s, 3 H), 2.68-2.55 (m, 2 H), 2.47-2.40 (m, 1 H), 2.37 (d, J=15.2 Hz, 1 H), 2.31 (s, 3 H), 2.31-2.19 (m, 1 H), 2.15 (d, J=10.1 Hz, 1 H), 1.98-1.72 (series of m, 4 H), 1.68-1.46 (series of m, 4 H), 1.43 (s, 3 H), 1.40 (s, 3 H), 1.30 (d, J=6.1 Hz, 3 H), 1.25 (s, 3 H), 1.22 (d, J=6.1 Hz, 3 H), 1.22 (d, J=6.1 Hz, 3 H), 1.15 (d, J=7.4 Hz, 3 H), 1.13 (d, J=7.5 Hz, 3 H), 1.02 (d, J=6.8 Hz, 3 H), 0.89-0.78 (m, 1 H), 0.83 (t, J=7.3 Hz, 3 H), 0.58-0.46 (m, 2 H), 0.15-0.07 (m, 2 H); $^{13}$C NMR (75 MHz, CDCl$_3$) δ 216.35, 176.43, 157.20, 152.5-146.5 (m, 2C), 136.5-135.5 (m, 1C), 125.0-124.7 (m, 1 C), 117.9-116.8 (m, 2C), 103.02, 96.13, 82.77, 80.19, 78.94, 77.92, 77.89, 76.26, 72.63, 70.55, 68.96, 65.78, 64.61, 60.34, 58.59, 50.67, 49.49, 45.56, 45.30, 44.99, 39.09 (2C), 39.01, 36.91, 34.85, 32.69, 29.42, 21.93, 21.49, 20.18, 18.89, 18.68, 16.03, 14.23, 14.13, 10.25, 10.04, 9.01, 4.41, 3.36; MS (FAB) (M+H)$^+$ at m/z 953; Anal. Calcd for C$_{50}$H$_{78}$ F$_2$ N$_2$O$_{13}$: C, 63.01; H, 8.25; N, 2.94. Found: C, 63.08; H, 8.28; N, 2.89.

EXAMPLE 34

3'-N-Desmethyl-3'-N-(4-pyridylmethyl)-11-deoxy-11-[carboxy-(4-chlorophenethylamino)]-6-O-methyl-erythromycin A 11,12-(cyclic carbamate)

The title compound was prepared in accordance with the method described in Example 20 but substituting 4-pyridylcarboxaldehyde for cyclobutanone: MS (APCI) (M+H)$^+$ at m/z 988.

EXAMPLE 35

3'-N-Desmethyl-3'-N-(2-butyl)-11-deoxy-11-[carboxy-(4-chlorophenethylamino)]-6-O-methyl-erythromycin A 11,12-(cyclic carbamate)

The title compound was prepared in accordance with the method described in Example 20 but substituting 2-butanone for cyclobutanone: MS (APCI) (M+H)$^+$ at m/z 953.

EXAMPLE 36

3'-N-Desmethyl-3'-N-(3-pentyl)-11-deoxy-11-[carboxy-(4-chlorophenethylamino)]-6-O-methyl-erythromycin A 11,12-(cyclic carbamate)

The title compound was prepared in accordance with the method described in Example 20 but substituting 3-pentanone for cyclobutanone: MS (APCI) (M+H)$^+$ at m/z 967.

EXAMPLE 37

3'-N-Desmethyl-3'-N-(cyclopropylmethyl)-11-deoxy-11-[carboxy-(4-chlorophenethylamino)]-6-O-methyl-erythromycin A 11,12-(cyclic carbamate)

The title compound was prepared in accordance with the method described in Example 20 but substituting cyclopropanecarboxaldehyde for cyclobutanone: MS (APCI) (M+H)$^+$ at m/z 951.

EXAMPLE 38

3'-N-Desmethyl-3'-N-[2-(cyclopropyl)-ethyl]-11-deoxy-11-[carboxy-(4-chlorophenethylamino)]-6-O-methyl-erythromycin A 11,12-(cyclic carbamate)

The title compound was prepared in accordance with the method described in Example 20 but substituting cyclopropyl methyl ketone for cyclobutanone: MS (APCI) (M+H)$^+$ at m/z 965.

EXAMPLE 39

3'-N-Desmethyl-3'-N-propyl-11-deoxy-11-[carboxy-(4-methoxyphenethylamino)]-6-O-methyl-erythromycin A 11,12-(cyclic carbamate)

The title compound was prepared in accordance with the method described in Example 20 but substituting 4-methoxyphenethylamine for 4-chlorophenethylamine and propanal for cyclobutanone: MS (APCI) (M+H)$^+$ at m/z 935.

EXAMPLE 40

3'-N-Desmethyl-3'-N-cyclopentyl-11-deoxy-11-[carboxy-(4-methoxyphenethylamino)]-6-O-methyl-erythromycin A 11,12-(cyclic carbamate)

The title compound was prepared in accordance with the method described in Example 20 but substituting 4-methoxyphenethylamine for 4-chlorophenethylamine and cyclopentanone for cyclobutanone: MS (APCI) (M+H)$^+$ at m/z 961.

EXAMPLE 41

3'-N-Desmethyl-3'-N-propyl-11-deoxy-11-[carboxy-(3,4-dimethylphenethylamino)]-6-O-methyl-erythromycin A 11,12-(cyclic carbamate)

The title compound was prepared in accordance with the method described in Example 20 but substituting 3,4-dimethylphenethylamine for 4-chlorophenethylamine and propanal for cyclobutanone: MS (APCI) (M+H)$^+$ at m/z 933.

EXAMPLE 42

3'-N-Desmethyl-3'-N-cyclopentyl-11-deoxy-11-[carboxy-(3-bromo-4-methoxyphenethylamino)]-6-O-methyl-erythromycin A 11,12-(cyclic carbamate)

The title compound was prepared in accordance with the method described in Example 19 but substituting 3-bromo-4-methoxyphenethylamine for 4-chlorophenethylamine and cyclopentanone for cyclobutanone: MS (APCI) (M+H)$^+$ at m/z 1039.

EXAMPLE 43

3'-N-Desmethyl-3'-N-propyl-11-deoxy-11-[carboxy-(3-bromo-4-methoxyphenethylamino)]-6-O-methyl-erythromycin A 11,12-(cyclic carbamate)

The title compound was prepared in accordance with the method described in Example 19 but substituting 3-bromo-4-methoxyphenethylamine for 4-chlorophenethylamine and propanal for cyclobutanone: MS (APCI) (M+H)$^+$ at m/z 1013.

EXAMPLE 44

3'-N-Desmethyl-3'-N-propyl-11-deoxy-11-[carboxy-(3-chloro-4-fluorophenethylamino)]-6-O-methyl-erythromycin A 11,12-(cyclic carbamate)

The title compound was prepared in accordance with the method described in Example 19 but substituting 3-chloro-4-fluorophenethylamine for 4chlorophenethylamine and propanal for cyclobutanone: MS (APCI) (M+H)$^+$ at m/z 957.

EXAMPLE 45

3'-N-Desmethyl-3'-N-(2-furyl)methyl-11-deoxy-11-[carboxy-(3-chloro-4-fluorophenethylamino)]-6-O-methyl-erythromycin A 11,12-(cyclic carbamate)

The title compound was prepared in accordance with the method described in Example 19 but substituting 3-chloro-4-fluorophenethylamine for 4-chlorophenethylamine and 2-furaldehyde for cyclobutanone: MS (APCI) (M+H)$^+$ at m/z 995.

EXAMPLE 46

3'-N-Desmethyl-3'-N-[2-(5-hydroxymethyl)furyl]
methyl-11-deoxy-11-[carboxy-(3-chloro-4-
fluorophenethylamino)]-6-O-methyl-erythromycin A
11,12-(cyclic carbamate)

The title compound was prepared in accordance with the method described in Example 19 but substituting 3-chloro-4-fluorophenethylamine for 4-chlorophenethylamine and 5-hydroxymethyl-2-furaldehyde for cyclobutanone: MS (APCI) (M+H)$^+$ at m/z 1025.

EXAMPLE 47

3'-N-Desmethyl-3'-N-(2-pyridyl)methyl-11-deoxy-
11-[carboxy-(3-chloro-4-fluorophenethylamino)]-6-
O-methyl-erythromycin A 11,12-(cyclic carbamate)

The title compound was prepared in accordance with the method described in Example 19 but substituting 3-chloro-4-fluorophenethylamine for 4-chlorophenethylamine and 2-pyridylcarboxaldehyde for cyclobutanone: MS (APCI) (M+H)$^+$ at m/z 1006.

EXAMPLE 48

3'-N-Desmethyl-3'-N-[2-(6-methyl)pyridyl]methyl-
11-deoxy-11-[carboxy-(3-chloro-4-
fluorophenethylamino)]-6-O-methyl-erythromycin A
11,12-(cyclic carbamate)

The title compound was prepared in accordance with the method described in Example 19 but substituting 3-chloro-4-fluorophenethylamine for 4-chlorophenethylamine and 6-methyl-2-pyridylcarboxaldehyde for cyclobutanone: MS (APCI) (M+H)$^+$ at m/z 1020.

EXAMPLE 49

3'-N-Desmethyl-3'-N-(4-hydroxyethoxybenzyl)-11-
deoxy-11-[carboxy-(3-chloro-4-
fluorophenethylamino)]-6-O-methyl-erythromycin A
11,12-(cyclic carbamate)

The title compound was prepared in accordance with the method described in Example 19 but substituting 3-chloro-4-fluorophenethylamine for 4-chlorophenethylamine and 4-hydroxyethoxybenzaldehyde for cyclobutanone: MS (APCI) (M+H)$^+$ at m/z 1065.

EXAMPLE 50

3'-N-Desmethyl-3'-N-(3-methylthio)butyl-11-deoxy-
11-[carboxy-(3-chloro-4-fluorophenethylamino)]-6-
O-methyl-erythromycin A 11,12-(cyclic carbamate)

The title compound was prepared in accordance with the method described in Example 19 but substituting 3-chloro-4-fluorophenethylamine for 4-chlorophenethylamine and 3-methylthiobutyraldehyde for cyclobutanone: MS (APCI) (M+H)$^+$ at m/z 1017.

EXAMPLE 51

3'-N-Desmethyl-3'-N-(4,4,4-trifluorobutyl)-11-
deoxy-11-[carboxy-(3-chloro-4-
fluorophenethylamino)]-6-O-methyl-erythromycin A
11,12-(cyclic carbamate)

The title compound was prepared in accordance with the method described in Example 19 but substituting 3-chloro-4-fluorophenethylamine for 4-chlorophenethylamine and 4,4,4-trifluorobutyraldehyde for cyclobutanone: MS (APCI) (M+H)$^+$ at m/z 1025.

EXAMPLE 52

3'-N-Desmethyl-3'-N-cyclobutyl-11-deoxy-11-
[carboxy-(4-chloro-3-fluorophenethylamino)]-6-O-
methyl-erythromycin A 11,12-(cyclic carbamate)

The title compound was prepared in accordance with the method described in Example 19 but substituting 4-chloro-3-fluorophenethylamine for 4-chlorophenethylamine: MS (APCI) (M+H)$^+$ at m/z 969.

EXAMPLE 53

3'-N-Desmethyl-3'-N-isopropyl-11-deoxy-11-
[carboxy-(3,4-difluorophenethylamino )]-6-O-
methyl-erythromycin A 11,12-(cyclic carbamate)

The title compound was prepared in accordance with the method described in Example 19 but substituting 3,4-difluorophenethylamine for 4-chlorophenethylamine and acetone for cyclobutanone: MS (APCI) (M+H)$^+$ at m/z 941.

EXAMPLE 54

3'-N-Desmethyl-3'-N-propyl-11-deoxy-11-[carboxy-
[3 4-(1,4-dioxano)phenethylamino)]}-6-O-methyl-
erythromycin A 11,12-(cyclic carbamate)

The title compound was prepared in accordance with the method described in Example 19 but substituting 3,4-(1,4-dioxano)phenethylamine for 4-chlorophenethylamine and propanal for cyclobutanone: MS (APCI) (M+H)$^+$ at m/z 963.

EXAMPLE 55

3'-N-Desmethyl-3'-N-cyclopropylmethyl-11-deoxy-
11-[carboxy-(3,4-dichlorophenethylamino)]-6-O-
methyl-erythromycin A 11,12-(cyclic carbamate)

The title compound was prepared in accordance with the method described in Example 19 but substituting 3,4-dichlorophenethylamine for 4-chlorophenethylamine and cyclopropanecarboxaldehyde for cyclobutanone: MS (APCI) (M+H)$^+$ at m/z 985.

EXAMPLE 56

3'-N-Desmethyl-3'-N-[3-(methylsulfoxy)propyl]-11-
deoxy-11-[carboxy-(3,4-dichlorophenethylamino)]-
6-O-methyl-erythromycin A 11,12-(cyclic
carbamate)

The title compound was prepared in accordance with the method described in Example 19 but substituting 3,4-dichlorophenethylamine for 4-chlorophenethylamine and 3-(methylsulfoxy)propanal for cyclobutanone followed by oxidation to the sulfoxide: MS (APCI) (M+H)$^+$ at m/z 1035.

EXAMPLE 57

3'-N-Desmethyl-3'-N-ethylthiourea-11-deoxy-11-
[carboxy-(3,4-dichlorophenethylamino)]-6-O-
methyl-erythromycin A 11,12-(cyclic carbamate)

3-Amino derivative 11 (0.36 g, 0.39 mmol) was dissolved in 10 mL of CHCl$_3$ and treated with 0.39 mmol derivative of ethyl isothiocyanate and the reaction stirred at ambient temperature. After 24 h the reaction was partitioned between EtOAC (100 mL) and the organic phase was washed with $NaHCO_3$ (sat., 3×100 mL), brine (100 mL) prior to drying ($Na_2SO_4$) and concentrating. The title compound was isolated by purification on a silica gel column; MS (APCI) $(M+H)^+$ at m/z 1018.

EXAMPLE 58

3'-N-Desmethyl-3'-N-[2-(5-hydroxymethyl)furyl] methyl-11-deoxy-11-[carboxy-(3,4-dichlorophenethylamino)]-6-O-methyl-erythromycin A 11,12-(cyclic carbamate)

The title compound was prepared in accordance with the method described in Example 19 but substituting 3,4-dichlorophenethylamine for 4-chlorophenethylamine and 5-hydroxymethyl-2-furaldehyde for cyclobutanone: MS (APCI) $(M+H)^+$ at m/z 1041.

EXAMPLE 59

3'-N-Desmethyl-3'-N-cyclopropylmethyl-11-deoxy-11-[carboxy-(α,α-cyclopropyl-3,4-dichlorophenethylamino)]-6-O-methyl-erythromycin A 11,12-(cyclic carbamate)

The title compound was prepared in accordance with the method described in Example 19 but substituting α,α-cyclopropyl-3,4-dichlorophenethylamine for 4-chlorophenethylamine and cyclopropanecarboxaldehyde for cyclobutanone: MS (APCI) $(M+H)^+$ at m/z 1011.

EXAMPLE 60

3'-N-Desmethyl-3'-N-propyl-11-deoxy-11-[carboxy-(4-chloroanilinoethylamino)]-6-O-methyl-erythromycin A 11,12-(cyclic carbamate)

Step 1: Preparation of 4-chloroanilino ethylamine

The hydrochloride salt of 4-chloroaniline (6.2 g, 38 mmol) and 2-oxazolidone (3.29 g, 38 mmol) was suspended in a minimal amount of di(ethyleneglycol)methyl ether and the resulting suspension heated at 160° C. After 4 h $CO_2$ evolution ceased and the reaction mixture was cooled to ambient temperature. The resulting solid was crystallized from EtOH/ether to yield 4.6 g (58%) of 4-chloroanilinoethylamine as its HCl salt. MS (CI) $(M+H)^+$ at m/z 171. The free amine was prepared by partitioning the HCl salt between $CH_2Cl_2$ and $NaHCO_3$ (sat.), drying the organic layer ($Na_2SO_4$), filtering and concentrating.

Step 2: 3'-N-Desmethyl-3'-N-propyl-11-deoxy-11-[carboxy-(4-chloroanilinoethylamino)]-6-O-methyl-erythromycin A 11,12-(cyclic carbamate)

The title compound was prepared in accordance with the method described in Example 19 but substituting 4-chloroanilinoethylamine obtained in step 1 for 4-chlorophenethylamine and propanal for cyclobutanone: MS (APCI) $(M+H)^+$ at m/z 954.

EXAMPLE 61

3'-N-Desmethyl-3'-N-pentyl-11-deoxy-11-[carboxy-(4-chloroanilinoethylamino)]-6-O-methyl-erythromycin A 11,12-(cyclic carbamate)

Step 1: Preparation of 4-chloroanilino ethylamine

The hydrochloride salt of 4-chloroaniline (6.2 g, 38 mmol) and 2-oxazolidone (3.29 g, 38 mmol) was suspended in a minimal amount of di(ethyleneglycol)methyl ether amd the resulting suspension heated at 160° C. After 4 h $CO_2$ evolution ceased and the reaction mixture was cooled to ambient temperature. The resulting solid was crystallized from EtOH/ether to yield 4.6 g (58%) of 4-chloroanilinoethylamine as its HCl salt. MS CI $(M+H)^+$ at m/z 171. The free amine was prepared by partitioning the HCl salt between $CH_2Cl_2$ and $NaHCO_3$ (sat.), drying the organic layer ($Na_2SO_4$), filtering and concentrating.

Step 2: 3'-N-Desmethyl-3'-N-propyl-11-deoxy-11-[carboxy-(4-chloroanilinoethylamino)]-6-O-methyl-erythromycin A 11,12-(cyclic carbamate)

The title compound was prepared in accordance with the method described in Example 19 but substituting 4-chloroanilinoethylamine obtained in step 1 for 4-chlorophenethylamine and propanal for cyclobutanone: MS (APCI) $(M+H)^+$ at m/z 980.

EXAMPLE 62

3'-N-Desmethyl-3'-N-isopropyl-11-deoxy-11-[carboxy-(3,4-difluorophenethylamino)]-6-O-methyl-erythromycin A 11,12-(cyclic carbamate)

This material was prepared in a manner analogous to that used for the preparation of Example 19 but substituting 3,4-difluorophenethylamine for 4-chlorophenethylamine and acetone for cyclobutanone: MS (APCI) $(M+H)^+$ at m/z 941.

EXAMPLE 63

3'-N-Desmethyl-3'-N-(2-imidazolyl)methyl-11-deoxy-11-[carboxy-(3,4-dichlorophenethylamino)]-6-O-methyl-erythromycin A 11,12-(cyclic carbamate)

The title compound was prepared in accordance with the method described in Example 1 but substituting imidazole-2-carboxaldehyde for cyclopentanone: MS (APCI) $(M+H)^+$ at m/z 1013.

EXAMPLE 64

3'-N-Desmethyl-3'-N-(3-pyridyl)methyl-11-deoxy-11-[carboxy-(3,4-dichlorophenethylamino)]-6-O-methyl-erythromycin A 11,12-(cyclic carbamate)

The title compound was prepared in accordance with the method described in Example 1 but substituting pyridyl-3-carboxaldehyde for cyclopentanone: MS (APCI) $(M+H)^+$ at m/z 1022.

EXAMPLE 65

3'-N-Desmethyl-3'-N-(2-pyridyl)methyl-11-deoxy-11-[carboxy-(3,4-dichlorophenethylamino)]-6-O-methyl-erythromycin A 11,12-(cyclic carbamate)

The title compound was prepared in accordance with the method described in Example 1 but substituting pyridyl-2-carboxaldehyde for cyclopentanone: MS (APCI) $(M+H)^+$ at m/z 1022.

EXAMPLE 66

3'-N-Desmethyl-3'-N-[(5-nitro-2-thienyl]methyl-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 5-nitrothiopene-2-carboxaldehyde for cyclopropanecarboxaldehyde: MS (APCI) (M+H)+ at m/z 1072.

EXAMPLE 67

3'-N-Desmethyl-3'-N-[5-(4-chlorophenyl)-2-furylmethyl]-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 5-(4-chlorophenyl)-2-furaldehyde for cyclopropanecarboxaldehyde: MS (APCI) (M+H)+ at m/z 1123.

EXAMPLE 68

3'-N-Desmethyl-3'-N-[5-nitro-2-furylmethyl]-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 5-nitro-2-furaldehyde for cyclopropanecarboxaldehyde: MS (APCI) (M+H)+ at m/z 1059.

EXAMPLE 69

3'-N-Desmethyl-3'-N-[2,5-dimethoxy-3-tetrahydrofurylmethyl]-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 2,5-dimethoxy-3-tetrahydrofuraldehyde for cyclopropanecarboxaldehyde: MS (APCI) (M+H)+ at m/z 1075.

EXAMPLE 70

3'-N-Desmethyl-3'-N-[6-methyl-2-pyridylmethyl]-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 6-methyl-pyridyl-2-carboxaldehyde for cyclopropanecarboxaldehyde: MS (APCI) (M+H)+ at m/z 1036.

EXAMPLE 71

3'-N-Desmethyl-3'-N-(4,4,4-trifluorobutyl)-11-deoxy-11-[carboxy-(3,4-dichlorophenethylamino)]-6-O-methyl-erythromycin A 11,12-(cyclic carbamate)

This material was prepared in a manner analogous to that used for the preparation of Example 55 but substituting 4,4,4-trifluorobutyraldehyde for cyclopropanecarboxaldehyde: MS (APCI) (M+H)+ at m/z 1041.

EXAMPLE 72

3'-N-Desmethyl-3'-N-(1-bromo-2-napthylmethyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 1-bromo-2-naphthylcarboxaldehyde for cyclopropanecarboxaldehyde: MS (APCI) (M+H)+ at m/z 1149.

EXAMPLE 73

3'-N-Desmethyl-3'-N-(4-methyl-1-napthylmethyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 4-methyl-1-naphthylcarboxaldehyde for cyclopropanecarboxaldehyde: MS (APCI) (M+H)+ at m/z 1085.

EXAMPLE 74

3'-N-Desmethyl-3'-N-(4-dimethylamino-1-napthylmethyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 4-dimethylamino-1-naphthylcarboxaldehyde for cyclopropanecarboxaldehyde: MS (APCI) (M+H)+ at m/z 1114.

EXAMPLE 75

3'-N-Desmethyl-3'-N-(2-furylmethyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 2-furaldehyde for cyclopropanecarboxaldehyde: MS (APCI) (M+H)+ at m/z 1011.

EXAMPLE 76

3'-N-Desmethyl-3'-N-[3-(4-pyridyl)propyl]-11-deoxy-11-[carboxy-(3,4-dichlorophenethylamino)]-6-O-methyl-erythromycin A 11,12-(cyclic carbamate)

This material was prepared in a manner analogous to that used for the preparation of Example 1 but substituting 4-pyridylpropanal for cyclopentanone. The crude product was purified on a silica gel column (CHCl$_3$→MeOH:CHCl$_3$, 5:95) to yield a crystalline solid; mp 144–5° C.; IR (film) ν 3315, 2968, 2937, 1754, 1733, 1603, 1457, 1417, 1168, 1066, 1011, 1000 cm$^{-1}$; $^{13}$C NMR (CDCl$_3$) δ 216.27, 176.37, 157.16, 150.72, 149.67, 146.79, 139.25, 132.14, 130.99, 130.24, 130.10, 128.37, 102.76, 96.15, 82.77, 80.20, 78.88, 77.89, 77.83, 76.22, 72.67, 70.71, 68.77, 65.78, 65.58, 60.31, 52.69, 50.64, 49.46, 45.48, 45.24, 44.77, 39.06, 39.01, 38.96, 36.76, 34.80, 32.59, 29.71, 28.63, 21.87, 21.44, 21.38, 20.14, 18.86, 18.66, 16.01, 14.18, 14.10, 10.22, 9.02. MS (APCI) (M+H)+ at m/z 1052; Anal. Calcd for C$_{54}$H$_{81}$Cl$_2$ N$_3$O$_{13}$: C, 61.70; H, 7.77; N, 4.00. Found: C, 61.56; H, 7.78; N, 4.03.

EXAMPLE 77

3'-N-Desmethyl-3'-N-[3-(2-pyridyl)propyl]-11-deoxy-11-[carboxy-(3,4-dichlorophenethylamino)]-6-O-methyl-erythromycin A 11,12-(cyclic carbamate)

This material was prepared in a manner analogous to that used for the preparation of Example 1 but substituting 3-(2-pyridyl)propanal for cyclopentanone. The crude product was purified on a silica gel column (CHCl$_3$→MeOH:CHCl$_3$, 5:95) to yield an amorphous solid: IR (film) ν 3446, 2970, 2937, 1756, 1458, 1167, 1052, 1011, 998 cm$^{-1}$; $^{13}$C NMR (CDCl$_3$) δ 216.29, 176.44, 157.19, 149.14, 139.31, 136.42, 132.19, 131.04, 130.26, 130.15, 128.45, 128.40, 122.78, 121.05, 102.97, 96.22, 82.83, 80.17, 78.99, 78.00, 77.94, 76.27, 72.66, 70.67, 68.81, 65.83, 65.68, 60.41, 53.38, 52.83, 50.66, 49.48, 45.53, 45.32, 44.83, 39.15, 39.02, 36.58, 35.57, 34.89, 32.64, 29.73, 28.15, 21.92, 21.47, 21.44, 20.18, 18.88, 18.70, 16.01, 14.22, 14.12, 10.23, 9.02. MS (APCI) (M+H)$^+$ at m/z 1052; Anal. Calcd for C$_{54}$H$_{81}$Cl$_2$ N$_3$O$_{13}$: C, 61.70; H, 7.77; N, 4.00. Found: C, 61.69; H, 7.62; N, 3.87.

EXAMPLE 78

3'-N-Desmethyl-3'-N-[4-(4-pyridyl)butyl]-11-deoxy-11-[carboxy-(3,4-dichlorophenethylamino)]-6-O-methyl-erythromycin A 11,12-(cyclic carbamate)

This material was prepared in a manner analogous to that used for the preparation of Example 1 but substituting 4-(4-pyridyl)butanal for cyclopentanone. The crude product was purified on a silica gel column (CHCl$_3$→MeOH:CHCl$_3$, 5:95) and crystallized from acetonitrile: mp 192–3° C.; IR (film) ν 3416, 2969, 2936, 1755, 1733, 1457, 1168, 1067, 1011, 1000 cm$^{-1}$; $^{13}$C NMR (CDCl$_3$) δ 216.27, 176.40, 157.15, 151.04, 149.65, 139.25, 132.13, 130.99, 130.24, 130.10, 128.37, 123.85, 102.76, 96.25, 82.77, 80.22, 78.91, 78.00, 77.87, 76.26, 72.68, 70.66, 68.74, 65.79, 65.55, 60.31, 52.93, 50.64, 49.44, 45.48, 45.27, 44.78, 39.07, 38.96, 36.86, 35.01, 34.92, 34.84, 32.60, 32.12, 29.66, 27.62, 21.87, 21.44, 21.38, 20.15, 18.86, 18.66, 16.03, 14.20, 14.10, 10.22, 9.02. MS (APCI) (M+H)$^+$ at m/z 1066; Anal. Calcd for C$_{55}$H$_{83}$Cl$_2$ N$_3$O$_{13}$: C, 62.02; H, 7.85; N, 3.94. Found: C, 62.31; H, 7.80; N, 3.77.

EXAMPLE 79

3'-N-Desmethyl-3'-N-[3-(3-pyridyl)propyl]-11-deoxy-11-[carboxy-(3,4-dichlorophenethylamino)]-6-O-methyl-erythromycin A 11,12-(cyclic carbamate)

This material was prepared in a manner analogous to that used for the preparation of Example 1 but substituting 3-(3-pyridyl)propanal for cyclopentanone. The crude product was purified on a silica gel column (CHCl$_3$→MeOH:CHCl$_3$, 2:98). IR (MIC) ν 2971, 2936, 1759, 1735, 1457, 1423, 1167, 1128, 1067, 1053, 1013 cm$^{-1}$. $^{13}$C NMR (CDCl$_3$) δ 216.32, 176.43, 157.20, 149.78, 147.38, 139.33, 137.14, 135.82, 132.16, 131.03, 130.27, 130.12, 128.42, 123.34, 102.90, 96.23, 82.83, 80.20, 78.95, 77.97, 77.93, 76.23, 72.72, 70.77, 68.86, 65.82, 65.33, 60.35, 52.59, 50.67, 49.51, 45.53, 45.29, 44.81, 39.12, 39.07, 38.99, 36.77, 34.91, 32.63, 30.48, 29.66, 29.53, 21.91, 21.46, 21.43, 20.18, 18.89, 18.71, 16.04, 14.20, 14.13, 10.25, 9.04. MS (APCI) m/z 1038 (M+H)$^+$. Anal. Calcd. for C$_{53}$H$_{79}$Cl$_2$N$_3$O$_{13}$: C, 61.37; H, 7.69; N, 4.05. Found: C, 61.61; H, 7.81; N, 3.98.

EXAMPLE 80

3'-N-Desmethyl-3'-N-[3-(3-pyridyl)propyl]-11-deoxy-11-[carboxy-(3-chloro-4-fluorophenethylamino)]-6-O-methyl-erythromycin A 11,12-(cyclic carbamate)

This material was prepared in a manner analogous to that used for the preparation of Example 79 but substituting 3-chloro-4-fluorophenethylamine for 3,4-dichlorophenethylamine. The crude product was purified on a silica gel column (CHCl$_3$→MeOH:CHCl$_3$, 2:98). IR (MIC) ν 2971, 2937, 1759, 1735, 1502, 1458, 1423, 1168, 1105, 1055, 1012, 997 cm$^{-1}$. $^{13}$C NMR (CDCl$_3$) δ 216.31, 176.42, 157.22, 149.83, 147.45, 135.80, 131.07, 128.53, 123.35, 102.95, 96.25, 82.81, 80.28, 78.96, 78.00, 76.30, 72.74, 70.80, 68.90, 65.86, 65.39, 60.39, 52.66, 50.69, 49.52, 45.56, 45.33, 45.04, 39.16, 39.11, 39.03, 36.80, 34.92, 32.54, 30.52, 29.71, 21.95, 21.48, 21.43, 20.20, 18.91, 18.71, 16.04, 14.25, 14.15, 10.28, 9.07. MS (APCI) m/z 1034 (M+H)$^+$. Anal. Calcd. for C$_{54}$H$_{81}$ClFN$_3$O$_{13}$: C, 62.68; H, 7.91; N, 4.06. Found: C, 62.76; H, 7.87; N, 3.92.

EXAMPLE 81

3'-N-Desmethyl-3'-N-[3-(4-pyridyl)propyl]-11-deoxy-11-[carboxy-(3-chloro-4-fluorophenethylamino)]-6-O-methyl-erythromycin A 11,12-(cyclic carbamate)

This material was prepared in a manner analogous to that used for the preparation of Example 76 but substituting 3-chloro-4-fluorophenethylamine for 3,4-dichlorophenethylamine The crude product was purified on a silica gel column (CHCl$_3$→MeOH:CHCl$_3$, 5:95) and crystallized from acetonitrile: mp 162–3° C.; IR (film) ν 3312, 2972, 2936, 1752, 1459, 1168, 1063, 1010 cm$^{-1}$; $^{13}$C NMR (CDCl$_3$) δ 216.22, 176.33, 157.10, 156.65 (d, J=247 Hz), 150.82, 149.62, 146.69, 135.94 (d, J=3.7 Hz), 130.93, 128.47 (d, J=6.7 Hz), 126.09, 123.69, 120.39 (d, J=17.4 Hz), 116.22 (d, J=20.4 Hz), 102.75, 96.10, 82.70, 80.06, 78.83, 77.81, 77.79, 76.14, 72.59, 70.67, 68.75, 65.67, 65.50, 60.23, 52.50, 50.56, 49.39, 45.43, 45.18, 44.90, 39.00, 38.97, 38.89, 36.66, 34.76, 32.53, 32.40, 29.53, 28.77, 21.81, 21.35, 21.33, 20.07, 18.79, 18.61, 15.92, 14.11, 14.02, 10.16, 8.92. MS (APCI) at m/z 1034 (M+H)$^+$. Anal. Calcd. for C$_{54}$H$_{81}$ClFN$_3$O$_{13}$: C, 62.68; H, 7.89; N, 4.06. Found: C, 62.40; H, 7.53; N, 3.89.

EXAMPLE 82

3'-N-Desmethyl-3'-N-[3-(2-pyridyl)propyl]-11-deoxy-11-[carboxy-(3-chloro-4-fluorophenethylamino)]-6-O-methyl-erythromycin A 11,12-(cyclic carbamate)

This material was prepared in a manner analogous to that used for the preparation of example 77 but substituting 3-chloro-4-fluorophenethylamine for 3,4-dichlorophenethylamine The crude product was purified on a silica gel column (CHCl$_3$→MeOH:CHCl$_3$, 5:95) and crystallized from acetonitrile: mp 167–9° C.; IR (film) ν 3266, 2971, 2937, 1754, 1459, 1167, 1064, 1010, cm$^{-1}$; $^{13}$C NMR (CDCl$_3$) δ 216.22, 176.33, 157.10, 156.8 (d, J=247 Hz), 149.15, 136.4, 136.03, 131.04, 128.56 (d, J=10 Hz), 122.84, 121.08, 120.40 (d, J=17 Hz), 116.34 (d, J=28 Hz), 102.84, 96.20, 82.79, 80.08, 78.96, 77.95, 77.92, 76.26, 72.65, 70.61, 68.80, 65.82, 65.68, 60.34, 52.56, 50.67, 49.49, 45.53, 45.30, 45.01, 39.11, 39.01, 36.62, 35.54, 34.87, 32.52, 29.65, 28.54, 21.93, 21.49, 21.43, 20.18, 18.89, 18.71, 16.04, 14.25, 14.14, 10.27, 9.06. MS (APCI) at m/z 1034 (M+H)$^+$. Anal. Calcd. for C$_{54}$H$_{81}$ClFN$_3$O$_{13}$: C, 62.68; H, 7.89; N, 4.06. Found: C, 62.64; H, 7.81; N, 3.99.

EXAMPLE 83

3'-N-Desmethyl-3'-N-[4-(4-pyridyl)butyl]-11-deoxy-11-[carboxy-(3-chloro-4-fluorophenethylamino)]-6-O-methyl-erythromycin A 11,12-(cyclic carbamate)

This material was prepared in a manner analogous to that used for the preparation of Example 78 but substituting 3-chloro-4-fluorophenethylamine for 3,4-dichlorophenethylamine. The crude product was purified on a silica gel column (CHCl$_3$→MeOH:CHCl$_3$, 5:95) and crystallized from acetonitrile: mp 118–120° C.; IR (film) v 3437, 2971, 2938, 1755, 1459, 1167, 1055, 1011 cm$^{-1}$; $^{13}$C NMR (CDCl$_3$) δ 216.23, 176.40, 157.17, 156.78 (d, J=247 Hz), 151.07, 149.71, 136.03 (d, J=5 Hz), 131.02, 128.52 (d, J=5 Hz), 123.82, 120.61 (d, J=14 Hz), 116.31 (d, J=28 Hz), 102.89, 96.28, 82.76, 80.24, 78.98, 78.09, 77.92, 76.30, 72.71, 70.75, 68.84, 65.80, 65.62, 60.39, 52.91, 50.64, 49.45, 45.50, 45.32, 45.01, 39.15, 39.12, 39.01, 36.85, 35.05, 34.89, 32.51, 29.66, 29.61, 27.66, 21.92, 21.45, 21.41, 20.16, 18.86, 18.67, 16.02, 14.22, 14.09, 10.24, 9.01. MS (APCI) m/z 1048 (M+H)$^+$. Anal. Calcd. for C$_{54}$H$_{81}$ClFN$_3$O$_{13}$: C, 62.99; H, 7.98; N, 4.01. Found: C, 63.14; H, 7.95; N, 3.80.

EXAMPLE 84

3'-N-Desmethyl-3'-N-[4-(6-methyl)-2-pyridyl]butyl-11-deoxy-11-[carboxy-(3-chloro-4-fluorophenethylamino )]-6-O-methyl-erythromycin A 11,12-(cyclic carbamate)

This material was prepared in a manner analogous to that used for the preparation of Example 80 but substituting [4-(6-methyl)-2-pyridyl]butanal for 3-(3-pyridyl)propanal. The crude product was purified on a silica gel column (CHCl$_3$→MeOH:CHCl$_3$, 2:98) yielding the crystalline product: mp=68–78° C. (acetonitrile); IR (MIC), v 2971, 2938, 1758, 1734, 1457, 1168, 1105, 1054, 1013 cm$^{-1}$. $^{13}$C NMR (CDCl$_3$) δ 216.31, 176.45, 157.78, 157.20, 136.67, 136.54, 136.09 (d, J=3.7 Hz), 131.07, 128.58 (d, J=7.3 Hz), 120.53, 119.62 (d, J=20.8 Hz), 116.35 (d, J=20.8 Hz), 102.93, 96.21, 82.81, 80.15, 78.99, 77.95, 77.63, 77.22, 76.53, 76.49, 76.30, 72.69, 70.70, 68.92, 65.84, 65.78, 62.43, 60.40, 50.69, 49.51, 45.56, 45.33, 45.04, 39.16, 39.11, 39.03, 38.34, 37.48, 36.86, 34.90, 32.54, 32.15, 27.70, 25.92, 24.54, 21.95, 21.50, 21.47, 20.19, 18.89, 18.71, 16.03, 14.23, 14.13, 10.26, 9.00. MS (APCI) m/z 1062 (M+H)$^+$. Anal. Calcd. for C$_{56}$H$_{85}$ClFN$_3$O$_{13}$·1.75 H$_2$O: C, 61.46; H, 8.15; N, 3.83. Found: C, 61.54; H, 7.86; N, 3.76.

EXAMPLE 85

3'-N-Desmethyl-3'-N-(1-methyl)[3-(4-hydroxy) phenyl]propyl-11-deoxy-11-[carboxy-(3,4-dichlorophenethylamino)]-6-O-methyl-erythromycin A 11,12-(cyclic carbamate)

This material was prepared in a manner analogous to that used for the preparation of Example 1 but substituting 4-(4-hydroxyphenyl)-2-butanone for cyclopentanone. The crude product was purified by crystallization from acetonitrile: mp 133–4° C.; IR (MIC) v 3396, 2971, 2937, 1760, 1735, 1458, 1168, 1053, 1012, 997 cm$^{-1}$; $^{13}$C NMR (CDCl$_3$) δ 216.49, 176.50, 176.45, 157.33, 154.19, 139.20, 133.81, 133.63, 132.14, 130.99, 130.30, 130.23, 130.10, 129.31, 129.21, 128.37, 115.27, 115.22, 102.89, 102.75, 96.23, 96.18, 82.94, 80.01, 78.98, 78.02, 77.94, 77.91, 76.21, 72.66, 72.58, 70.80, 70.44, 68.86, 68.71, 65.73, 64.97, 63.34, 60.41, 58.50, 55.95, 50.61, 49.45, 45.46, 45.28, 44.78, 39.12, 38.95, 37.69, 37.30, 34.83, 34.78, 33.79, 33.73, 33.64, 32.58, 32.38, 32.28, 31.83, 27.93, 23.53, 21.88, 21.45, 21.41, 20.16, 18.80, 18.64, 17.50, 16.00, 14.15, 14.06, 10.20, 8.94 (more signals than actual carbons due to a mixture of diastereomers); MS (APCI) (M+H)$^+$ at m/z 1079; Anal. Calcd for C$_{56}$H$_{84}$Cl$_2$ N$_2$O$_{14}$: C, 62.27; H, 7.84; N, 2.59. Found: C, 62.29; H, 7.67; N, 2.53.

EXAMPLE 86

3'-N-Desmethyl-3'-N-(1-methyl)[3-(4-hydroxy) phenyl]propyl-11-deoxy-11-[carboxy-(3-chloro-4fluorophenethylamino)]-6-O-methyl-erythromycin A 11,12-(cyclic carbamate)

This material was prepared in a manner analogous to that used for the preparation of Example 85 but substituting 3-chloro-4-fluorophenethylamine for 3,4-dichlorophenethylamine. The crude product was purified by crystallization from acetonitrile: mp 131–2° C.; IR (MIC) v 3373, 2971, 2937, 1733, 1457, 1168, 1055, 1012 cm$^{-1}$; $^{13}$C NMR (CDCl$_3$) δ 216.42, 176.47, 158.42, 157.30, 155.15, 154.03, 136.01, 135.96, 134.1, 133.9, 131.04, 129.41, 129.37, 129.31, 128.60, 128.50, 120.65, 120.40, 116.47, 116.18, 115.30, 115.24, 102.95, 102.82, 96.28, 96.25, 82.88, 80.09, 79.01, 78.12, 78.07, 77.99, 77.94, 77.19, 76.27, 72.71, 72.61, 70.85, 70.48, 68.89, 68.76, 65.80, 65.04, 63.53, 60.42, 58.45, 56.05, 50.64, 49.48, 45.51, 45.35, 45.01, 39.17, 39.00, 37.68, 37.34, 34.88, 34.81, 33.79, 33.66, 32.51, 32.40, 32.33, 31.70, 29.68, 27.96, 21.92, 21.54, 21.50, 21.42, 20.19, 18.85, 18.67, 17.63, 17.55, 16.03, 14.20, 14.09, 10.25, 8.99 (more signals than actual carbons due to a mixture of diastereomers); MS (APCI) (M+H)$^+$ at m/z 1063; Anal. Calcd for C$_{56}$H$_{84}$ClFN$_2$O$_{14}$: C, 63.23; H, 7.96; N, 2.63. Found C, 63.45; H, 7.93; N, 2.48.

EXAMPLE 87

3'-N-Desmethyl-3'-N-[3-(6-methyl-2-pyridyl) propyl]-11-deoxy-11-[carboxy-(3-chloro-4-fluorophenethylamino)]-6-O-methyl-erythromycin A 11,12-(cyclic carbamate)

Preparation of 3-(6-Methyl-2-pyridyl)propyn-1-ol

Step 1a: Into a solution of 2-bromo-6-methylpyridine (3.0 g, 17.4 mmol) in trimethylamine/H$_2$O (30 mL/6 mL), LiCl (65 mg), CuBr (65 mg), and propargyl alcohol (1.06 g, 19 mmol) were added. Argon was slowly bubbled through reaction mixture for 15 min before an addition of Pd(PPh$_3$)$_4$ (150 mg). The reaction mixture was heated to reflux for 3 hrs under argon. After cooling to room temperature, the solvents were evaporated in vacuo and the brown residue was treated with 2 N NaOH. The water layer was extracted with CHCl$_3$ (3×), the organic layer was dried over MgSO$_4$ and concentrated in vacuo. The product was purified by column chromatography (silica gel, ethyl acetate) yielding a yellow solid (78%). MS (DCI) (M+H)$^+$ at m/z 148.

Step 1b: 3-(6-Methyl-2- pyridyl)propanol 3-(6-methyl -2-pyridyl)propyn-1-ol was dissolved in MeOH (100 mL) and PtO$_2$ (0.09 g) was added. The reaction mixture was hydrogenated at 4 atm for 30 min. The catalyst was filtered off and methanol evaporated in vacuo. The orange oily residue (2 g) was purified by column chromatography (silica gel, ethyl acetate) yielding a yellow oil (77%). MS (DCI) (M+H)$^+$ at m/z 152.

Step 1c: 3-(6-Methyl-2-pyridyl)propanal

A solution of DMSO (1.78 g, 22.9 mmol) in dichloromethane (4mL) was added dropwise over 3 min into solution of oxalyl chloride (11.3 mmol) in dichloromethane (6 mL) cooled to −78° C. under nitrogen. The reaction mixture was stirred for 5 min when 3-(6-methyl-2-pyridyl) propanol (1.57 g, 10.4 mmol) in dichloromethane (20 mL) was added over 5 min. The stirring continued for 20 min at −78° C. and triethylamine (8 ml) was added resulting in dark slurry. The cooling bath was removed and after 3 hr, the reaction mixture was quenched with brine followed by dichloromethane extraction (3×). After solvent removal, the dark residue was purified by column chromatography (silica gel, ethyl acetate) yielding a yellow oil (77%). MS (DCI) (M+H)+ at m/z 150.

Step 2: 3'-N-Desmethyl-3'-N-[3-(6-methyl-2-pyridyl) propyl]-11-deoxy-11-[carboxy-(3-chloro-4-fluorophenethylamino)]-6-O-methyl-erythromycin A 11,12-(cyclic carbamate)

The title compound was prepared in a manner analogous to that used for the preparation of example 80 but substituting 3-(6-methyl-2-pyridyl)propanal for 3-(3-pyridyl) propanal. The crude product was purified on a silica gel column (CHCl$_3$→MeOH:CHCl$_3$, 2:98) yielding the crystalline product: mp 165–173° C.; IR (MIC) ν 2970, 2936, 1756, 1731, 1501, 1458, 1170, 1104, 1092, 1061, 1012, 996 cm$^{-1}$. $^{13}$C NMR (CDCl$_3$) δ 215.02, 175.18, 159.96, 156.43, 155.89, 155.45 (d, J=247 Hz), 135.31, 134.73 (d, J=3.8 Hz), 129.72, 127.26 (d, J=6.8 Hz), 119.20, 119.19 (d, J=17.4 Hz), 118.24, 115.02 (d, J=21.2 Hz), 101.67, 94.89, 81.49, 78.71, 77.67, 76.61, 74.91, 71.31, 69.26, 67.53, 64.49, 64.45, 59.02, 50.88, 49.35, 48.17, 44.21, 43.98, 43.69, 37.86, 37.68, 35.42, 34.17, 33.55, 31.20, 28.31, 27.26, 23.07, 20.60, 20.15, 20.10, 18.87, 17.56, 17.40, 14.71, 12.90, 12.80, 8.95, 7.69. MS (APCI) m/z 1048 (M+H)+. Anal. Calcd. for C$_{55}$H$_{83}$ClFN$_3$O$_{13}$: C, 62.99; H, 7.98; N, 4.01. Found: C, 62.83; H, 8.09; N, 4.16.

EXAMPLE 88

3'-N-Desmethyl-3'-N-[3-(5-methyl-2-pyridyl) propyl]-11-deoxy-11[carboxy-(3-chloro-4-fluorophenethylamino)]-6-O-methyl-erythromycin A 11,12-(cyclic carbamate)

This material was prepared in a manner analogous to that used for the preparation of example 80 but substituting 3-(5-methyl-2-pyridyl)propanal for 3-(3-pyridyl)propanal. The crude product was purified on a silica gel column (CHCl$_3$→MeOH:CHCl$_3$, 2:98) yielding the crystalline product: mp 196–202° C.; IR (MIC) ν 2972, 2938, 1756, 1732, 1501, 1458, 1169, 1128, 1105, 1068, 1060, 1012, 997 cm$^{-1}$. $^{13}$C NMR (CDCl$_3$) δ 216.35, 176.49, 158.73, 157.21, 156.77 (d, J=247 Hz), 149.44, 137.02, 136.07, 136.06 (d, J=3.8 Hz), 131.04, 130.22, 128.59 (d, J=6.9 Hz), 122.21, 120.52 (d, J=17.4 Hz), 116.34 (d, J=21.2 Hz), 105.50, 103.01, 96.21, 82.82, 80.08, 79.00, 77.94, 76.23, 72.65, 70.67, 68.87, 65.78, 65.69, 60.35, 52.71, 50.68, 49.47, 45.55, 45.31, 45.01, 39.16, 39.14, 39.01, 36.56, 35.11, 34.88, 32.52, 29.61, 28.47, 21.93, 21.47, 20.19, 18.90, 18.72, 18.04, 16.04, 14.22, 14.13, 10.28, 9.00. MS (APCI) m/z 1048 (M+H)+. Anal. Calcd. for C$_{55}$H$_{83}$ClFN$_3$O$_{13}$: C, 62.99; H, 7.98; N, 4.01. Found: C, 62.40; H, 8.06; N, 4.13.

EXAMPLE 89

3'-N-Desmethyl-3'-N-(2-pyridyl)ethyl-11-deoxy-11-[carboxy-(3,4-dichlorophenethylamino)]-6-O-methyl-erythromycin A 11,12-(cyclic carbamate)

A solution of 11 described in Example 1 (0.150 g, 0.161 mmol), 2-vinylpyridine (0.085 g, 0.805 mmol) and acetic acid (0.048 g, 0.046 mL, 0.805 mmol) in methanol (3 mL) was heated to reflux for 4 days. The residue was partitioned between chloroform and saturated solution of NaHCO$_3$, the organic layer was dried over anhydrous magnesium sulfate and the solvents were evaporated in vacuo. The crude product was purified on a silica gel column (CHCl$_3$→MeOH:CHCl$_3$, 5:95) yielding crystalline product: mp 125–6° C. (acetonitrile); IR (MIC), ν 3452, 2972, 2938, 1760, 1735, 1459, 1168, 1055, 1012, 1000 cm$^{-1}$; MS (APCI) (M+H)+ at m/z 1036; Anal. Calcd for C$_{53}$H$_{79}$Cl$_2$ N$_3$O$_{13}$: C, 61.38; H, 7.68; N, 4.05. Found: C, 61.25; H, 7.57; N, 4.05.

EXAMPLE 90

3'-N-Desmethyl-3'-N-(2-pyridyl)ethyl-11-deoxy-11-[carboxy-(3-chloro-4-fluorophenethylamino)]-6-O-methyl-erythromycin A 11,12-(cyclic carbamate)

The title compound was prepared in a manner analogous to that used for the preparation of Example 89 but substituting 3-chloro-4-fluorophenethylamine for 3,4-dichlorophenethylamine. The crude product was purified on a silica gel column (CHCl$_3$→MeOH:CHCl$_3$, 5:95) yielding crystalline product: mp 200–202° C. (acetonitrile); IR (MIC) ν 3452, 2972, 2938, 1757, 1732, 1459, 1168, 1055, 1012, 1000 cm$^{-1}$; MS (APCI) (M+H)+ at m/z 1020.

EXAMPLE 91

3'-N-Desmethyl-3'-N-(4-hydroxybenzyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 4-hydroxybenzaldehyde for cyclopropanecarboxaldehyde: MS (APCI) (M+H)+ at m/z 1037.

EXAMPLE 92

3'-N-Desmethyl-3'-N-(4-pyridylmethyl)-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 4-pyridylcarboxaldehyde for cyclopropanecarboxaldehyde: MS (APCI) (M+H)+ at m/z 1022.

EXAMPLE 93

3'-N-Desmethyl-3'-N-[(3-methylthio)butyl]-11-deoxy-11-[carboxy-(3,4-dichlorophenethylamino)]-6-O-methyl-erythromycin A 11,12-(cyclic carbamate)

The title compound was prepared in accordance with the method described in Example 55 but substituting 3-(methylthio)butyraldehyde for cyclopropanecarboxaldehyde: MS (APCI) (M+H)+ at m/z 1033.

EXAMPLE 94

3'-N-Desmethyl-3'-N-(1-methylcyclopropyl)methyl-11-deoxy-11-[carboxy-(3,4-dichlorophenethylamino)]-6-O-methyl-erythromycin A 11,12-(cyclic carbamate)

The title compound was prepared in a manner analogous to that used for the preparation of Example 1 but substituting 2-methylcyclopropanecarboxaldehyde for cyclopropanecarboxaldehyde: MS (APCI) (M+H)+ at m/z 999.

EXAMPLE 95

3'-N-Desmethyl-3'-N-(1-methylcyclopropyl)methyl-11-deoxy-11-[carboxy-(3-chloro-4-fluorophenethylamino)]-6-O-methyl-erythromycin A 11,12-(cyclic carbamate)

The title compound was prepared in a manner analogous to that used for the preparation of Example 29 but substituting 2-methylcyclopropanecarboxaldehyde for cyclopropanecarboxaldehyde: MS (APCI) (M+H)+ at m/z 983.

EXAMPLE 96

3'-N-Desmethyl-3'-N-oxiranylmethyl-11-deoxy-11-[carboxy-(4-chlorophenethylamino)]-6-O-methyl-erythromycin A 11,12-(cyclic carbamate)

The title compound was prepared in a manner analogous to that used for the preparation of Example 57 but substituting epibromohydrin and triethylamine for ethyl isothiocyanate, and 4-chlorophenethylamine for 3,4-dichlorophenethylamine; MS (APCI) (M+H)+ at m/z 981.

EXAMPLE 97

3'-N-Desmethyl-3'-guanidino-11-deoxy-11[carboxy-(4-chlorophenethylamino)]-6-O-methyl-erythromycin A 11,12-(cyclic carbamate)

This material was prepared in a manner analogous to that used for the preparation of example 96 but substituting 3,5-dimethylpyrazolecarboxamidine for epibromohydrin: MS (APCI) (M+H)+ at m/z 939.

EXAMPLE 98

3'-N-Desmethyl-3'-N-2-(4,5-dihydroimidazolyl)-11-deoxy-11-[carboxy-(3,4-dichlorophenethylamino)]-6-O-methyl-erythromycin A 11,12-(cyclic carbamate)

The title compound was prepared in a manner analogous to that used for the preparation of Example 97 but substituting 3,5-dimethylpyrazolyl-4,5-dihydroimidazole for epibromohydrin: MS (APCI) (M+H)+ at m/z 965.

We claim:
1. A compound represented by the formula:

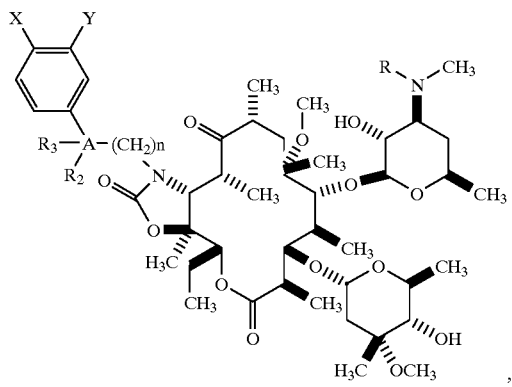

I or a pharmaceutically acceptable salt or ester thereof, wherein
A is selected from the group consisting of:
(a) —C,
(b) —N, and
(c) —O;
X and Y are independently at each occurrence selected from the group consisting of:
(a) hydrogen,
(b) halide,
(c) trifluoromethyl,
(d) alkoxy,
(e) alkyl,
(f) aryl, and
(g) substituted aryl;
R is selected from the group consisting of:
(a) $C_2$–$C_{20}$ alkyl,
(b) cycloalkyl,
(c) heterocycle,
(d) substituted heterocycle,
(e) alkylcycloalkyl,
(f) substituted alkylcycloalkyl,
(g) alkylaryl,
(f) alkylheterocycle,
(g) alkenyl,
(h) alkynyl,
(i) —C(S)—NHR$_4$, C(NR$_4$)—NHR$_4$, wherein R$_4$ is hydrogen, alkyl, or aryl; and
(j) —(CH$_2$)$_n$—C(CH$_2$)$_m$—R$_5$, wherein m is 2, 3, 4, or 5, and R$_5$ is alkyl, alkoxy, aryl, or substituted aryl;
R$_2$ and R$_3$ are independently at each occurrence
(a) hydrogen,
(b) methyl, or
R$_2$ and R$_3$ together with A to which they are attached may form a cyclic moiety, when
A is C;
R$_3$ is absent when A is N; and
n=1, 2 or 3.
2. The compound of claim 1, wherein R is alkyl, alkenyl, cycloalkyl, heterocycle, (heterocyclic)alkyl or alkylcycloalkyl; X and Y are independently at each occurrence chloro, fluoro, dioxalano, hydrogen, or alkoxy; A is —C or N; R$_2$ and R$_3$ are independently at each occurrence hydrogen or together they form cyclopropyl moiety and n is 1.
3. A compound of claim 1 selected from the group consisting of:
3'-N-desmethyl-3'-N-cyclopentyl-11-deoxy-11-[carboxy-(3,4-dichlorophenethylamino)]-6-O-methyl-erythromycin A 11,12-(cyclic carbamate);
3'-N-desmethyl-3'-N-cyclopropyl-11-deoxy-11-[carboxy-(3,4-dichlorophenethylamino)]-6-O-methyl-erythromycin A 11,12-(cyclic carbamate);
3'-N-desmethyl-3'-N-n-propyl-11-deoxy-11-[carboxy-(3,4-dichlorophenethylamino)]-6-O-methyl-erythromycin A 11,12-(cyclic carbamate);
3'-N-desmethyl-3'-N-cyclobutyl-11-deoxy-11-[carboxy-(3,4-dichlorophenethylamino)]-6-O-methyl-erythromycin A 11,12-(cyclic carbamate);
3'-N-desmethyl-3'-N-cyclohexyl-11-deoxy-11-[carboxy-(3,4-dichlorophenethylamino)]-6-O-methyl-erythromycin A 11,12-(cyclic carbamate);
3'-N-desmethyl-3'-N-isovaleryl-11-deoxy-11-[carboxy-(3,4-dichlorophenethylamino)]-6-O-methyl-erythromycin A 11,12-(cyclic carbamate);
3'-N-desmethyl-3'-N-(3-methylthiopropyl)-11-deoxy-11-[carboxy-(3,4-dichlorophenethylamino)]-6-O-methyl-erythromycin A 11,12-(cyclic carbamate);
3'-N-desmethyl-3'-N-(3-tetrahydrothienyl)-11-deoxy-11-[carboxy-(3,4-dichlorophenethylamino)]-6-O-methyl-erythromycin A 11,12-(cyclic carbamate);
3'-N-desmethyl-3'-N-(3,4-dimethylcyclopentyl)-11-deoxy-11-[carboxy-(3,4-dichlorophenethylamino)]-6-O-methyl-erythromycin A 11,12-(cyclic carbamate);

3'-N-desmethyl-3'-N-isopropyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclobutyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclopentyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-cyclohexyl-11-deoxy-11-[carboxy-(α,α-cyclopropyl-3,4-dichlorophenethylamino)]-6-O-methyl-erythromycin A 11,12-(cyclic carbamate);

3'-N-desmethyl-3'-N-n-propyl-11-deoxy-11[carboxy-(3,4-dioxolanophenethylamino)]-6-O-methyl-erythromycin A 11,12-(cyclic carbamate);

3'-N-desmethyl-3'-N-cyclopentyl-11-deoxy-11-[carboxy-(3,4-dioxolanophenethylamino)]-6-O-methyl-erythromycin A 11,12-(cyclic carbamate);

3'-N-desmethyl-3'-N-n-propyl-11-deoxy-11-[carboxy-(4-chloro-3-fluorophenethylamino)]-6-O-methyl-erythromycin A 11,12-(cyclic carbamate);

3'-N-desmethyl-3'-N-isopropyl-11-deoxy-11-[carboxy-(4-chloro-3-fluorophenethylamino)]-6-O-methyl-erythromycin A 11,12-(cyclic carbamate);

3'-N-desmethyl-3'-N-cyclopentyl-11-deoxy-11-[carboxy-(4-chloro-3-fluorophenethylamino)]-6-O-methyl-erythromycin A 11,12-(cyclic carbamate);

3'-N-desmethyl-3'-N-cyclobutylmethyl-11-deoxy-11-[carboxy-(4-chlorophenethylamino)]-6-O-methyl-erythromycin A 11,12-(cyclic carbamate);

3'-N-desmethyl-3'-N-cyclobutylmethyl-11-deoxy-11-[carboxy-(4-chlorophenethylamino)]-6-O-methyl-erythromycin A 11,12-(cyclic carbamate);

3'-N-desmethyl-3'-N-ethyl-11-deoxy-11-[carboxy-(4-chlorophenethylamino)]-6-O-methyl-erythromycin A 11,12-(cyclic carbamate);

3'-N-desmethyl-3'-N-isopropyl-11-deoxy-11-[carboxy-(4-chlorophenethylamino)]-6-O-methyl-erythromycin A 11,12-(cyclic carbamate);

3'-N-desmethyl-3'-N-cyclopentyl-11-deoxy-11-[carboxy-(4-chlorophenethylamino)]-6-O-methyl-erythromycin A 11,12-(cyclic carbamate);

3'-N-desmethyl-3'-N-cyclopentyl-11-deoxy-11-[carboxy-(3-chlorophenethylamino)]-6-O-methyl-erythromycin A 11,12-(cyclic carbamate);

3'-N-desmethyl-3'-N-n-propyl-11-deoxy-11-[carboxy-(3-chlorophenethylamino)]-6-O-methyl-erythromycin A 11,12-(cyclic carbamate);

3'-N-desmethyl-3'-N-cyclopentyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(3-chloro-4-fluorophenethylamino)]-6-O-methyl-erythromycin A 11,12-(cyclic carbamate);

3'-N-desmethyl-3'-N-isopropyl-11-deoxy-11-[carboxy-(3-chloro-4-fluorophenethylamino)]-6-O-methyl-erythromycin A 11,12-(cyclic carbamate);

3'-N-desmethyl-3'-N-cyclopropylmethyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[(carboxy-(3,4-difluorophenethylamino)]-6-O-methyl-erythromycin A 11,12-(cyclic carbamate);

3'-N-desmethyl-3'-N-cyclopentyl-11-deoxy-11-[(carboxy-(3,4-difluorophenethylamino)]-6-O-methyl-erythromycin A 11,12-(cyclic carbamate);

3'-N-desmethyl-3'-N-n-propyl-11-deoxy-11-[carboxy-(3,4-difluorophenethylamino)]-6-O-methyl-erythromycin A 11,12-(cyclic carbamate); and 3'-N-desmethyl-3'-N-cyclopropylmethyl-11-deoxy-11-[carboxy-(3,4-difluorophenethylamino)]-6-O-methyl-erythromycin A 11,12-(cyclic carbamate);

3'-N-desmethyl-3'-N-(4-pyridylmethyl)-11-deoxy-11-[carboxy-(4-chlorophenethylamino)]-6-O-methyl-erythromycin A 11,12-(cyclic carbamate)

3'-N-desmethyl-3'-N-(2-butyl)-11-deoxy-11-[carboxy-(4-chlorophenethylamino)]-6-O-methyl-erythromycin A 11,12-(cyclic carbamate)

3'-N-desmethyl-3'-N-(3-pentyl)-11-deoxy-11-[carboxy-(4-chlorophenethylamino)]-6-O-methyl-erythromycin A 11,12-(cyclic carbamate);

3'-N-desmethyl-3'-N-(cyclopropylmethyl)-11-deoxy-11-[carboxy-(4-chlorophenethylamino)]-6-O-methyl-erythromycin A 11,12-(cyclic carbamate)

3'-N-desmethyl-3'-N-(2-cyclopropylethyl)-11-deoxy-11-[carboxy-(4-chlorophenethylamino)]-6-O-methyl-erythromycin A 11,12-(cyclic carbamate)

3'-N-desmethyl-3'-N-propyl-11-deoxy-11-[carboxy-(4-methoxyphenethylamino)]-6-O-methyl-erythromycin A 11,12-(cyclic carbamate)

3'-N-desmethyl-3'-N-cyclopentyl-11-deoxy-11-[carboxy-(4-methoxyphenethylamino)]-6-O-methyl-erythromycin A 11,12-(cyclic carbamate);

3'-N-desmethyl-3'-N-propyl-11-deoxy-11-[carboxy-(3,4-dimethylphenethylamino)]-6-O-methyl-erythromycin A 11,12-(cyclic carbamate);

3'-N-desmethyl-3'-N-cyclopentyl-11-deoxy-11-[carboxy-(3-bromo-4-methoxyphenethylamino)]-6-O-methyl-erythromycin A 11,12-(cyclic carbamate);

3'-N-desmethyl-3'-N-propyl-11-deoxy-11-[carboxy-(3-bromo-4-methoxyphenethylamino)]-6-O-methyl-erythromycin A 11,12-(cyclic carbamate);

3'-N-desmethyl-3'-N-propyl-11-deoxy-11-[carboxy-(3-chloro-4-fluorophenethylamino)]-6-O-methyl-erythromycin A 11,12-(cyclic carbamate);

3'-N-desmethyl-3'-N-(2-furyl)methyl-11-deoxy-11-[carboxy-(3-chloro-4-fluorophenethylamino)]-6-O-methyl-erythromycin A 11,12-(cyclic carbamate);

3'-N-desmethyl-3'-N-[2-(5-hydroxymethyl)furyl]methyl-11-deoxy-11-[carboxy-(3-chloro-4-fluorophenethylamino)]-6-O-methyl-erythromycin A 11,12-(cyclic carbamate)

3'-N-desmethyl-3'-N-(2-pyridyl)methyl-11-deoxy-11-[carboxy-(3-chloro-4-fluorophenethylamino)]-6-O-methyl-erythromycin A 11,12-(cyclic carbamate);

3'-N-desmethyl-3'-N-[2-(6-methyl)pyridyl]methyl-11-deoxy-11-[carboxy-(3-chloro-4-fluorophenethylamino)]-6-O-methyl-erythromycin A 11,12-(cyclic carbamate)

3'-N-desmethyl-3'-N-(4-hydroxyethoxybenzyl)-11-deoxy-11-[carboxy-(3-chloro-4-fluorophenethylamino)]-6-O-methyl-erythromycin A 11,12-(cyclic carbamate);

3'-N-desmethyl-3'-N-(3-methylthio)butyl-11-deoxy-11-[carboxy-(3-chloro-4-fluorophenethylamino)]-6-O-methyl-erythromycin A 11,12-(cyclic carbamate);

3'-N-desmethyl-3'-N-(4,4,4-trifluorobutyl)-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(4-chloro-3-fluorophenethylamino)]-6-O-methyl-erythromycin A 11,12-(cyclic carbamate);

3'-N-desmethyl-3'-N-isopropyl-11-deoxy-11-[carboxy-(3,4-difluorophenethylamino)]-6-O-methyl-erythromycin A 11,12-(cyclic carbamate)

3'-N-desmethyl-3'-N-propyl-11-deoxy-11-[carboxy-[3,4-(1,4-dioxano)phenethylamino)]}-6-O-methyl-erythromycin A 11,12-(cyclic carbamate)

3'-N-desmethyl-3'-N-cyclopropylmethyl-11-deoxy-11-[carboxy-(3,4-dichlorophenethylamino)]-6-O-methyl-erythromycin A 11,12-(cyclic carbamate)

3'-N-desmethyl-3'-N-[3-(methylsulfoxy)propyl]-11-deoxy-11-[carboxy-(3,4-dichlorophenethylamino)]-6-O-methyl-erythromycin A 11,12-(cyclic carbamate)

3'-N-desmethyl-3'-N-ethylthiourea-11-deoxy-11-[carboxy-(3,4-dichlorophenethylamino)]-6-O-methyl-erythromycin A 11,12-(cyclic carbamate)

3'-N-desmethyl-3'-N-[2-(5-hydroxymethyl)furyl]methyl-11-deoxy-11-[carboxy-(3,4-dichlorophenethylamino)]-6-O-methyl-erythromycin A 11,12-(cyclic carbamate);

3'-N-desmethyl-3'-N-cyclopropylmethyl-11-deoxy-11-[carboxy-($\alpha,\alpha$-cyclopropyl-3,4-dichlorophenethylamino)]-6-O-methyl-erythromycin A 11,12-(cyclic carbamate)

3'-N-desmethyl-3'-N-propyl-11-deoxy-11-[carboxy-(4-chloroanilinoethylamino)]-6-O-methyl-erythromycin A 11,12-(cyclic carbamate)

3'-N-desmethyl-3'-N-cyclopentyl-11-deoxy-11-[carboxy-(4-chloroanilinoethylamino)]-6-O-methyl-erythromycin A 11,12-(cyclic carbamate)

3'-N-desmethyl-3'-N-isopropyl-11-deoxy-11-[carboxy-(3,4-difluorophenethylamino)]-6-O-methyl-erythromycin A 11,12-(cyclic carbamate)

3'-N-desmethyl-3'-N-(2-imidazolo)methyl-11-deoxy-11-[carboxy-(3,4-dichlorophenethylamino)]-6-O-methyl-erythromycin A 11,12-(cyclic carbamate)

3'-N-desmethyl-3'-N-(3-pyridyl)methyl-11-deoxy-11-[carboxy-(3,4-dichlorophenethylamino)]-6-O-methyl-erythromycin A 11,12-(cyclic carbamate)

3'-N-desmethyl-3'-N-(2-pyridyl)methyl-11-deoxy-11-[carboxy-(3,4-dichlorophenethylamino)]-6-O-methyl-erythromycin A 11,12-(cyclic carbamate)

3'-N-desmethyl-3'-N-[(5-nitro)-2-thienyl]methyl-11-deoxy-11-[carboxy-(3,4-dichlorophenethylamino)]-6-O-methyl-erythromycin A 11,12-(cyclic carbamate)

3'-N-desmethyl-3'-N-[5-(4-chlorophenyl)-2-furyl]methyl-11-deoxy-11-[carboxy-(3,4--dichlorophenethylamino)]-6-O-methyl-erythromycin A 11,12-(cyclic carbamate)

3'-N-desmethyl-3'-N-[5-nitro-2-furyl]methyl-11-deoxy-11-[carboxy-(3,4-dichlorophenethylamino)]-6-O-methyl-erythromycin A 11,12-(cyclic carbamate)

3'-N-desmethyl-3'-N-[2,5-dimethoxy-3-tetrahydrofuryl]methyl-11-deoxy-11-[carboxy-(3,4-dichlorophenethylamino)]-6-O-methyl-erythromycin A 11,12-(cyclic carbamate)

3'-N-desmethyl-3'-N-[6-methyl-2-pyridyl]methyl-11-deoxy-11-[carboxy-(3,4-dichlorophenethylamino)]-6-O-methyl-erythromycin A 11,12-(cyclic carbamate)

3'-N-desmethyl-3'-N-(4,4,4-trifluorobutyl)-11-deoxy-11-[carboxy-(3,4-dichlorophenethylamino)]-6-O-methyl-erythromycin A 11,12-(cyclic carbamate)

3'-N-desmethyl-3'-N-(1-bromo-2-napthyl)methyl-11-deoxy-11-[carboxy-(3,4-dichlorophenethylamino)]-6-O-methyl-erythromycin A 11,12-(cyclic carbamate)

3'-N-desmethyl-3'-N-(4-methyl-1-napthyl)methyl-11-deoxy-11-[carboxy-(3,4-dichlorophenethylamino)]-6-O-methyl-erythromycin A 11,12-(cyclic carbamate)

3'-N-desmethyl-3'-N-(4-dimethylamino-1-napthyl)methyl-11-deoxy-11-[carboxy-(3,4-dichlorophenethylamino)]-6-O-methyl-erythromycin A 11,12-(cyclic carbamate)

3'-N-desmethyl-3'-N-(2-furyl)methyl-11-deoxy-11-[carboxy-(3,4-dichlorophenethylamino)]-6-O-methyl-erythromycin A 11,12-(cyclic carbamate)

3'-N-desmethyl-[3'-N-3-(4-pyridyl)propyl]-11-deoxy-11-[carboxy-(3,4-dichlorophenethylamino)]-6-O-methyl-erythromycin A 11,12-(cyclic carbamate)

3'-N-desmethyl-3'-N-[3-(2-pyridyl)propyl]-11-deoxy-11-[carboxy-(3,4-dichlorophenethylamino)]-6-O-methyl-erythromycin A 11,12-(cyclic carbamate)

3'-N-desmethyl-3'-N-3-[4-(4-pyridyl)butyl]-11-deoxy-11-[carboxy-(3,4-dichlorophenethylamino)]-6-O-methyl-erythromycin A 11,12-(cyclic carbamate)

3'-N-desmethyl-3'-N-[3-(3-pyridyl)propyl]-11-deoxy-11-[carboxy-(3,4-dichlorophenethylamino)]-6-O-methyl-erythromycin A 11,12-(cyclic carbamate)

3'-N-desmethyl-3'-N-[(3-(3-pyridyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-[3-(4-pyridyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-[3-(2-pyridyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-[4-(4-pyridyl)butyl]-11-deoxy-11-[carboxy-(3-chloro-4-fluorophenethylamino)]-6-O-methyl-erythromycin A 11,12-(cyclic carbamate)

3'-N-desmethyl-3'-N-[4-(6-methyl-2-pyridyl)]butyl-11-deoxy-11-[carboxy-(3-chloro -4-fluorophenethylamino)]-6-O-methyl-erythromycin A 11,12-(cyclic carbamate)

3'-N-desmethyl-3'-N-[1-methyl-3-(4-hydroxyphenyl)propyl]-11-deoxy-11-[carboxy-(3,4-dichlorophenethylamino)]-6-O-methyl-erythromycin A 11,12-(cyclic carbamate)

3'-N-desmethyl-3'-N-[(1methyl)-3-(4-hydroxyphenyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-[3-(6-methyl-2-pyridyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-[3-(5-methyl-2-pyridyl)propyl]-11-deoxy-11-[carboxy-(3-chloro-4-fluorophenethylamino)]-6-O-methyl-erythromycin A 11,12-(cyclic carbamate)

3'-N-desmethyl-3'-N-(2-pyridylethyl)-11-deoxy-11-[carboxy-(3,4-dichlorophenethylamino)]-6-O-methyl-erythromycin A 11,12-(cyclic carbamate)

3'-N-desmethyl-3'-N-(2-pyridylethyl)-11-deoxy-11-[carboxy-(3-chloro-4-fluorophenethylamino)]-6-O-methyl-erythromycin A 11,12-(cyclic carbamate)

3'-N-desmethyl-3'-N-(4-hydroxybenzyl)-11-deoxy-11-[carboxy(3,4-dichlorophenethylamino)]-6-O-methyl-erythromycin A 11,12-(cyclic carbamate)

3'-N-desmethyl-3'-N-(4-pyridyl)methyl-11-deoxy-11-[carboxy-(3,4-dichlorophenethylamino)]-6-O-methyl-erythromycin A 11,12-(cyclic carbamate)

3'-N-desmethyl-3'-N-[(3-methylthio)butyl]-11-deoxy-11-[carboxy-(3,4-dichlorophenethylamino)]-6-O-methyl-erythromycin A 11,12-(cyclic carbamate)

3'-N-desmethyl-3'-N-(1-methylcyclopropyl)methyl-11-deoxy-11-[carboxy-(3,4-dichlorophenethylamino)]-6-O-methyl-erythromycin A 11,12-(cyclic carbamate);

3'-N-desmethyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3'-N-desmethyl-3'-N-oxiranylmethyl-11-deoxy-11-[carboxy-(3,4-dichlorophenethylamino)]-6-O-methyl-erythromycin A 11,12-(cyclic carbamate);

3'-N-desmethyl-3'-guanidino-11-deoxy-11-[carboxy-(3,4-dichlorophenethylamino)]-6-O-methyl-erythromycin A 11,12-(cyclic carbamate); and 3'-N-desmethyl3'-N-2-(4,5-dihydroimidazolyl)-11-deoxy-11-[carboxy-(3,4-dichlorophenethylamino)]-6-O-methyl-erythromycin A 11,12-(cyclic carbamate).

4. A compound according to claim 3 selected from the group consisting of:

3'-N-desmethyl-3'-N-cyclopentyl-11-deoxy-11-[carboxy-(3,4-dichlorophenethylamino)]-6-O-methyl-erythromycin A 11,12-(cyclic carbamate);

3'-N-desmethyl-3'-N-cyclopropyl-11-deoxy-11-[carboxy-(3,4-dichlorophenethylamino)]-6-O-methyl-erythromycin A 11,12-(cyclic carbamate);

3'-N-desmethyl-3'-N-n-propyl-11-deoxy-11-[carboxy-(3,4-dichlorophenethylamino)]-6-O-methyl-erythromycin A 11,12-(cyclic carbamate);

3'-N-desmethyl-3'-N-isopropyl-11-deoxy-11-[carboxy-(3-chloro-4-fluorophenethylamino)]-6-O-methyl-erythromycin A 11,12-(cyclic carbamate);

3'-N-desmethyl-3'-N-cyclopropylmethyl-11-deoxy-11-[carboxy-(3-chloro-4-fluorophenethylamino)]-6-O-methyl-erythromycin A 11,12-(cyclic carbamate);

3'-N-desmethyl-3'-N-cyclobutyl-11-deoxy-11-[carboxy-(3,4-difluorophenethylamino)]-6-O-methyl-erythromycin A 11,12-(cyclic carbamate);

3'-N-desmethyl-3'-N-cyclopentyl-11-deoxy-11-[carboxy-(3,4-difluorophenethylamino)]-6-O-methyl-erythromycin A 11,12-(cyclic carbamate);

3'-N-desmethyl-3'-N-n-propyl-11-deoxy-11-[carboxy-(3,4-difluorophenethylamino)]-6-O-methyl-erythromycin A 11,12-(cyclic carbamate); and 3'-N-desmethyl-3'-N-cyclopropylmethyl-11-deoxy-11-[carboxy-(3,4-difluorophenethylamino)]-6-O-methyl-erythromycin A 11,12-(cyclic carbamate).

5. A pharmaceutical composition for inhibiting the release of LH comprising a therapeutically effective amount of a compound according to claim 1 in combination with a pharmaceutically acceptable carrier.

6. A method of inhibiting LH release in a mammal in need of such treatment comprising administering to the mammal a therapeutically-effective amount of a compound according to claim 1.

7. A process for preparing a compound represented by the formula:

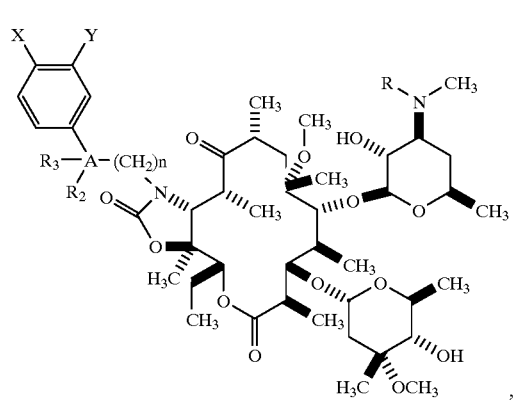

I or a pharmaceutically acceptable salt or ester thereof, wherein

A is selected from the group consisting of:

(a) —C, (b) —N, and (c) —O;

X and Y are independently at each occurrence selected from the group consisting of:

(a) hydrogen, (b) halide, (c) trifluoromethyl, (d) alkoxy, (e) alkyl, (f) aryl, and (g) substituted aryl;

R is selected from the group consisting of:

(a) $C_2$–$C_{20}$ alkyl, (b) cycloalkyl, (c) heterocycle, (d) substituted heterocycle, (e) alkylcycloalkyl, (f) substituted alkylcycloalkyl, (g) alkylaryl, (f) alkylheterocycle, (g) alkenyl, (h) alkynyl, (i) —C(S)—$NHR_4$, C($NR_4$)—$NHR_4$, wherein $R_4$ is hydrogen, alkyl, or aryl; and (j) —$(CH_2)_n$—C$(CH_2)_m$—$R_5$, wherein m is 2, 3, 4, or 5, and $R_5$ is alkyl, alkoxy, aryl, or substituted aryl;

$R_2$ and $R_3$ are independently at each occurrence (a) hydrogen, (b) methyl, or $R_2$ and $R_3$ together with A to which they are attached may form a cyclic moiety, when A is C; $R_3$ is absent when A is N; and n=1, 2 or 3;

comprising the steps of:

(a) reacting a compound of formula:

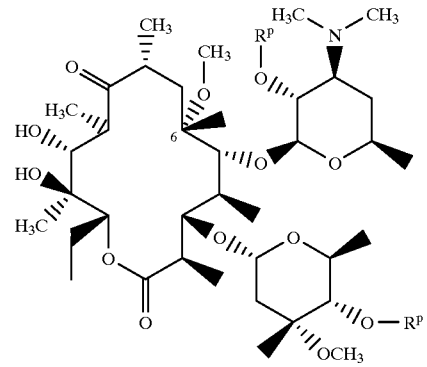

wherein Rp is a hydroxy-protecting group;

with sodium hexamethyldisilazide and carbonyldiimidazole to afford a compound of the formula:

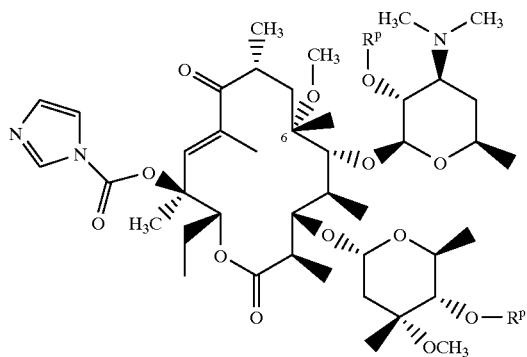

(b) reacting the compound obtained in step (a) with an amino compound of the formula:

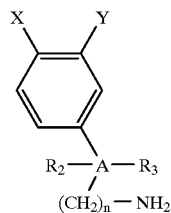

followed by deprotection of 2',4"-protected hydroxyl groups to afford a compound of the formula:

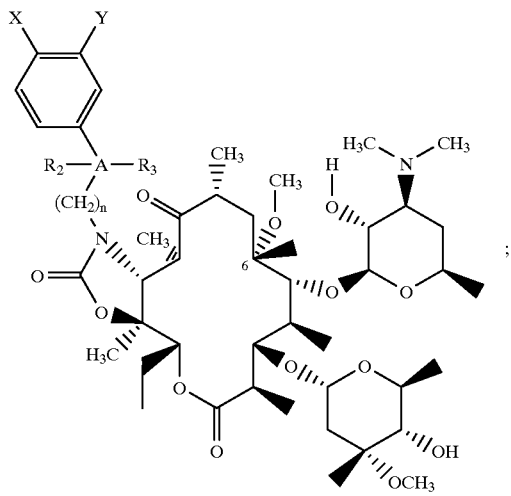

(c) desmethylating the 3'-amino by treating the compound obtained in step (b) to afford a compound of the formula:

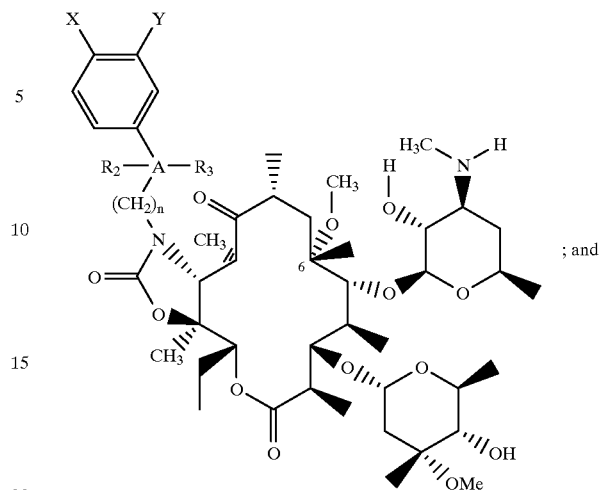

(d) alkylating the 3'-N-desmethylated compound obtained in step (c) with an alkylating agent.

8. The process according to claim 7, wherein the reaction in step (a) is carried out in an aprotic solvent at 0 to 25° C.

9. The process according to claim 7, wherein the reaction in step (b) is carried out without solvent or in acetonitrile at 25 to 80° C.

10. The process according to claim 7, wherein the desmethylation in step (c) is carried out by reaction of the compound obtained in step (b) with iodine in the presence of a base and a light or heat source.

11. The process according to claim 7, wherein the desmethylation in step (c) is carried out by reaction of the compound obtained in step (b) with a chloroformate selected from the group consisting of benzyl chloroformate, allyl chloroformate and vinyl chloroformate.

12. The process according to claim 7, wherein the alkylation in step (d) is achieved by reaction of the compound obtained in step (c) with an aldehyde or ketone in the presence of a hydride metal or in the presence of Pd/C catalyst in a protic or non-protic solvent under hydrogen.

13. The process according to claim 7, wherein the alkylation in step (d) is achieved by reaction of the compound obtained in step (c) with an alkyl halide in presence of a base.

14. The process of claim 7, wherein R is alkyl, alkenyl, cycloalkyl, heterocycle, (heterocyclic)alkyl or alkylcycloalkyl; X and Y are independently at each occurrence chloro, fluoro, dioxalano, hydrogen, or alkoxy; A is —C; $R_2$ and $R_3$ are independently at each occurrence hydrogen or together they form cylopropyl moiety and n is 1.

15. The process of claim 7, wherein the alkylating agent is cyclopentanone and the alkylation is carried out in the presence of sodium cyanoborohydride in methanol.

* * * * *